United States Patent
Riether et al.

(10) Patent No.: US 10,787,432 B2
(45) Date of Patent: *Sep. 29, 2020

(54) N-[(PYRIDYLOXY)PROPANYL]BENZAMIDES

(71) Applicant: Boehringer Ingelheim International GmbH, Ingelheim am Rhein (DE)

(72) Inventors: Doris Riether, Biberach an der Riss (DE); Marco Ferrara, San Donato Milanese (IT); Niklas Heine, Biberach an der Riss (DE); Uta Lessel, Maselheim (DE); Janet Rachel Nicholson, Oberhoefen (DE); Anton Pekcec, Munich (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/090,343

(22) PCT Filed: Apr. 7, 2017

(86) PCT No.: PCT/EP2017/058315
§ 371 (c)(1),
(2) Date: Oct. 1, 2018

(87) PCT Pub. No.: WO2017/178340
PCT Pub. Date: Oct. 19, 2017

(65) Prior Publication Data
US 2019/0112291 A1    Apr. 18, 2019

(30) Foreign Application Priority Data
Apr. 15, 2016    (EP) .................................. 16165529

(51) Int. Cl.
C07D 401/12    (2006.01)
C07D 413/12    (2006.01)
C07D 213/84    (2006.01)
C07D 487/04    (2006.01)
C07D 213/82    (2006.01)
C07D 417/12    (2006.01)
C07D 213/64    (2006.01)

(52) U.S. Cl.
CPC ......... *C07D 401/12* (2013.01); *C07D 213/64* (2013.01); *C07D 213/82* (2013.01); *C07D 213/84* (2013.01); *C07D 413/12* (2013.01); *C07D 417/12* (2013.01); *C07D 487/04* (2013.01)

(58) Field of Classification Search
CPC .................................................. C07D 401/12
USPC ................... 544/315, 333; 514/274, 256
See application file for complete search history.

(56) References Cited

U.S. PATENT DOCUMENTS

| 7,468,367 | B2 | 7/2008 | coulton |
| 9,884,854 | B2 | 2/2018 | riether |
| 2015/0166523 | A1 | 6/2015 | Araki et al. |
| 2019/0112291 | A1 | 4/2019 | Riether |
| 2019/0112295 | A1 | 4/2019 | Riether |

FOREIGN PATENT DOCUMENTS

| EP | 2862855 A1 | 4/2015 |
| WO | 03051872 A1 | 6/2003 |
| WO | 2009011775 A1 | 1/2009 |
| WO | 2014091876 A1 | 6/2014 |
| WO | 2015152367 A1 | 10/2015 |
| WO | 2016034882 A1 | 3/2016 |
| WO | 2017178338 A1 | 10/2017 |
| WO | 2017178339 A1 | 10/2017 |
| WO | 2017178340 A1 | 10/2017 |
| WO | 2017178343 A1 | 10/2017 |
| WO | 2017178344 A1 | 10/2017 |

OTHER PUBLICATIONS

International Search Report for PCT/EP2017/058315 dated May 9, 2017.
International Search Report for PCT/EP2017/058312 dated May 24, 2017.
Written Search Report for PCT/EP2017/058312 dated May 4, 2017.
Suzuki, Discovery and invitro and in vivo profiles of N-ethyl-N-[2-[3-(5-fluoro-2-pyridinyl-)-1H-pyrazol-1-yl-ethyl]-2-(2H-1,2,3-triazol-2-yl)-benzamide asa novel class of dual orexin receptor antagonist, Bioorganic and Medicinal Chemistry, 2014.
International Search Report for PCT/EP2017/058314, dated May 19, 2017.
Written Opinion of the Internation Search Authority for PCT/EP2017/058314 dated May 19, 2017.
International Search Report and Written Opinion for PCT/EP2017/058320 dated May 24, 2017.
International report on Patentability for PCT/EP2017/058314, dated Nov. 2, 2018.
Hackam, Translation of Rsearch Evidence from Animals to Humans, JAMA, 296(14), 2006, 1731-1732.

(Continued)

*Primary Examiner* — Patricia L Morris
(74) *Attorney, Agent, or Firm* — Robert J. Kajubi

(57) ABSTRACT

This invention relates to compounds of formula (I), a process for their preparation, pharmaceutical compositions containing them and their use in the treatment of conditions having an association with the orexin sub-type 1 receptor. Ar, $R^1$, $R^2$, $R^3$, $R^4$, $R^5$, $R^6$ and $R^7$ have meanings given in the description.

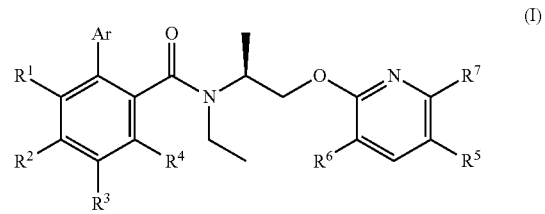

(I)

4 Claims, No Drawings

(56) References Cited

OTHER PUBLICATIONS

Jordan, Tamoxifen, A most unlikely Pioneering Medicine, Nature Reviews, Drug Discovery, 2003, 205.
English abstract for WO2014091876 cited herein.
English abstract for WO20151522367 cited herein.
Blouin et al., Nature Communications, Huma hypocretin and melanin concentrating hormone levels are linked to emotion, 2012.
Piccoli et al., Role of Orexin-1 receptor Mechanisms on Compulsive Food Consumption in a model of binge eating on female rats, Neuropsychopharmacology, vol. 37, 2012.
Scammell et al., Annu. Rev. Pharmal. Orexin Receptors, 2011.

N-[(PYRIDYLOXY)PROPANYL]BENZAMIDES

FIELD OF THE INVENTION

The present invention relates to novel N-[(pyridinyloxy)propanyl]benzamide derivatives, processes for their preparation, pharmaceutical compositions containing them and their use in therapy, particularly in the treatment or prevention of conditions having an association with the orexin sub-type 1 receptor.

BACKGROUND OF THE INVENTION

Orexins are hypothalamic neuropeptides that play an important role in the regulation of many physiological behaviours such as arousal, wakefulness, appetite, food intake, cognition, motivated behaviours, reward, mood and stress. Orexin A, also referred to as hypocretin 1, is a peptide composed of 33 amino acids and orexin B, also referred to as hypocretin 2, is a peptide composed of 28 amino acids. Both are derived from a common precursor peptide referred to as pre-pro-orexin [Sakurai et al., Cell, 1998 Feb. 20; 92(4):573-85, and De Lecea et al., Proc. Nat. Acad. Sci., 1998 Jan. 6; 95(1):322-7). Orexins bind to two orphan G-protein-coupled receptors, the orexin receptor type 1 (OX1R) and orexin receptor type 2 (OX2R), which are widely distributed in the central nervous system and peripheral organs such as adrenal glands, gonads, and gut. Whereas orexin A binds predominantly to OX1R, orexin B is able to bind to both OX1R and OX2R.

Orexins are involved in the regulation of a wide range of behaviours including for example the regulation of emotion and reward, cognition, impulse control, regulation of autonomic and neuroendocrine functions, arousal, vigilance and sleep-wakefulness states (Muschamp et al., Proc. Natl. Acad. Sci. USA 2014 Apr. 22; 111(16):E1648-55; for a recent review see Sakurai, Nat. Rev. Neurosci., 2014; November; 15(11):719-31; Chen et al., Med. Res. Rev., 2015; January; 35(1):152-97; Gotter et al., Pharmacol. Rev., 2012, 64:389-420 and many more).

Dual antagonism of OX1R and OX2R by small molecules is clinically efficacious in the treatment of insomnia, for which the drug suvorexant, [[(7R)-4-(5-chloro-1,3-benzoxazol-2-yl)-7-methyl-1,4-diazepan-1-yl][5-methyl-2-(2H-1,2,3-triazol-2-yl)phenyl]methanone] has been granted marketing authorisation (Kishi et al., PLoS One, 2015; 10(8): e0136910). The sleep-inducing effects of dual orexin receptor antagonists are predominantly mediated via OX2R (Bonaventure et al., J. Pharmacol. Exp. Ther., March 2015, 352, 3, 590-601), whereas the other physiological states such as emotion and reward, cognition, impulse control, regulation of autonomic and neuroendocrine functions, arousal, and vigilance are rather mediated via OX1R. Due to their sleep-inducing effects, dual OX1R and OX2R antagonists are not suitable for treating disorders related to impulse control deficits as seen in addictions such as substance use disorders, personality disorders, such as borderline personality disorder, eating disorders such as binge eating disorder or attention deficit hyperactivity disorder. Therefore, it is desirable to provide an OX1R selective antagonist for the treatment of impulse control deficits.

Orexin receptor antagonists of various structural classes are reviewed in Roecker et al. (J. Med. Chem. 2015, 59, 504-530). WO2013/187466, WO2016/034882 and Bioorganic & Medicinal Chemistry 2015, 23, 1260-1275 describe orexin receptor antagonists.

DETAILED DESCRIPTION OF THE INVENTION

The present invention provides novel N-ethyl-N-[(2S)-1-(pyridin-2-yloxy)-propan-2-yl]-benzamide derivatives of formula I

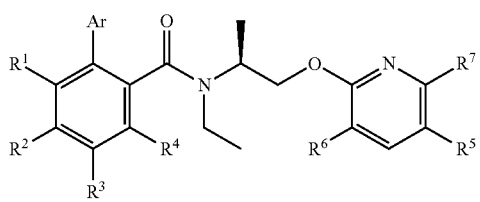

in which
Ar represents

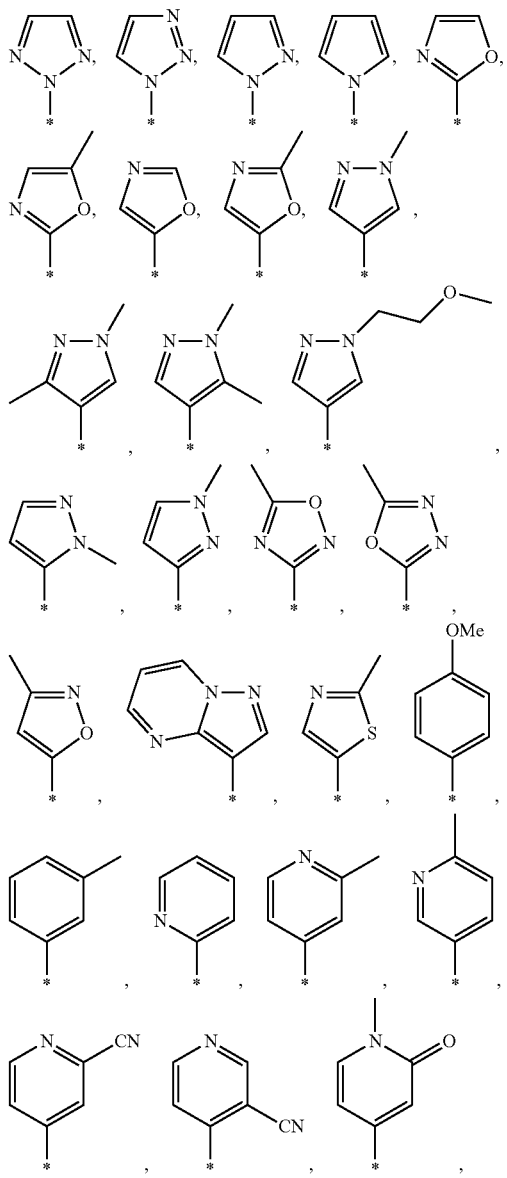

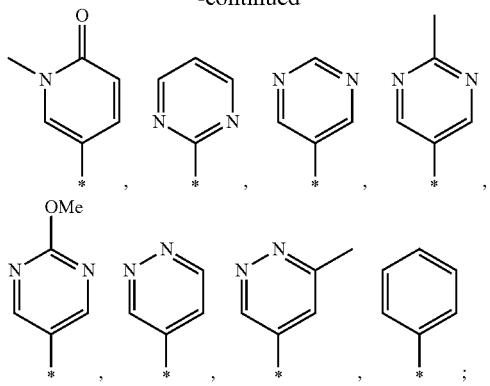

R$^1$ represents hydrogen, fluoro, chloro, methyl;

R$^2$ and R$^3$ independently represent hydrogen, fluoro, chloro, cyano, methyl, —OCH$_3$;

R$^4$ represents hydrogen or fluoro;

R$^5$ represents chloro, bromo, fluoro, —CF$_3$, —OCF$_3$ or cyclopropyl;

R$^6$ represents hydrogen, chloro or fluoro,

R$^7$ represents hydrogen or —CF$_3$, or a salt thereof, particularly a physiologically acceptable salt thereof.

In another embodiment, in the general formula I, Ar, R$^5$, R$^6$ and R$^7$ have the same meanings as defined in any of the preceding embodiments, and at least two of the substituents R$^1$, R$^2$, R$^3$ and R$^4$ represent hydrogen.

In another embodiment, in the general formula I, Ar, R$^1$, R$^2$, R$^3$, R$^4$ and R$^6$ have the same meanings as defined in any of the preceding embodiments, and R$^5$ represents —CF$_3$, R$^7$ represents hydrogen.

In another embodiment, in the general formula I, R$^1$, R$^2$, R$^3$, R$^4$, R$^5$, R$^6$ and R$^7$ have the same meanings as defined in any of the preceding embodiments, and Ar represents

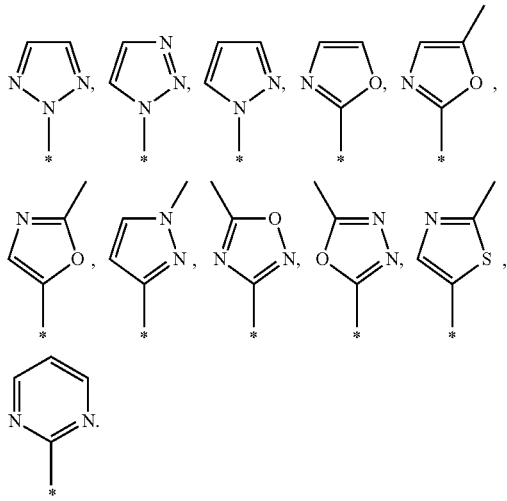

In another embodiment, in the general formula I, Ar, R$^2$, R$^3$, R$^4$, R$^5$, R$^6$ and R$^7$ have the same meanings as defined in any of the preceding embodiments, and R$^1$ represents hydrogen, fluoro or chloro.

In another embodiment, in the general formula I, Ar, R$^1$, R$^3$, R$^4$, R$^5$, R$^6$ and R$^7$ have the same meanings as defined in any of the preceding embodiments, and R$^2$ represents hydrogen or fluoro.

In another embodiment, in the general formula I, Ar, R$_1$, R$^2$, R$^4$, R$^5$, R$^6$ and R$^7$ have the same meanings as defined in any of the preceding embodiments, and R$^3$ represents hydrogen, fluoro or cyano.

In another embodiment, in the general formula I, Ar, R$^1$, R$^2$, R$^3$, R$^5$, R$^6$ and R$^7$ have the same meanings as defined in any of the preceding embodiments, and R$^4$ represents hydrogen.

In another embodiment, in the general formula I, R$^1$, R$^2$, R$^3$, R$^4$, R$^5$, R$^6$ and R$^7$ have the same meanings as defined in any of the preceding embodiments, and Ar represents

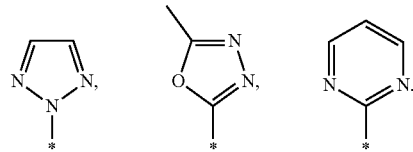

In another embodiment, in the general formula I, R$^5$, R$^6$ and R$^7$ have the same meanings as defined in any of the preceding embodiments, and Ar represents

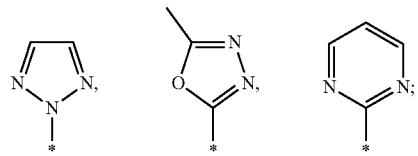

R$^1$ represents hydrogen, fluoro or chloro;

R$^2$ represents hydrogen or fluoro;

R$^3$ represents hydrogen, fluoro or cyano;

R$^4$ represents hydrogen.

Compounds of the present invention are potent OX1R antagonists. They are more selective over the OX2R than preferred examples disclosed in WO2013/187466. Compounds of the present invention differ structurally from those disclosed in WO2013/187466 in that they contain a substituted —O-pyridyl moiety in place of a Het1-Het2 moiety in which Het2 is phenyl or pyridyl. These structural differences unexpectedly result in an explicit enhancement in selectivity over the OX2R.

Compounds of the present invention differ structurally from Examples 1, 42 and 14 in WO2016/034882 (closest prior art) in that they contain a central N-ethyl-(propan-2-yl)amino moiety in place of the N-methyl-[butan-2-yl]amino or N-methyl-[(propan-2-yl]amino moiety and an —O-pyridyl instead of the —N-pyridyl moiety. The structural differences unexpectedly result in superior pharmacokinetic properties demonstrated by improved stability in human liver microsomes. Therefore, compounds of the present invention are expected to have a medium to low in vivo clearance and thus a longer duration of action and better tolerability due to the larger window between efficacy and undesired effects such as drowsiness and sleep. Consequently, compounds of the present invention must be more viable for human use.

General Definitions

Terms not specifically defined herein should be given the meanings that would be given to them by one skilled in the art in light of the disclosure and the context.

Stereochemistry:

Unless specifically indicated, throughout the specification and the appended claims, a given chemical formula or name shall encompass tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetate salts) also comprise a part of the invention.

Biological Assays

Abbreviations:

IP1 D-Myo-Inositol-1-phosphate
IP3 D-myo-inositol-1,4,5-triphosphate
HEPES 4-(2-hydroxyethyl)-1-piperazineethanesulfonic acid
HBSS Hanks' Balanced Salt Solution
BSA bovine serum albumin
DMSO dimethyl sulfoxide
CHO Chinese hamster ovary Activation of the orexin receptors expressed in cell lines results in an increase in intracellular IP3 concentration. IP1, a downstream metabolite of IP3, accumulates in cells following receptor activation and is stable in the presence of LiCl. Using Homogeneous Time-Resolved Fluorescence technology with Lumi4-Tb cryptate (commercially available from Cisbio Bioassay.) and a suitable fluorescence plate reader. This functional response is detectable and quantifiable as described in Trinquet et al. Anal. Biochem. 2006, 358, 126-135, Degorce et al. Curr. Chem. Genomics 2009, 3, 22-32. This technique is used to characterize pharmacological modification of the orexin receptors.

The biological activity of compounds is determined by the following methods:

A. In Vitro Testing of OX1R Potency: OX1R IP1

IP1 measurements are performed in CHO-K1 cells stably expressing the full-length human Orexin 1 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOX1 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is re-suspended in medium and then distributed into the assay plates with a density of 10000 cells/25 μL per well. The plates are incubated for one hour at room temperature to reduce edge effects before they are incubated for 24 hours at 37° C./5% $CO_2$. Compounds are prepared by an 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM, and/or 50 nM) dissolved in assay buffer is added to the assay plate. The assay plate is incubated for 60 minutes at 37° C. Then 5 μL per well of Anti-IP1-Cryptate Tb solution and 5 μL per well of IP1-d2 dilution are added and the plate is incubated for a further 60 minutes light protected at room temperature. The emissions at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})^n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

B. In Vitro Testing of OX2R Potency: OX2R IP1

IP1 measurements are performed in CHO-K1 cells stably expressing the full-length human orexin 2 receptor and the aequorin photoprotein. Cells are cultivated in Ham's nutrient mixture F12 medium with 10% fetal calf serum, in a 37° C., 95% humidity and 5% $CO_2$ incubator. The CHO-K1/hOX2 cell mass is expanded to larger cell numbers. The cells are obtained as frozen cells in cryo-vials and stored until use at −150° C. The viability of the cells after thawing is >90%. In preparation for the assay, 24 hours before the assay, the cells are thawed at 37° C. and immediately diluted with cell culture medium. After centrifugation, the cell pellet is resuspended in medium and then distributed into the assay plates with a density of 5000 cells/25 μL per well. The plates are incubated for one hour at room temperature to reduce edge effects before they are incubated for 24 hours at 37° C./5% $CO_2$. Compounds are prepared by a 8-point serial dilution in DMSO and a final dilution step into assay buffer (HBSS with 20 mM HEPES, 0.1% BSA and 50 mM LiCl, pH 7.4) to ensure a final DMSO concentration of 1% in the assay.

On the day of the assay, cells in the plate are washed twice with 60 μL assay buffer (20 μL buffer remained in the wells after washing), followed by adding 5 μL per well of compounds diluted in assay buffer. After 15 minutes of incubation at room temperature 5 μL per well of Orexin A peptide (final concentration: 0.5 nM) dissolved in assay buffer is added to the assay plate. The assay plate is incubated for 60 minutes at 37° C. Then 5 μL per well of Anti-IP1-Cryptate Tb solution and 5 μL per well of IP1-d2 dilution are added to all well of the plate and the plate is incubated for a further 60 minutes light protected at room temperature. The emission at 615 nm and 665 nm (Excitation wavelength: 320 nm) are measured using an EnVision reader (PerkinElmer). The ratio between the emission at 665 nm and 615 is calculated by the reader.

8-point four parametric non-linear curve fitting and determination of $IC_{50}$ values and Hill slopes is performed using a regular analysis software e.g. AssayExplorer (Accelrys). In order to establish an agonist concentration independent parameter, Kb values are calculated using the following equation: $IC_{50}/((2+(A/EC_{50})_n)^{1/n}-1)$ (with A=concentration agonist, $EC_{50}=EC_{50}$ agonist, n=Hill slope agonist) (see P. Leff, I. G. Dougall, Trends Pharmacol. Sci. 1993, 14(4), 110-112).

Kb values from Assay A (OX1R) and Assay B (OX2R) can then provide a selectivity ratio which is independent of the agonist (Orexin A) concentration.

C. Assessment of Metabolic Stability in Human Liver Microsomes (Human MST)

The metabolic stability of the compounds according to the invention may be investigated as follows:

The metabolic degradation of the test compound is assayed at 37° C. with pooled human liver microsomes. The final incubation volume of 100 μL per time point contains TRIS buffer pH 7.6 at room temperature (0.1 M), $MgCl_2$ (5 mM), microsomal protein (1 mg/mL) and the test compound at a final concentration of 1 μM. Following a short pre-incubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life ($t_{1/2}$) is determined by the slope of the semi-logarithmic plot of the concentration-time profile.

Biological Data

Comparison of Assays A and B with the Assays Described in WO2013/187466

Assays described in WO2013/187466 differ from assays A and B in:

The technology and readout: fluorescence measurement of intracellular $Ca^{2+}$ changes (WO2013/187466) instead of luminescence measurement of IP1 (assays A and B)

OX1R and OX2R overexpressing cell lines used for the assays described in WO 2013/187466 are of different origin as cell lines used for assays A and B Use of modified orexin A (2 amino acids substituted) as agonist instead of orexin A Agonist concentration of 300 pM used for the OX1R assay and 3 nM for the OX2R assay (EC75 vs. EC100; according to Okumura T. et al., Biochemical and Biophysical Research Communications, 2001) (WO2013/187466). $IC_{50}$ values that have been reported are dependent on the agonist concentration. Selectivity ratios calculated from these $IC_{50}$ values cannot be compared with the selectivity ratios calculated from the agonist concentration independent Kb values obtained from assay A and B.

Due to these differences between the assays, a direct comparison has to be established. Therefore, examples 69, 70 (the most selective ones) and 5 (one of the most potent ones) described in WO2013/187466 are tested in assays A and B so as to be directly compared with compounds of the present invention (see Table 1).

TABLE 1

In vitro potencies of compounds of WO2013/187466 as reported therein versus as determined in the Assays A and B (described above)

| Structure Example # in WO2013/187466 | As described in WO2013/187466 | | | As determined in Assays A and B | | |
|---|---|---|---|---|---|---|
| | OX1R $IC_{50}$ [nM] | OX2R $IC_{50}$ [nM] | OX2R $IC_{50}$/ OX1R $IC_{50}$ | OX1R Kb (Orexin A concentration used) | OX2R Kb [nM] (0.5 nM Orexin A concentration) | OX2R Kb/ OX1R Kb |
| Example 69 | 1.6 | 1896 | 1185 | 2.25 (0.5 nM) | 98 | 43 |

TABLE 1-continued

In vitro potencies of compounds of WO2013/187466 as reported therein versus as determined in the Assays A and B (described above)

| Structure Example # in WO2013/187466 | As described in WO2013/187466 | | | As determined in Assays A and B | | |
|---|---|---|---|---|---|---|
| | OX1R IC$_{50}$ [nM] | OX2R IC$_{50}$ [nM] | OX2R IC$_{50}$/ OX1R IC$_{50}$ | OX1R Kb [nM] (Orexin A concentration used) | OX2R Kb [nM] (0.5 nM Orexin A concentration) | OX2R Kb/ OX1R Kb |
| 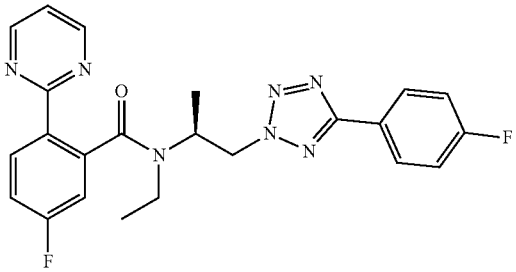 [SMILES: CCN(C(=O)c1cc(F)ccc1-c1ncccn1)[C@@H](C)Cn1nnc(-c2ccc(F)cc2)n1]<br>Example 70 | 1.1 | 452 | 411 | 0.72 (50 nM) | 29 | 40 |
| 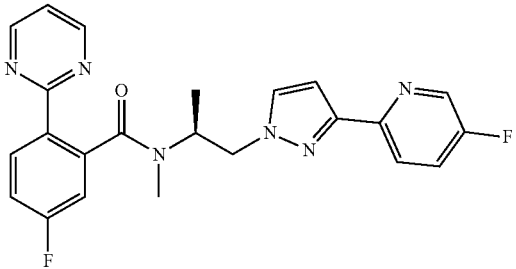 [SMILES: C[C@@H](Cn1ccc(-c2ccc(F)cn2)n1)N(C)C(=O)c1cc(F)ccc1-c1ncccn1]<br>Example 5 | 0.5 | 76 | 152 | 0.94 (50 nM) | 28 | 30 |

TABLE 2

In vitro potencies of the structurally closest prior art compounds (Example 1, 42 and 14) WO2016/034882 as reported therein:

| Structure Example # in WO2016/034882 | As described in WO2016/034882 (Table 1, page 178) | | |
|---|---|---|---|
| | OX1R | OX2R | OX2R IC$_{50}$/ OX1R IC$_{50}$ |
| 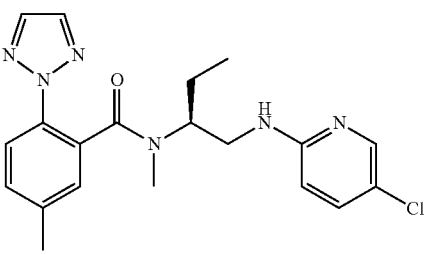 [SMILES: CC[C@@H](CNc1ccc(Cl)cn1)N(C)C(=O)c1cc(C)ccc1-n1nccn1]<br>Example 1 | Table 1: pIC$_{50}$ = 7.7 corresponds to IC$_{50}$ = 20 nM<br>Table 2: pIC$_{50}$ = 8.1 corresponds to IC$_{50}$ = 7.9 nM<br>Table 3: not reported | Table 1: pIC$_{50}$ = 6.0 corresponds to IC$_{50}$ = 1000 nM<br>Table 2: pIC$_{50}$ = 5.9 corresponds to IC$_{50}$ = 1259 nM<br>Table 3: not reported | Table 1: 50<br>Table 2: 159 |

TABLE 2-continued

In vitro potencies of the structurally closest prior art compounds (Example 1, 42 and 14) WO2016/034882 as reported therein:

| Structure Example # in WO2016/034882 | As described in WO2016/034882 (Table 1, page 178) | | |
|---|---|---|---|
| | OX1R | OX2R | OX2R IC$_{50}$/ OX1R IC$_{50}$ |
| Example 42 | Table 1: pIC$_{50}$ = 7.9 corresponds to IC$_{50}$ = 12.6 nM Table 2 and 3: not reported | Table 1: pIC$_{50}$ = 6.0 corresponds to IC$_{50}$ = 1000 nM Table 2 and 3: not reported | Table 1: 79 |
| Example 14 | Table 1: pIC$_{50}$ = 8.3 corresponds to IC$_{50}$ = 5.0 nM Table 2: pIC$_{50}$ = 7.8 corresponds to IC$_{50}$ = 16 nM Table 3: not reported | Table 1: pIC$_{50}$ = 6.8 corresponds to IC$_{50}$ = 158 nM Table 2: pIC$_{50}$ = 7.2 corresponds to IC$_{50}$ = 63 nM Table 3: not reported | Table 1: 32 Table 2: 4 |

Table 3 shows a comparison of biological data on the OX1R and OX2R potencies as well as stability in human liver microsomes of compounds of the present invention with those of the closest prior art compounds in WO 2016/034882. These data demonstrate that compounds of the present invention are more stable in human liver microsomes.

Examples 28, 29, 30, 32, 33, 45, 46 and 114 of the present invention differ structurally from Example 1 in WO2016/034882, the closest prior art compounds, in that a) they contain a central N-ethyl-(propan-2-yl)amino moiety in place of the N-methyl-[butan-2-yl]amino moiety; b) they contain a —O-pyridyl instead of the —N-pyridyl moiety; c) the phenyl group is either unsubstituted or substituted with one or two fluorines, chlorine or methoxy instead of methyl and the substituent may be in a different position. Unexpectedly, these structural differences lead to a markedly improved stability in human liver microsomes.

Examples 36, 38 and 39 of the present invention differ structurally from Example 1 in WO2016/034882, the closest prior art compounds, in that a) they contain a central N-ethyl-(propan-2-yl)amino moiety in place of the N-methyl-[butan-2-yl]amino moiety; b) they contain a —O-pyridyl instead of the —N-pyridyl moiety; c) they contain a different 5-membered heteroaryl instead of the triazoyl group; and d) the phenyl group has a fluoro or methyl substituent in a different position as compared to the methyl in the closest prior art compound. Unexpectedly, these structural differences lead to a markedly improved stability in human liver microsomes.

Examples 1, 3, 4, 10, 13, 15, 26, 90, 91, 92, 94, 95, 103, 109, 47, 48, 49, 50, 51, 52, 54, 56, 57, 73, 69, 113, 127, 131, 110, 111, 112, 126, 133 and 134 of the present invention differ structurally from Example 42 in WO2016/034882, the closest prior art compounds, in that a) they contain a central N-ethyl-(propan-2-yl)amino moiety in place of the N-methyl-[butan-2-yl]amino moiety; b) they contain a —O-pyridyl instead of the —N-pyridyl moiety; c) the phenyl group is unsubstituted or substituted with one or two fluoro, chloro, cyano, methoxy or a methyl and fluoro substituent instead of the chloro substituent and the substituent may be in a different position. Examples 47, 48, 49, 50, 51, 52, 54, 56, 57, 73, 69, 110, 113, 127, and 131 differ structurally farther from Example 42 in WO2016/034882 in that d) the pyridyl moiety is substituted with a fluoro or chloro substituent in addition to the CF3-group. Examples 111, 112, 126, and 134 are substituted with a bromo or OCF3 substituent instead of the CF3 group and may contain an additional fluoro substituent. In Example 133 the CF3 substituent on the pyridyl is in a different position in comparison with the closest prior art compound and contains an additional fluoro substituent. Unexpectedly, these structural differences lead to a markedly improved stability in human liver microsomes.

Examples 14, 18, 20, 22, 74, 93, and 123, 55, 61, 64, 68, 124, 132, and 121 of the present invention differ structurally from Example 42 in WO2016/034882, the closest prior art compounds, in that a) they contain a central N-ethyl-(propan-2-yl)amino moiety in place of the N-methyl-[butan-2-yl]amino moiety; b) they contain a —O-pyridyl instead of the —N-pyridyl moiety; c) the phenyl group is not substituted or substituted with a fluoro, or a methyl which may be in a different position compared to the chloro substituent in the closest prior art compound, and d) they contain another alternative heteroaryl group in place of the triazoyl group. Examples 55, 61, 64, 68, 124 and 132 differ structurally farther in that they e) contain an additional fluoro substituent on the pyridyl, whereas Example 121 contains a OCF3 substituent instead of the CF3 group. These structural differences unexpectedly result in a markedly improved stability in human liver microsomes.

Examples 76, 79, 81, 84, 85, 96, 97, 101, 102, 105, 107, 108, 116, 118, 117, 120, 125, 129 and 130 of the present invention differ structurally from Example 14 in WO2016/034882, the closest prior art compounds, in that a) they contain a central N-ethyl-(propan-2-yl)amino moiety in place of the N-methyl-[propan-2-yl]amino moiety; b) they contain a —O-pyridyl instead of the —N-pyridyl moiety; c) they contain a pyridyl, pyrimidyl or a pyridazinyl moiety instead of the second phenyl group and the heteroaryl group may be substituted with a methyl, cyano or methoxy; and d) the first phenyl group may be substituted with a fluoro, methoxy or methyl substituent.

Unexpectedly, these structural differences lead to a markedly improved stability in human liver microsomes.

TABLE 3

| | | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| Example | Structure | | | | |
| Ex 1 in WO2016/034882 | | 0.18 (50 nM) | 36 | 200 | 5 |
| 28 | | 1.7 (0.5 nM and 50 nM) | 86 | 51 | 39 |
| 29 | | 1.0 (0.5 nM) 0.88 (50 nM) | 71 | 71 81 | 55 |
| 30 | | 2.3 (0.5 nM) | 160 | 70 | 52 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 32 | 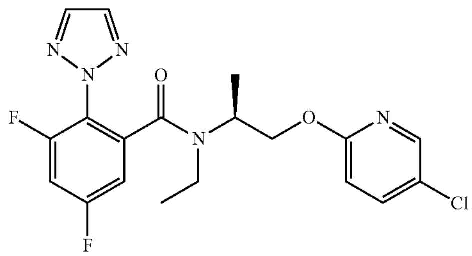 [SMILES: CCN(C(=O)c1cc(F)cc(F)c1-n1nccn1)[C@@H](C)COc1ccc(Cl)cn1] | 1.1 (0.5 nM) 0.82 (50 nM) | 117 | 106 143 | 46 |
| 33 | 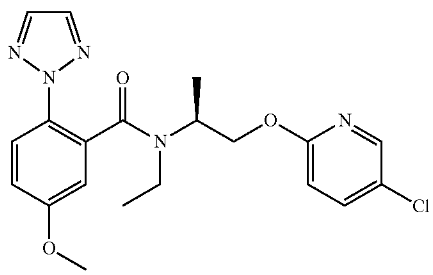 [SMILES: CCN(C(=O)c1cc(OC)ccc1-n1nccn1)[C@@H](C)COc1ccc(Cl)cn1] | 0.14 (50 nM) | 33 | 236 | 20 |
| 45 | 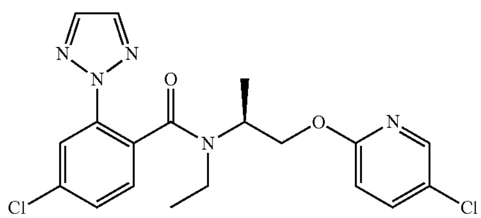 [SMILES: CCN(C(=O)c1ccc(Cl)cc1-n1nccn1)[C@@H](C)COc1ccc(Cl)cn1] | 0.354 (50 nM) | 21 | 59 | 18 |
| 46 | 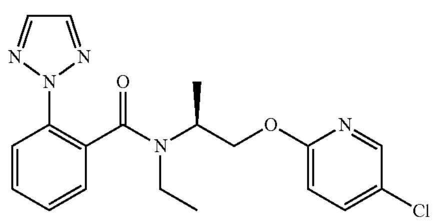 [SMILES: CCN(C(=O)c1ccccc1-n1nccn1)[C@@H](C)COc1ccc(Cl)cn1] | 0.66 (50 nM) | 37 | 56 | 35 |
| 114 | 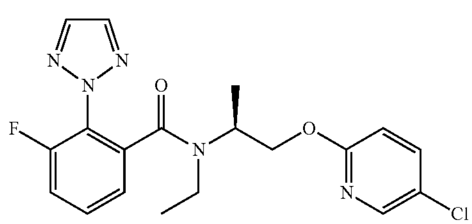 [SMILES: CCN(C(=O)c1cccc(F)c1-n1nccn1)[C@@H](C)COc1ccc(Cl)cn1] | 0.59 (0.5 nM) 0.55 (50 nM) | 54 | 92 98 | 110 |
| 36 | 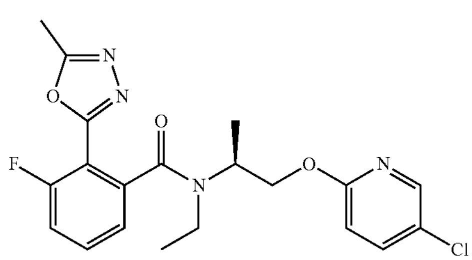 [SMILES: CCN(C(=O)c1cccc(F)c1-c1nnc(C)o1)[C@@H](C)COc1ccc(Cl)cn1] | 3.9 (0.5 nM) | 542 | 139 | 72 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 38 | 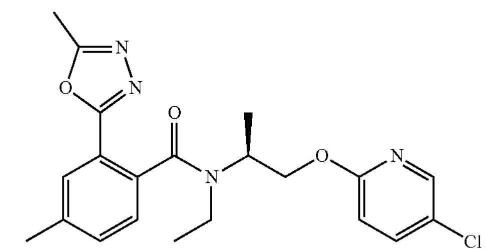 [SMILES: CCN(C(=O)c1ccc(C)cc1-c1nnc(C)o1)[C@@H](C)COc1ccc(Cl)cn1] | 2.8 (0.5 nM) | 877 | 313 | 11 |
| 39 | 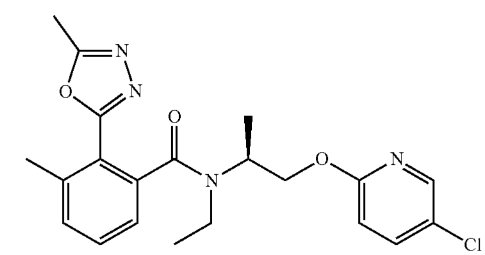 [SMILES: CCN(C(=O)c1cccc(C)c1-c1nnc(C)o1)[C@@H](C)COc1ccc(Cl)cn1] | 0.88 (0.5 nM) 0.54 (50 nM) | 82 | 93 152 | 23 |
| Ex 42 in WO2016/ 034882 | 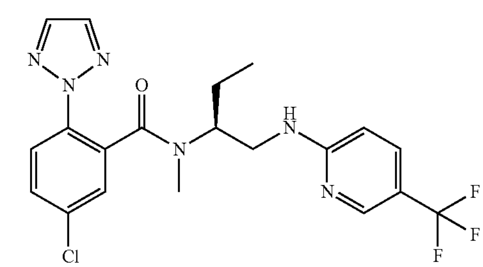 [SMILES: CC[C@@H](CNc1ccc(C(F)(F)F)cn1)N(C)C(=O)c1cc(Cl)ccc1-n1nccn1] | 2.20 (0.5 nM) 2.33 (50 nM) | 229 | 104 98 | 7 |
| 1 | 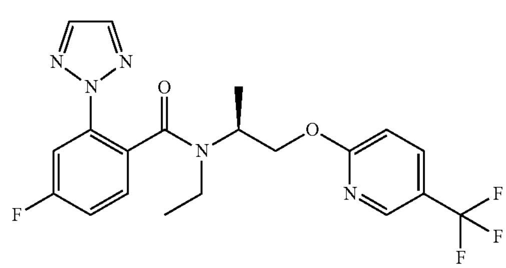 [SMILES: CCN(C(=O)c1ccc(F)cc1-n1nccn1)[C@@H](C)COc1ccc(C(F)(F)F)cn1] | 0.34 (0.5 nM) | 58 | 171 | 38 |
| 3 | 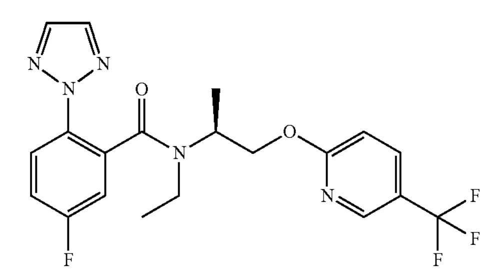 [SMILES: CCN(C(=O)c1cc(F)ccc1-n1nccn1)[C@@H](C)COc1ccc(C(F)(F)F)cn1] | 0.28 (50 nM) | 44 | 157 | 62 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 4 | 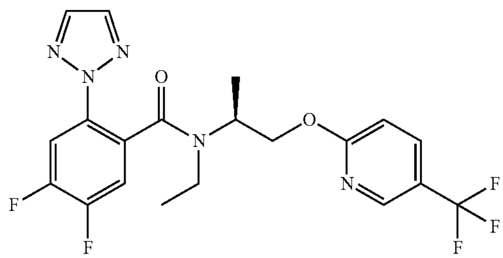 [SMILES: CCN(C(=O)c1cc(F)c(F)cc1-n1nccn1)[C@@H](C)COc1ccc(C(F)(F)F)cn1] | 0.50 (0.5 nM) 0.74 (50 nM) | 138 | 276 187 | 61 |
| 10 | 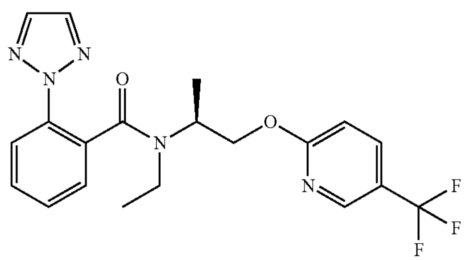 [SMILES: CCN(C(=O)c1ccccc1-n1nccn1)[C@@H](C)COc1ccc(C(F)(F)F)cn1] | 0.18 (50 nM) | 21 | 117 | 24 |
| 13 | 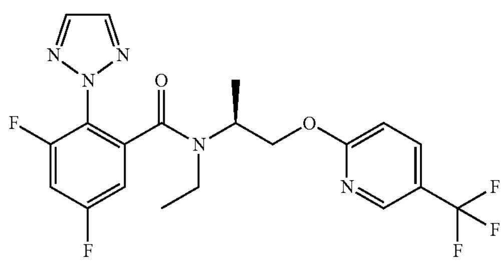 [SMILES: CCN(C(=O)c1cc(F)cc(F)c1-n1nccn1)[C@@H](C)COc1ccc(C(F)(F)F)cn1] | 0.18 (50 nM) | 92 | 511 | 49 |
| 15 | 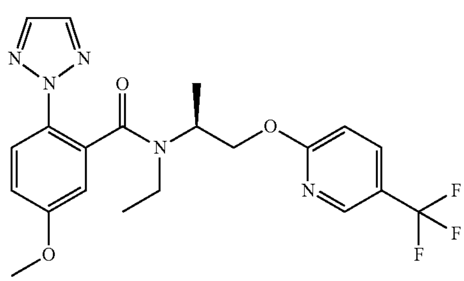 [SMILES: CCN(C(=O)c1cc(OC)ccc1-n1nccn1)[C@@H](C)COc1ccc(C(F)(F)F)cn1] | 0.060 (50 nM) | 15 | 250 | 16 |
| 26 | 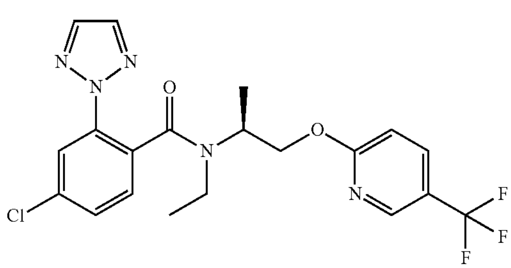 [SMILES: CCN(C(=O)c1ccc(Cl)cc1-n1nccn1)[C@@H](C)COc1ccc(C(F)(F)F)cn1] | 0.055 (50 nM) | 22 | 400 | 15 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 90 | 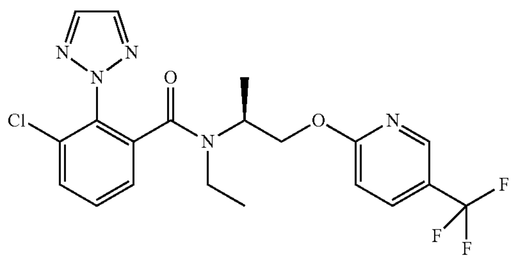 [SMILES: CCN(C(=O)c1cccc(Cl)c1-n1nccn1)[C@@H](C)COc1ccc(C(F)(F)F)cn1] | 0.025 (50 nM) | 13 | 520 | 44 |
| 91 | 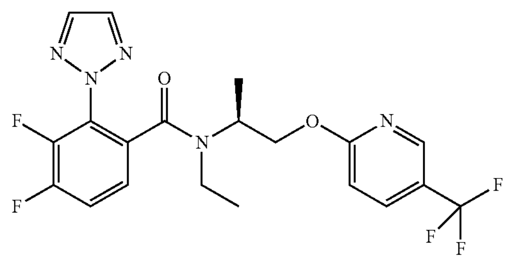 [SMILES: CCN(C(=O)c1ccc(F)c(F)c1-n1nccn1)[C@@H](C)COc1ccc(C(F)(F)F)cn1] | 0.20 (50 nM) | 68 | 340 | 18 |
| 92 | 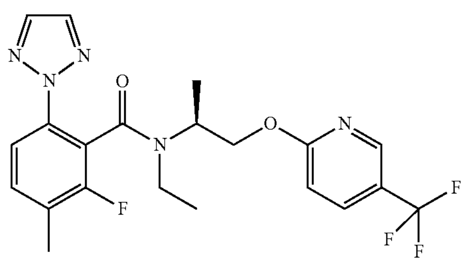 [SMILES: CCN(C(=O)c1c(-n2nccn2)ccc(C)c1F)[C@@H](C)COc1ccc(C(F)(F)F)cn1] | 0.025 (50 nM) | 16 | 640 | 18 |
| 94 | 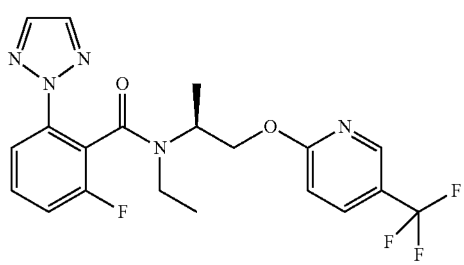 [SMILES: CCN(C(=O)c1c(F)cccc1-n1nccn1)[C@@H](C)COc1ccc(C(F)(F)F)cn1] | 0.37 (50 nM) | 78 | 211 | 31 |
| 95 | 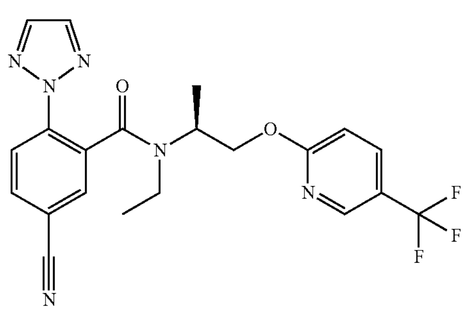 [SMILES: CCN(C(=O)c1cc(C#N)ccc1-n1nccn1)[C@@H](C)COc1ccc(C(F)(F)F)cn1] | 0.52 (0.5 nM) 0.50 (50 nM) | 37 | 71 74 | >130 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 103 | 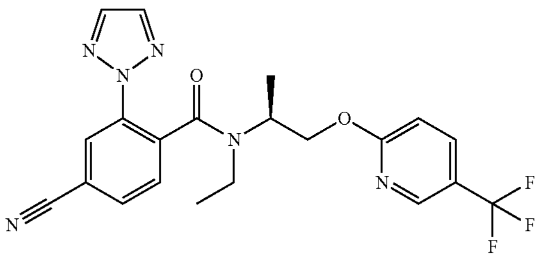 [SMILES: CCN(C(=O)c1ccc(C#N)cc1-n1nccn1)[C@@H](C)COc1ccc(C(F)(F)F)cn1] | 4.28 (0.5 nM) | 1170 | 273 | 58 |
| 109 | 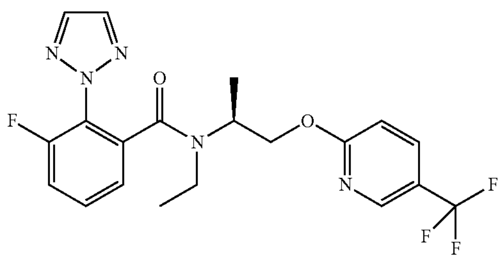 [SMILES: CCN(C(=O)c1cccc(F)c1-n1nccn1)[C@@H](C)COc1ccc(C(F)(F)F)cn1] | 0.11 (50 nM) | 36 | 327 | 75 |
| 47 | 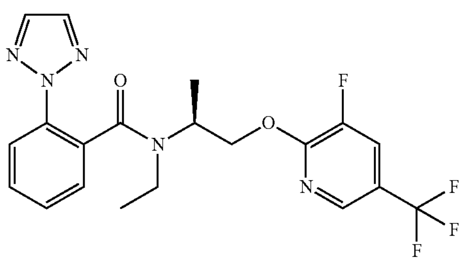 [SMILES: CCN(C(=O)c1ccccc1-n1nccn1)[C@@H](C)COc1ncc(C(F)(F)F)cc1F] | 0.67 (0.5 nM)<br>0.32 (50 nM) | 87 | 130<br>272 | 21 |
| 48 | 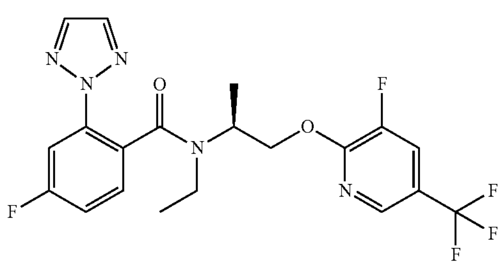 [SMILES: CCN(C(=O)c1ccc(F)cc1-n1nccn1)[C@@H](C)COc1ncc(C(F)(F)F)cc1F] | 1.31 (0.5 nM)<br>0.93 (50 nM) | 205 | 156<br>220 | 31 |
| 49 | 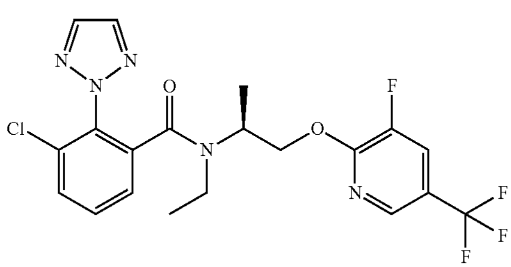 [SMILES: CCN(C(=O)c1cccc(Cl)c1-n1nccn1)[C@@H](C)COc1ncc(C(F)(F)F)cc1F] | 0.066 (50 nM) | 22 | 333 | 81 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 50 | 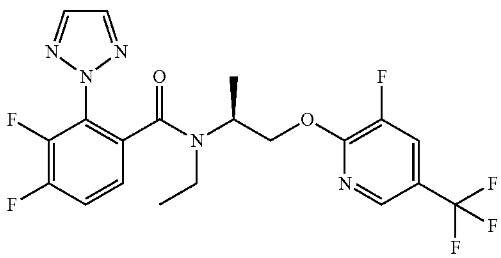 [SMILES: CCN(C(=O)c1ccc(F)c(F)c1-n1nccn1)[C@@H](C)COc1ncc(C(F)(F)F)cc1F] | 0.69 (50 nM) | 283 | 410 | 46 |
| 51 | 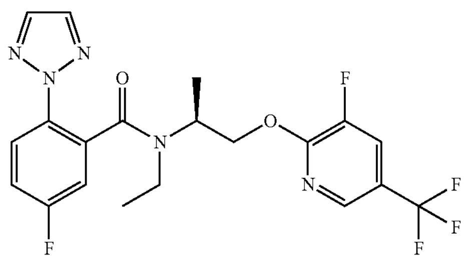 [SMILES: CCN(C(=O)c1cc(F)ccc1-n1nccn1)[C@@H](C)COc1ncc(C(F)(F)F)cc1F] | 0.73 (0.5 nM) 0.44 (50 nM) | 189 | 259 430 | 36 |
| 52 | 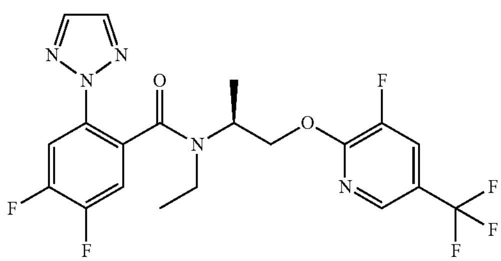 [SMILES: CCN(C(=O)c1cc(F)c(F)cc1-n1nccn1)[C@@H](C)COc1ncc(C(F)(F)F)cc1F] | 2.1 (0.5 nM) | 538 | 256 | 38 |
| 54 | 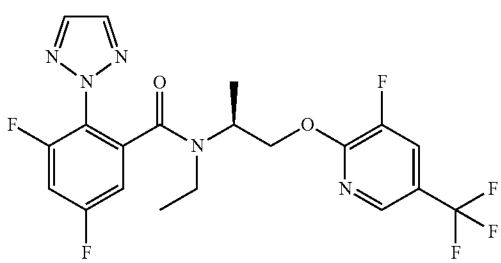 [SMILES: CCN(C(=O)c1cc(F)cc(F)c1-n1nccn1)[C@@H](C)COc1ncc(C(F)(F)F)cc1F] | 0.99 (0.5 nM) 0.66 (50 nM) | 274 | 277 415 | 87 |
| 56 | 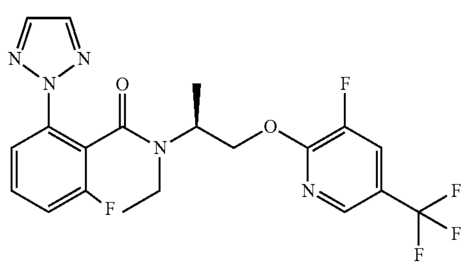 [SMILES: CCN(C(=O)c1c(F)cccc1-n1nccn1)[C@@H](C)COc1ncc(C(F)(F)F)cc1F] | 1.1 (0.5 nM) 0.42 (50 nM) | 108 | 98 257 | 48 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 57 | 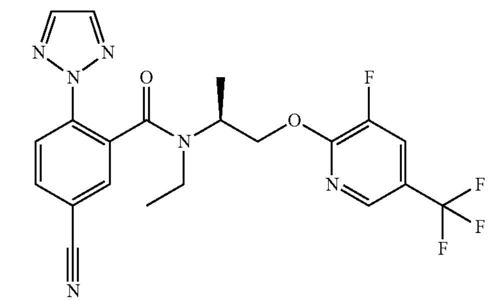 [SMILES: CCN(C(=O)c1cc(C#N)ccc1-n1nccn1)[C@@H](C)COc1ncc(C(F)(F)F)cc1F] | 0.95 (50 nM) | 203 | 214 | >130 |
| 73 | 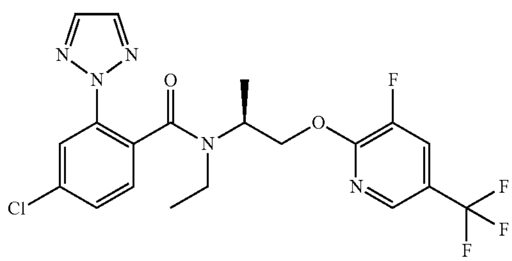 [SMILES: CCN(C(=O)c1ccc(Cl)cc1-n1nccn1)[C@@H](C)COc1ncc(C(F)(F)F)cc1F] | 0.32 (50 nM) | 235 | 734 | 12 |
| 69 | 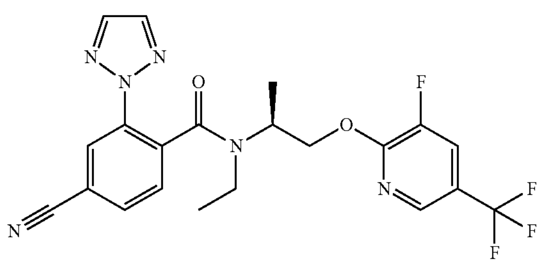 [SMILES: CCN(C(=O)c1ccc(C#N)cc1-n1nccn1)[C@@H](C)COc1ncc(C(F)(F)F)cc1F] | 32 (0.5 nM) | 4336 | 136 | 43 |
| 113 | 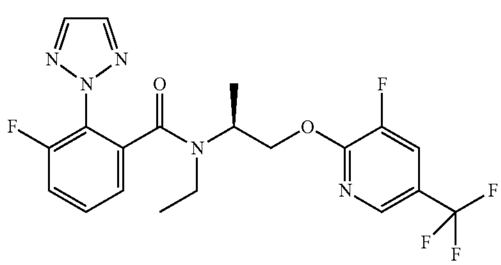 [SMILES: CCN(C(=O)c1cccc(F)c1-n1nccn1)[C@@H](C)COc1ncc(C(F)(F)F)cc1F] | 0.40 (0.5 nM) | 69 | 173 | 95 |
| 127 | 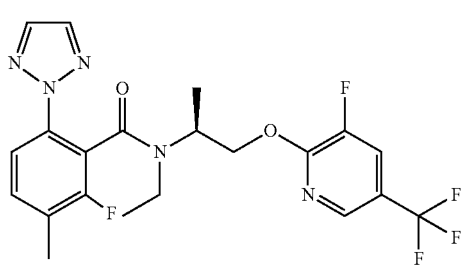 [SMILES: CCN(C(=O)c1c(-n2nccn2)ccc(C)c1F)[C@@H](C)COc1ncc(C(F)(F)F)cc1F] | 0.13 (50 nM) | 49 | 377 | 15 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 131 | 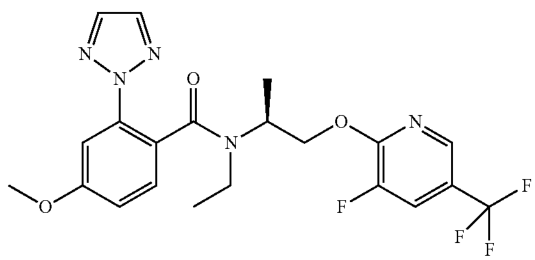 [SMILES: CCN(C(=O)c1ccc(OC)cc1-n1nccn1)[C@@H](C)COc1ncc(C(F)(F)F)cc1F] | 0.89 (0.5 nM) 0.50 (50 nM) | 450 | 506 900 | 11 |
| 110 | 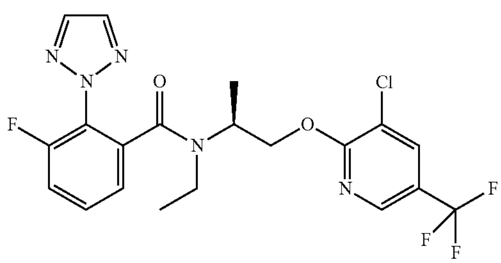 [SMILES: CCN(C(=O)c1cccc(F)c1-n1nccn1)[C@@H](C)COc1ncc(C(F)(F)F)cc1Cl] | 0.17 (50 nM) | 53 | 312 | 100 |
| 111 | 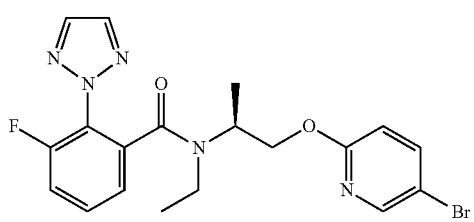 [SMILES: CCN(C(=O)c1cccc(F)c1-n1nccn1)[C@@H](C)COc1ccc(Br)cn1] | 0.40 (0.5 nM) 0.23 (50 nM) | 49 | 123 213 | 62 |
| 112 | 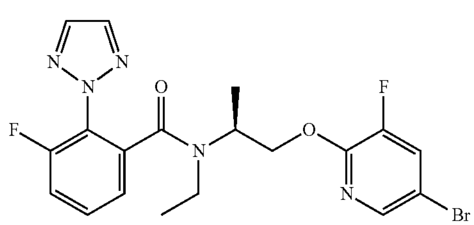 [SMILES: CCN(C(=O)c1cccc(F)c1-n1nccn1)[C@@H](C)COc1ncc(Br)cc1F] | 0.57 (0.5 nM) 0.50 (50 nM) | 96 | 168 192 | 67 |
| 126 | 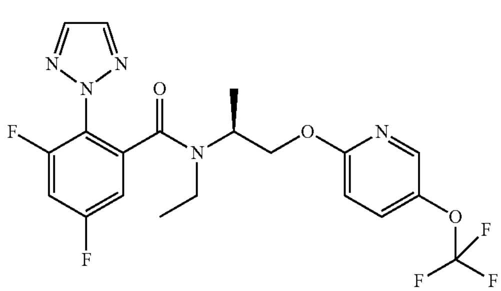 [SMILES: CCN(C(=O)c1cc(F)cc(F)c1-n1nccn1)[C@@H](C)COc1ccc(OC(F)(F)F)cn1] | 0.58 (0.5 nM) 0.62 (50 nM) | 41 | 71 66 | 62 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 134 | 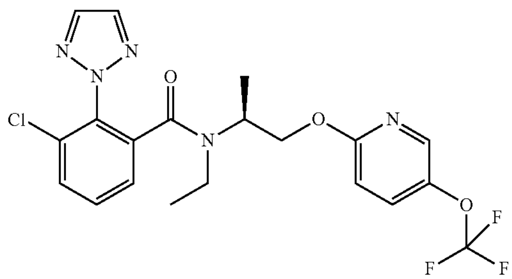 [SMILES: CCN(C(=O)c1cccc(Cl)c1-n1nccn1)[C@@H](C)COc1ccc(OC(F)(F)F)cn1] | 0.14 (50 nM) | 12 | 86 | 64 |
| 133 | 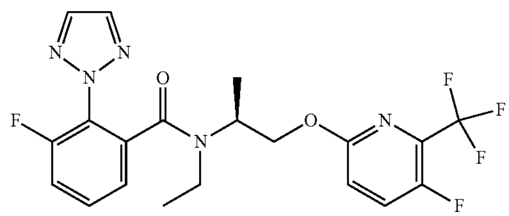 [SMILES: CCN(C(=O)c1cccc(F)c1-n1nccn1)[C@@H](C)COc1ccc(F)c(C(F)(F)F)n1] | 1.6 (0.5 nM) | 101 | 63 | 21 |
| 14 | 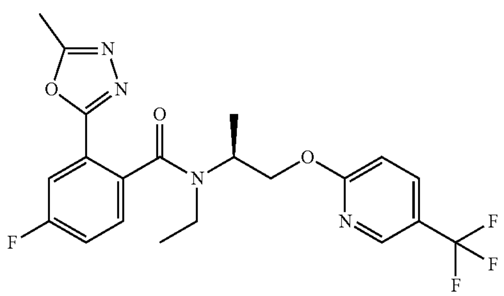 [SMILES: CCN(C(=O)c1ccc(F)cc1-c1nnc(C)o1)[C@@H](C)COc1ccc(C(F)(F)F)cn1] | 4.5 (0.5 nM) | 2073 | 461 | >130 |
| 18 | 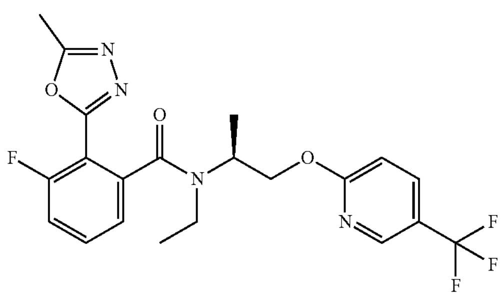 [SMILES: CCN(C(=O)c1cccc(F)c1-c1nnc(C)o1)[C@@H](C)COc1ccc(C(F)(F)F)cn1] | 0.80 (0.5 nM) | 218 | 273 | 74 |
| 20 | 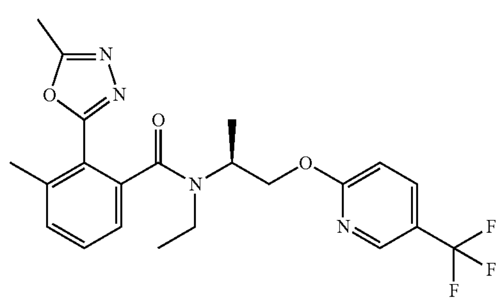 [SMILES: CCN(C(=O)c1cccc(C)c1-c1nnc(C)o1)[C@@H](C)COc1ccc(C(F)(F)F)cn1] | 0.12 (50 nM) | 35 | 292 | 20 |

TABLE 3-continued
Comparison of biological data of the compounds of the present invention with the closest prior art compounds in WO2016/034882
| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 22 | 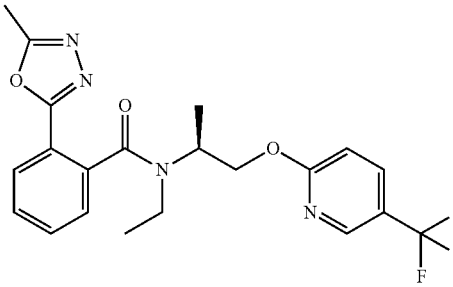 | 0.93 (0.5 nM)<br>1.20 (50 nM) | 202 | 217<br>168 | 84 |
| 74 | 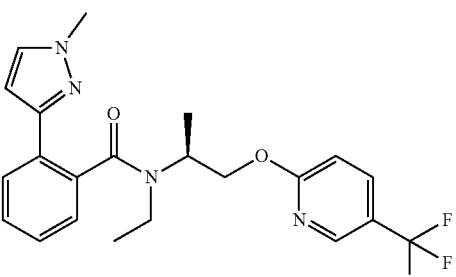 | 0.39 (0.5 nM)<br>0.21 (50 nM) | 48 | 123<br>229 | 14 |
| 93 | 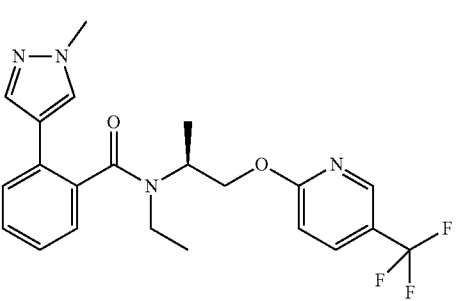 [SMILES: CCN(C(=O)c1ccccc1-c1cnn(C)c1)[C@@H](C)COc1ccc(C(F)(F)F)cn1] | 0.75 (50 nM) | 74 | 99 | 18 |
| 123 | 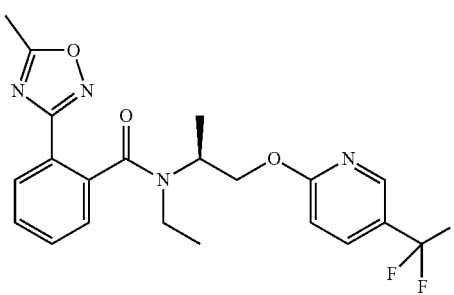 | 0.17 (50 nM) | 34 | 200 | 23 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 55 | 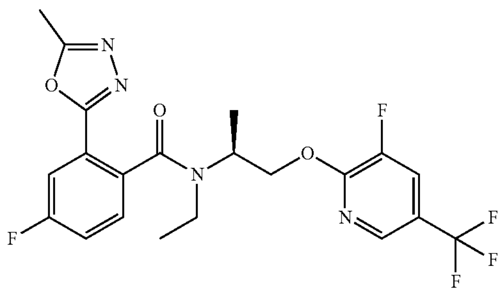 [SMILES: CCN(C(=O)c1ccc(F)cc1-c1nnc(C)o1)[C@@H](C)COc1ncc(C(F)(F)F)cc1F] | 7.2 (0.5 nM) | 3097 | 430 | 64 |
| 61 | 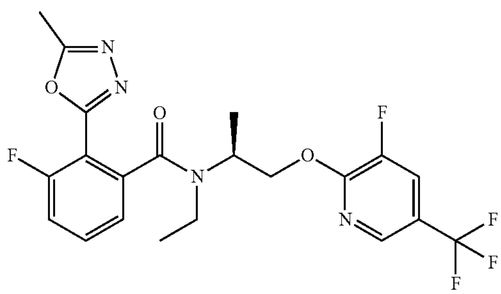 [SMILES: CCN(C(=O)c1cccc(F)c1-c1nnc(C)o1)[C@@H](C)COc1ncc(C(F)(F)F)cc1F] | 3.27 (0.5 nM) | 1478 | 452 | 26 |
| 64 | 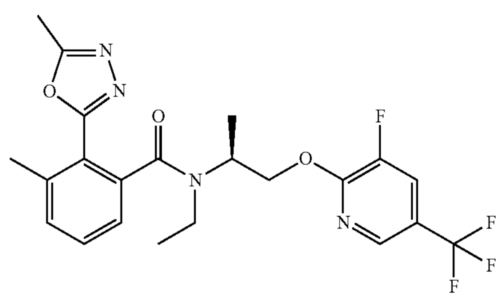 [SMILES: CCN(C(=O)c1cccc(C)c1-c1nnc(C)o1)[C@@H](C)COc1ncc(C(F)(F)F)cc1F] | 0.22 (50 nM) | 155 | 705 | 15 |
| 68 | 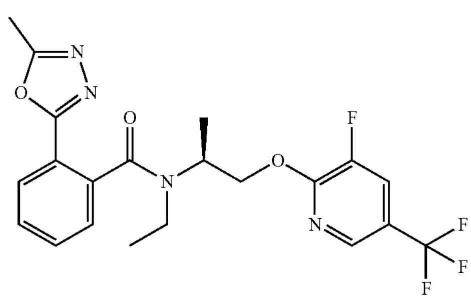 [SMILES: CCN(C(=O)c1ccccc1-c1nnc(C)o1)[C@@H](C)COc1ncc(C(F)(F)F)cc1F] | 1.9 (0.5 nM) | 1001 | 527 | 53 |
| 124 | 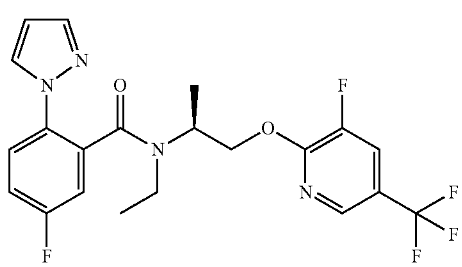 [SMILES: CCN(C(=O)c1cc(F)ccc1-n1cccn1)[C@@H](C)COc1ncc(C(F)(F)F)cc1F] | 3.8 (0.5 nM) | 1058 | 278 | 10 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 132 | 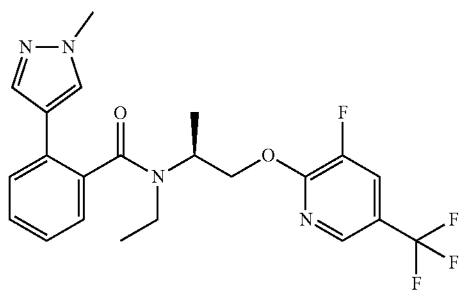 [SMILES: CCN(C(=O)c1ccccc1-c1cnn(C)c1)[C@@H](C)COc1ncc(C(F)(F)F)cc1F] | 1.7 (0.5 nM) | 152 | 89 | 11 |
| 121 | 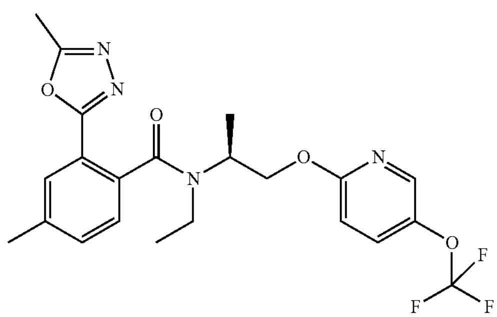 [SMILES: CCN(C(=O)c1ccc(C)cc1-c1nnc(C)o1)[C@@H](C)COc1ccc(OC(F)(F)F)cn1] | 1.4 (0.5 nM)<br>1.5 (50 nM) | 440 | 314<br>293 | 15 |
| Ex 14 in WO2016/034882 | 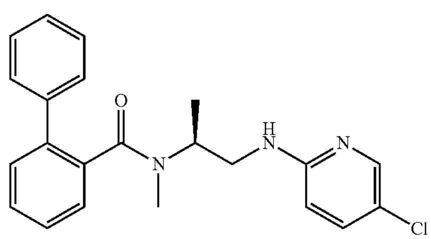 [SMILES: C[C@@H](CNc1ccc(Cl)cn1)N(C)C(=O)c1ccccc1-c1ccccc1] | 0.171 (50 nM) | 4.7 | 27 | 2 |
| 76 | 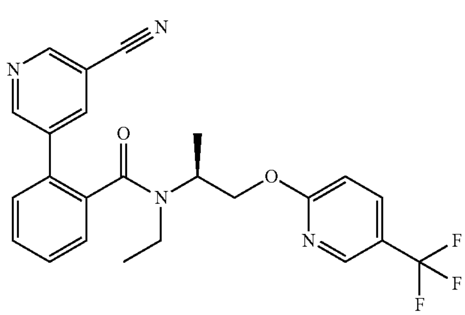 [SMILES: CCN(C(=O)c1ccccc1-c1cncc(C#N)c1)[C@@H](C)COc1ccc(C(F)(F)F)cn1] | 1.1 (0.5 nM)<br>0.99 (50 nM) | 124 | 113<br>125 | 11 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 79 | 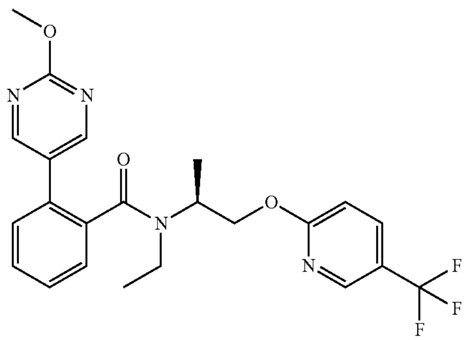 [SMILES: CCN(C(=O)c1ccccc1-c1cnc(OC)nc1)[C@@H](C)COc1ccc(C(F)(F)F)cn1] | 1.4 (0.5 nM) 1.6 (50 nM) | 92 | 66 58 | 12 |
| 81 | 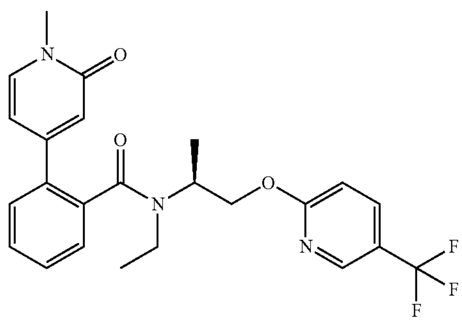 [SMILES: CCN(C(=O)c1ccccc1-c1ccn(C)c(=O)c1)[C@@H](C)COc1ccc(C(F)(F)F)cn1] | 2.9 (0.5 nM) | 1668 | 575 | 39 |
| 84 | 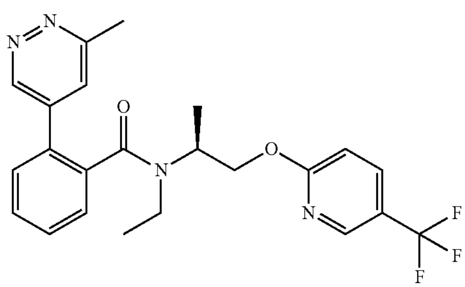 [SMILES: CCN(C(=O)c1ccccc1-c1cnnc(C)c1)[C@@H](C)COc1ccc(C(F)(F)F)cn1] | 8.6 (0.5 nM) | 1290 | 150 | 11 |
| 85 | 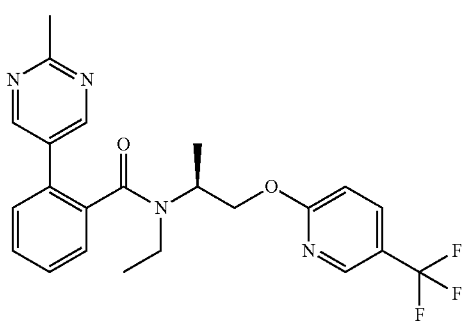 [SMILES: CCN(C(=O)c1ccccc1-c1cnc(C)nc1)[C@@H](C)COc1ccc(C(F)(F)F)cn1] | 8.6 (0.5 nM) | 583 | 68 | 17 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 96 | 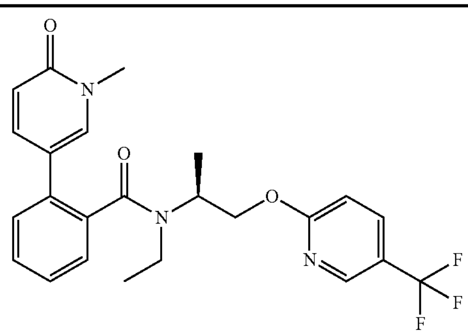 | 7.4 (0.5 nM) | 1607 | 217 | 34 |
| 97 | 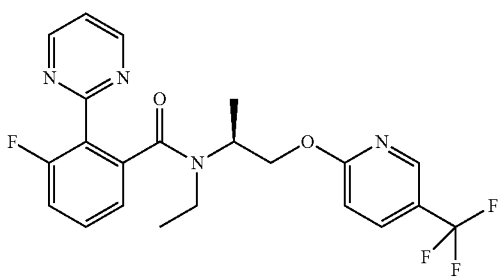 [SMILES: CCN(C(=O)c1cccc(F)c1-c1ncccn1)[C@@H](C)COc1ccc(C(F)(F)F)cn1] | 0.025 (50 nM) | 20 | 800 | 100 |
| 101 | 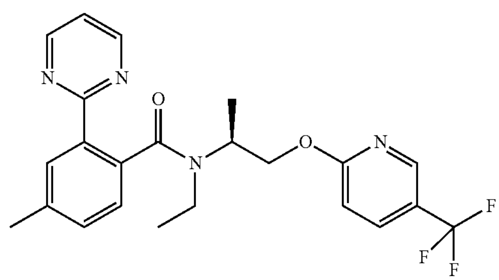 [SMILES: CCN(C(=O)c1ccc(C)cc1-c1ncccn1)[C@@H](C)COc1ccc(C(F)(F)F)cn1] | 0.38 (0.5 nM) | 30 | 79 | 13 |
| 102 | 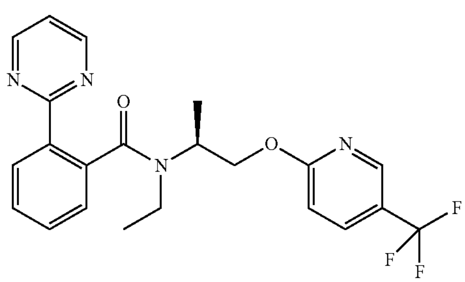 [SMILES: CCN(C(=O)c1ccccc1-c1ncccn1)[C@@H](C)COc1ccc(C(F)(F)F)cn1] | 0.025 (50 nM) | 27.0 | 1080 | 36 |
| 105 | 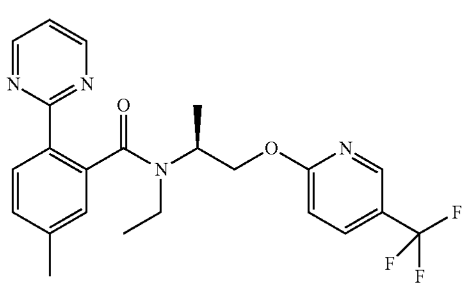 [SMILES: CCN(C(=O)c1cc(C)ccc1-c1ncccn1)[C@@H](C)COc1ccc(C(F)(F)F)cn1] | 0.021 (50 nM) | 11 | 524 | 10 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 107 | 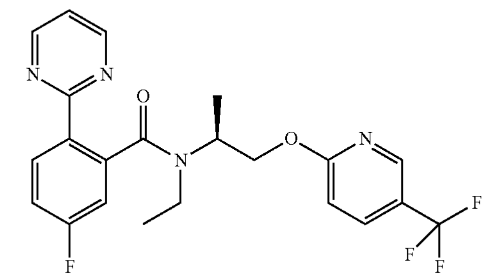 [SMILES: CCN(C(=O)c1cc(F)ccc1-c1ncccn1)[C@@H](C)COc1ccc(C(F)(F)F)cn1] | 0.064 (50 nM) | 32 | 500 | 65 |
| 108 | 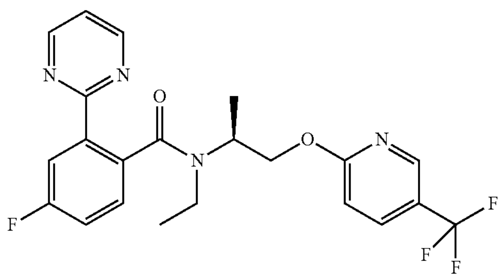 [SMILES: CCN(C(=O)c1ccc(F)cc1-c1ncccn1)[C@@H](C)COc1ccc(C(F)(F)F)cn1] | 0.11 (50 nM) | 45 | 409 | 50 |
| 116 | 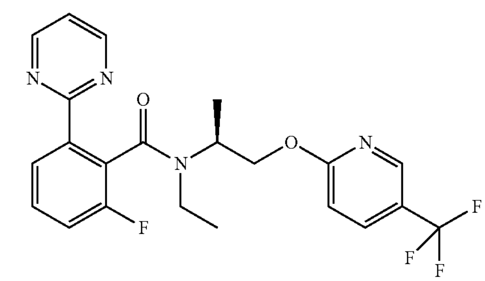 [SMILES: CCN(C(=O)c1c(F)cccc1-c1ncccn1)[C@@H](C)COc1ccc(C(F)(F)F)cn1] | 0.34 (0.5 nM)<br>0.22 (50 nM) | 45 | 132<br>205 | 33 |
| 118 | 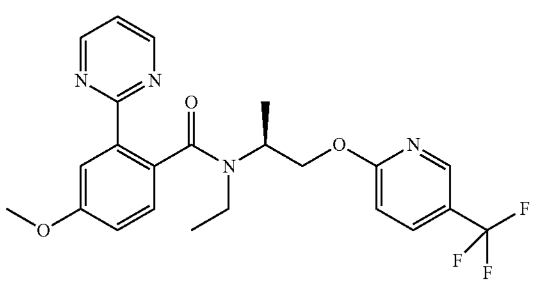 [SMILES: CCN(C(=O)c1ccc(OC)cc1-c1ncccn1)[C@@H](C)COc1ccc(C(F)(F)F)cn1] | 0.032 (50 nM) | 92 | 2875 | 15 |
| 117 | 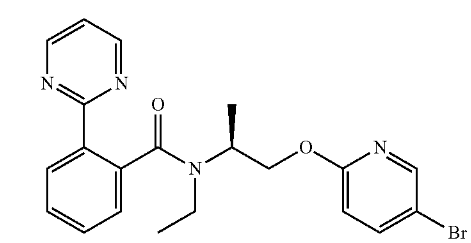 [SMILES: CCN(C(=O)c1ccccc1-c1ncccn1)[C@@H](C)COc1ccc(Br)cn1] | 0.18 (0.5 nM)<br>0.11 (50 nM) | 35 | 194<br>318 | 32 |

TABLE 3-continued

Comparison of biological data of the compounds of the present invention with the closest prior art compounds in WO2016/034882

| Example | Structure | Assay A OX1R Kb [nM] (Orexin A concentration used) | Assay B OX2R Kb [nM] (0.5 nM Orexin A concentration) | OX2R Kb/ OX1R Kb | Assay C: Human MST $t_{1/2}$ [min] |
|---|---|---|---|---|---|
| 120 | 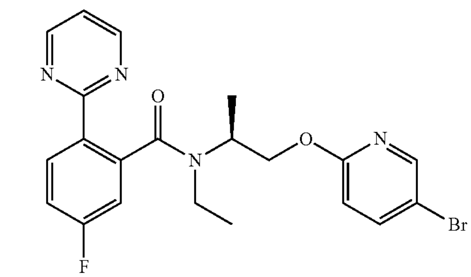 [SMILES: CCN(C(=O)c1cc(F)ccc1-c1ncccn1)[C@@H](C)COc1ccc(Br)cn1] | 0.26 (0.5 nM) 0.12 (50 nM) | 43 | 165 358 | 76 |
| 125 | 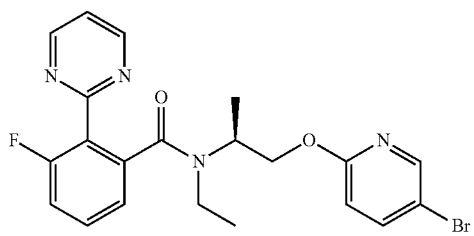 [SMILES: CCN(C(=O)c1cccc(F)c1-c1ncccn1)[C@@H](C)COc1ccc(Br)cn1] | 0.076 (50 nM) | 27 | 355 | >130 |
| 129 | 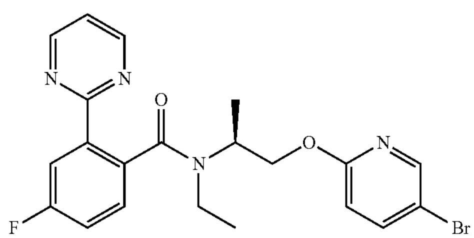 [SMILES: CCN(C(=O)c1ccc(F)cc1-c1ncccn1)[C@@H](C)COc1ccc(Br)cn1] | 0.17 (50 nM) | 42 | 247 | 30 |
| 130 | 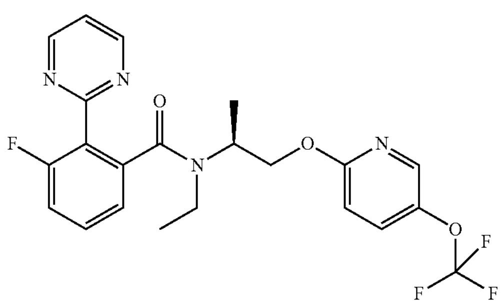 [SMILES: CCN(C(=O)c1cccc(F)c1-c1ncccn1)[C@@H](C)COc1ccc(OC(F)(F)F)cn1] | 0.15 (50 nM) | 20 | 133 | >130 |

Use in Treatment/Method of Use

The present invention is directed to compounds which are useful in the treatment of a disease, disorder and condition wherein the antagonisms of OX1R is of therapeutic benefit, including but not limited to the treatment and/or prevention of psychiatric and neurological conditions associated with impulse control deficits. Such impulse control deficits are seen in addictions including substance use disorders; personality disorders such as borderline personality disorder; eating disorders such as binge eating disorder; or attention deficit hyperactivity disorder. According to a further aspect of the invention, compounds of the present invention are useful in the treatment of OX1R related pathophysiological disturbances in arousal/wakefulness, appetite/food intake, cognition, motivated behaviours/reward, mood and stress.

In view of their pharmacological effect, compounds of the present invention are suitable for use in the treatment of a disease or condition selected from the list consisting of (1) treatment or prevention of substance abuse/dependence/seeking or addiction as well as relapse prevention (including but not limited to drugs, such as cocaine, opiates such as morphine, barbiturates, benzodiazepines, amphetamines, nicotine/tobacco and other psychostimulants), alcoholism and alcohol-related disorders, drug abuse or addiction or relapse, tolerance to narcotics or withdrawal from narcotics, (2) eating disorders, such as binge eating, bulimia nervosa, anorexia nervosa, other specified feeding or eating disorders, obesity, overweight, cachexia, appetite/taste disorders, vomiting, nausea, Prader-Willi-Syndrome, hyperphagia, appetite/taste disorders, (3) attention deficit hyperactivity disorder, conduct disorders, attention problems and related disorders, sleep disorders, anxiety disorders such as generalized anxiety disorder, panic disorder, phobias, post-traumatic stress disorder, schizophrenia, Alzheimer's disease, Parkinson's disease, Huntington's disease and Gilles de la Tourette's syndrome, restless legs syndrome, dementia, dyskinesia, severe mental retardation, neurodegenerative disorders including nosological entities such as disinhibition-dementia-parkinsonism-amyotrophy complex, pallido-ponto-nigral degeneration, (4) cognitive dysfunction in psychiatric or neurological disorder, cognitive impairments associated with schizophrenia, Alzheimer's disease and other neurological and psychiatric disorders, (5) mood disorders, bipolar disorder, mania, depression, manic depression, borderline personality disorder, antisocial personality disorder, aggression such as impulsive aggression, suicidality, frontotemporal dementia, obsessive compulsive disorder, delirium, affective neurosis/disorder, depressive neurosis/disorder, anxiety neurosis, dysthymic disorder, (6) sexual disorder, sexual dysfunction, psychosexual disorder, (7) impulse control disorders such as pathological gambling, trichotillomania, intermittent explosive disorder, kleptomania, pyromania, compulsive shopping, internet addiction, sexual compulsion, (8) sleep disorders such as narcolepsy, jetlag, sleep apnea, insomnia, parasomnia, disturbed biological and circadian rhythms, sleep disturbances associated with psychiatric and neurological disorders, (9) treatment, prevention and relapse control of impulsivity and/or impulse control deficits and/or behavioural disinhibition in any psychiatric and/or neurological condition,

(10) personality disorders such as borderline personality disorder, antisocial personality disorder, paranoid personality disorder, schizoid and schizotypal personality disorder, histrionic personality disorder, narcissistic personality disorder, avoidant personality disorder, dependent personality disorder, other specified and non-specified personality disorders

(11) neurological diseases, such as cerebral oedema and angioedema, cerebral dementia like e.g. Parkinson's and Alzheimer's disease, senile dementia; multiple sclerosis, epilepsy, temporal lobe epilepsy, drug resistant epilepsy, seizure disorders, stroke, myasthenia gravis, brain and meningeal infections like encephalomyelitis, meningitis, HIV as well as schizophrenia, delusional disorders, autism, affective disorders and tic disorders.

The applicable daily dose of compounds of the present invention may vary from 0.1 to 2000 mg. The actual pharmaceutically effective amount or therapeutic dose will depend on factors known by those skilled in the art such as age and weight of the patient, route of administration and severity of disease. In any case, the drug substance is to be administered at a dose and in a manner which allows a pharmaceutically effective amount to be delivered that is appropriate to the patient's condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Combination Therapy

Compounds according to the present invention can be combined with other treatment options known to be used in the art in connection with a treatment of any of the indications the treatment of which is in the focus of the present invention.

Among such treatment options that are considered suitable for combination with the treatment according to the present inventions are:
Antidepressants
Mood stabilizers
Antipsychotics
Anxiolytics
Antiepileptic drugs
Sleeping agents
Cognitive enhancer
Stimulants
Non-stimulant medication for attention deficit hyperactivity disorder
Additional psychoactive drugs.

General Synthetic Methods

The invention also provides a process for making compounds of Formula (I). Unless specified otherwise, $R^1$, $R^2$, $R^3$, $R^4$, $R^5$, $R^6$, $R^7$ and Ar in the formulas below shall have the meaning as defined for formula I in the detailed description of the invention above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), liquid chromatography-mass spectrometry (LC-MS) if desired, and intermediates and products may be purified by chromatography and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Compounds of Formula (I) can be synthesized by the method illustrated in Scheme 1:

Scheme 1

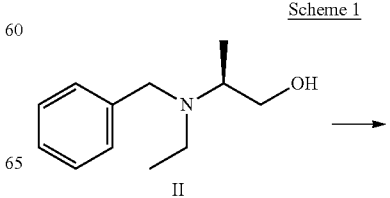

II

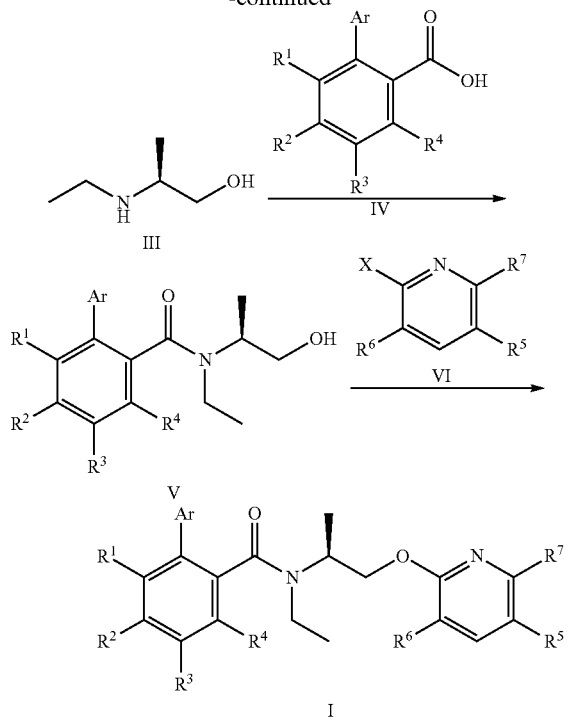

Alternatively, a compound of formula I can be synthesized as illustrated in Scheme 2:

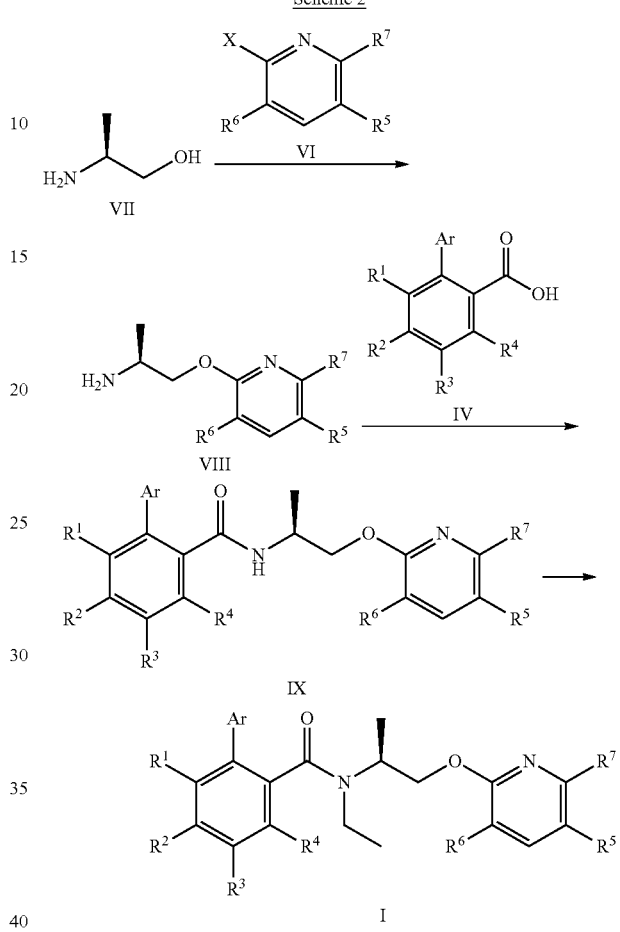

Debenzylation reactions are described in 'Protective Groups in Organic Synthesis', 3' edition, T. W. Greene and P. G. M. Wuts, Wiley-Interscience (1999). Debenzylation of compound II in a suitable solvent such as MeOH, under a pressure of hydrogen in the presence of a suitable catalyst such as Pd/C results in a secondary amine of formula III.

Peptide coupling reactions known to the person skilled in the art (see for example M. Bodanszky, 1984, The Practice of Peptide Synthesis, Springer-Verlag) can be applied to react the secondary amine of formula III with a carboxylic acid of formula IV to yield a compound of formula V. For example, carboxylic acid IV in a suitable solvent such as DCM, DMF and toluene, upon treatment with thionyl chloride or oxalyl chloride yields an acid chloride which is then treated with an amine of formula III, in a suitable solvent such as DCM and THF, in the presence of a suitable base such as TEA, to provide a compound of formula V. Other peptide coupling reagents such as HATU, in a suitable solvent such as DMF and in the presence of a suitable base such as DIPEA may be used.

Reacting the alcohol of formula V with a halo pyridine VI (X=halide) in a nucleophilic aromatic substitution reaction, in a suitable solvent such as dioxane, DMSO or DMF and in the presence of a suitable base such as potassium tert-butoxide or NaH, provides a compound of formula I. Alternatively, the alcohol of formula V can be reacted with hydroxypyridine of formula VI (X=OH) in a Mitsunobu reaction in the presence of diethylazodicarboxylate (DEAD) or diisopropy-lazodicarboxylate (DIAD) and in the presence of triphenylphosphine to provide a compound of formula I.

Compounds of formula I, in which $R^5$ is Br, can be further reacted in a Suzuki-type cross-coupling reaction with a cyclopropyltrifluoroborate salt in a suitable solvent such toluene/water, in the presence of a suitable catalyst such as palladium(II) acetate and a suitable ligand such as tricyclohexylphosphine to a compound of formula I in which $R^5$ is cyclopropyl.

Reacting the alcohol of formula VII with a halo pyridine VI (X=halide) in a nucleophilic aromatic substitution reaction, in a suitable solvent such as dioxane or DMF and in the presence of a suitable base such as potassium tert-butoxide or NaH, provides a primary amine of formula VIII. Peptide coupling reactions known to the person skilled in the art (see for example M. Bodanszky, 1984, The Practice of Peptide Synthesis, Springer-Verlag) can be applied to react a secondary amine of formula VIII with a carboxylic acid of formula IV to yield a compound of formula IX. For example, a peptide coupling reagents such as TBTU or HATU in a suitable solvent such as DMF in the presence of a suitable base such as DIPEA may be used. Alkylation of amide IX using a suitable alkylation agent such as ethyl iodide in a suitable solvent such as DMF and a suitable base such as potassium tert-butoxide or NaH yields a compound of formula I.

Compounds of formula I, in which $R^5$ is Br, can be further reacted in a Suzuki-type cross-coupling reaction with a cyclopropyltrifluoroborate salt in a suitable solvent such toluene/water, in the presence of a suitable catalyst such as palladium(II) acetate and a suitable ligand such as tricyclohexylphosphine to a compound of formula I in which $R^5$ is cyclopropyl.

Alternatively, a compound of formula I can be synthesized as illustrated in Scheme 3:

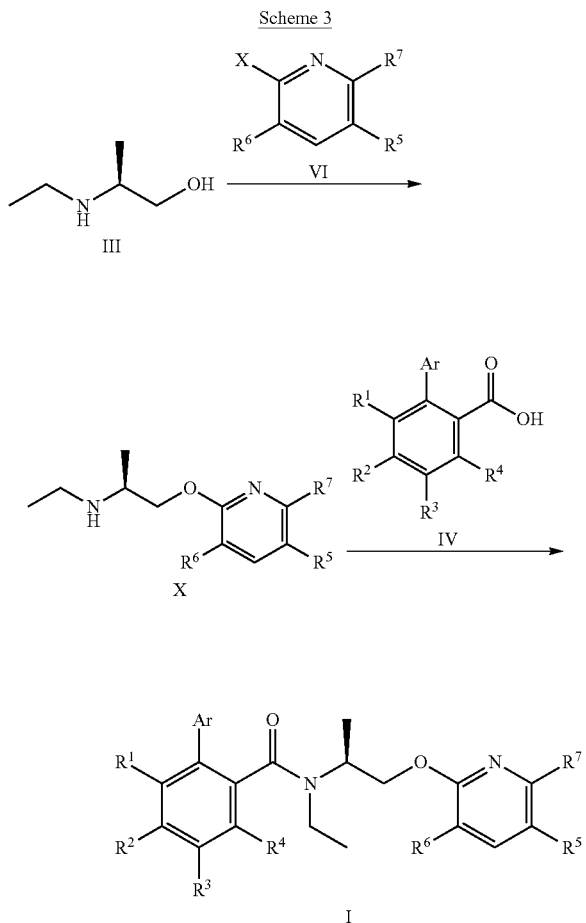

Reacting the alcohol of formula III with a halo pyridine VI (X=halide) in a nucleophilic aromatic substitution reaction, in a suitable solvent such as dioxane, DMSO or DMF and in the presence of a suitable base such as potassium tert-butoxide or NaH, provides a secondary amine of formula X. Peptide coupling reactions known to the person skilled in the art (see for example M. Bodanszky, 1984, The Practice of Peptide Synthesis, Springer-Verlag) can be applied to react the secondary amine of formula X with a carboxylic acid of formula IV to yield a compound of formula I. For example, amine X and carboxylic acid IV in a suitable solvent such as acetonitrile or DMF in the presence of a base such as DIPEA yields upon treatment with the coupling agent 2-chloro-4,5-dihydro-1,3-dimethyl-1H-imidazolium hexafluorophosphate (CIP) or 1-[bis(dimethylamino)methylene]-1H-1,2,3-triazolo[4,5-b]pyridinium 3-oxid hexafluorophosphate (HATU) a compound of formula I.

Compounds of formula I, in which $R^5$ is Br, can be further reacted in a Suzuki-type cross-coupling reaction with a cyclopropyltrifluoroborate salt in a suitable solvent such toluene/water, in the presence of a suitable catalyst such as palladium(II) acetate and a suitable ligand such as tricyclohexylphosphine to a compound of formula I in which $R^5$ is cyclopropyl.

Alternatively, a compound of formula I can be synthesized as illustrated in Scheme 4:

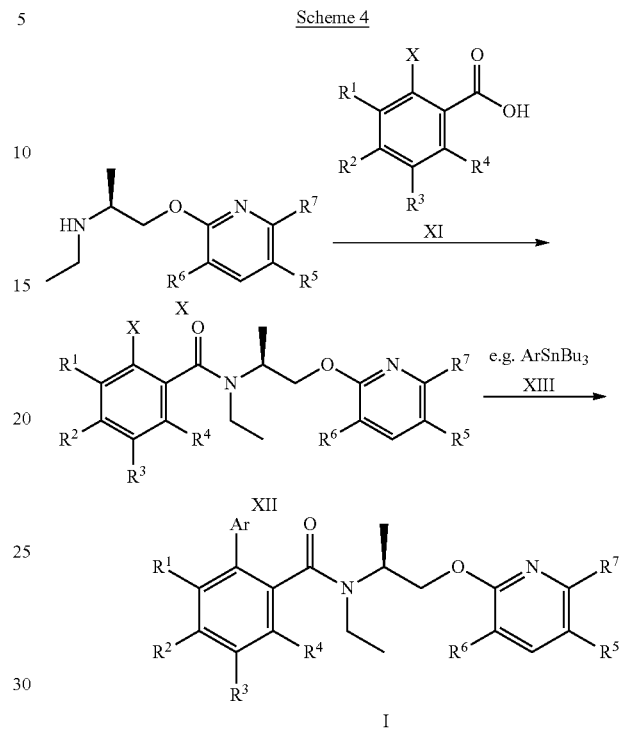

Peptide coupling reactions known to the person skilled in the art (see for example M. Bodanszky, 1984, The Practice of Peptide Synthesis, Springer-Verlag) can be applied to react a secondary amine of formula VIII with a carboxylic acid of formula XI, in which X=halogen, to yield a compound of formula XII. For example, a peptide coupling reagents such as TBTU, CIP or HATU in a suitable solvent such as acetonitrile or DMF in the presence of a suitable base such as DIPEA may be used. Reacting the amide of formula XII in a Stille reaction with an aryl tributyltin of formula XIII in a suitable solvent such as DME in the presence of a suitable catalyst such as Pd(PPh$_3$)$_4$ and in the presence of CuI yields a compound of formula I. Alternatively, the amide of formula XII can be reacted in a Suzuki reaction in a suitable solvent such system as dioxane and water, in the presence of a suitable catalyst such as Pd(dppf)Cl$_2$.DCM and in the presence of a suitable base such as K$_2$OO$_3$ to provide a compound of formula I.

Alternatively, an alcohol of formula X can be synthesized as illustrated in Scheme 5:

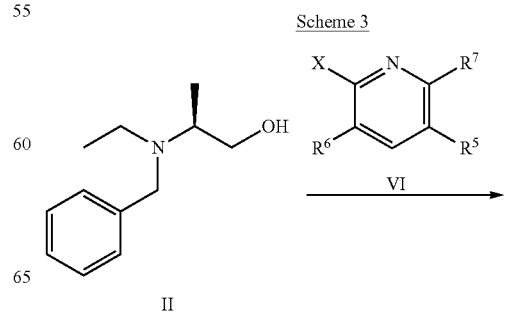

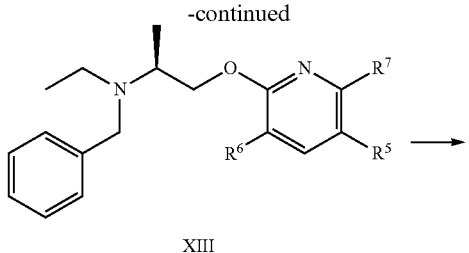

XIII

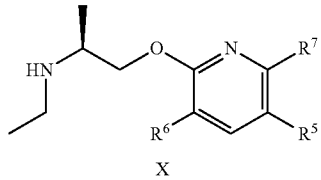

X

Reacting the alcohol of formula II with a halo pyridine VI (X=halide) in a nucleophilic aromatic substitution reaction, in a suitable solvent such as dioxane, DMSO or DMF and in the presence of a suitable base such as potassium tert-butoxide or NaH, provides a secondary amine of formula XIII. Debenzylation reactions are described in 'Protective Groups in Organic Synthesis', 3' edition, T. W. Greene and P. G. M. Wuts, Wiley-Interscience (1999). Debenzylation of compound II in a suitable solvent such as MeOH, under a pressure of hydrogen in the presence of a suitable catalyst such as Pd/C results in a secondary amine of formula X.

Intermediate carboxylic acids V are commercially available or they can be synthesized according or in analogy to methods described in the literature.

EXPERIMENTAL SECTION

List of Abbreviations
RT room temperature
CIP 2-chloro-4,5-dihydro-1,3-dimethyl-1H-imidazolium hexafluorophosphate
dppf 1,1'-bis(diphenylphosphanyl)ferrocene
ESI-MS electrospray ionisation mass spectrometry
aq. aqueous
MS mass spectrum
MeOH methanol
EtOH ethanol
EA ethyl acetate
DMF N,N-dimethylformamide
DME 1,2-dimethoxyethane
DMSO dimethylsulfoxide
DCM dichloromethane
THF tetrahydrofuran
Me-THF methyl-tetrahydrofuran
DIPEA N,N-diisopropylethylamine
HATU 1-[bis(dimethylamino)methylene]-1H-1,2,3-triazolo[4,5-b]pyridinium 3-oxid hexafluorophosphate
TBTU 0-(benzotriazol-1-yl)-N,N,N,N'-tetramethyl-uronium tetrafluoroborate
Rt retention time
h hour(s)
min minutes
sat. saturated
TEA triethylamine
ACN acetonitrile
TFA trifluoroacetic acid
M molarity
N normality
HPLC high-performance liquid chromatography
HPLC-MS high-performance liquid chromatography-mass spectrometry
LC-MS liquid chromatography-mass spectrometry
TLC thin layer chromatography
DIAD diisopropyl azodicarboxylate
DEAD diethyl azodicarboxylate HPLC-Methods:

| Method Name: | A |
| Column: | Venusil XBP-C18, 2.1 × 50 mm, 5 μm |
| Column Supplier: | Agela Technologies |

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 90 | 10 | 0.8 | 50 |
| 0.40 | 90 | 10 | 0.8 | 50 |
| 3.40 | 0 | 100 | 0.8 | 50 |
| 3.85 | 0 | 100 | 0.8 | 50 |
| 3.86 | 90 | 10 | 0.8 | 50 |
| 4.50 | 90 | 10 | 0.8 | 50 |

| Method Name: | B |
| Column: | Sunfire C18, 2.1 × 30 mm, 2.5 μm |
| Column Supplier: | Waters |

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

| Method Name: | C |
| Column: | Chromolith Flash RP-18e 25-2 mm |
| Column Supplier: | Merck |

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 95 | 5 | 1.5 | 40 |
| 0.70 | 5 | 95 | 1.5 | 40 |
| 1.15 | 5 | 95 | 1.5 | 40 |
| 1.16 | 95 | 5 | 1.5 | 40 |
| 1.60 | 5 | 95 | 1.5 | 40 |

| Method Name: | D |
| Column: | XBridge BEH Phenyl, 2.1 × 30 mm, 1.7 μm |
| Column Supplier: | Waters |

| Gradient/Solvent Time [min] | % Sol [H$_2$O, 0.1% NH$_3$] | % Sol [ACN] | Flow [mL/min] | Temp [° C.] |
|---|---|---|---|---|
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | E |
| --- | --- |
| Column: | XBridge C18, 4.6 × 30 mm, 3.5 μm |
| Column Supplier: | Waters |

| Gradient/Solvent Time [min] | % Sol [H₂O, 0.1% NH₃] | % Sol [ACN] | Flow [mL/min] | Temp [° C.] |
| --- | --- | --- | --- | --- |
| 0.00 | 97 | 3 | 5 | 60 |
| 0.02 | 97 | 3 | 5 | 60 |
| 1.60 | 0 | 100 | 5 | 60 |
| 1.70 | 0 | 100 | 5 | 60 |

| Method Name: | F |
| --- | --- |
| Column: | XBridge C18, 3 × 30 mm, 2.5 μm |
| Column Supplier: | Waters |

| Gradient/Solvent Time [min] | % Sol [H₂O, 0.1% NH₃] | % Sol [ACN] | Flow [mL/min] | Temp [° C.] |
| --- | --- | --- | --- | --- |
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | G |
| --- | --- |
| Column: | Sunfire, 3 × 30 mm, 2.5 μm |
| Column Supplier: | Waters |

| Gradient/Solvent Time [min] | % Sol [H₂O, 0.1% TFA] | % Sol [ACN] | Flow [mL/min] | Temp [° C.] |
| --- | --- | --- | --- | --- |
| 0.00 | 97 | 3 | 2.2 | 60 |
| 0.02 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method Name: | H |
| --- | --- |
| Column: | Sunfire C18, 2.1 × 30 mm, 2.5 μm |
| Column Supplier: | Waters |

| Gradient/Solvent Time [min] | % Sol [H₂O, 0.1% TFA] | % Sol [ACN] | Flow [mL/min] | Temp [° C.] |
| --- | --- | --- | --- | --- |
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

| Method Name: | I |
| --- | --- |
| Column: | Venusil XBP-C18, 2.1 × 50 mm, 5 μm |
| Column Supplier: | Agilent |

| Gradient/Solvent Time [min] | % Sol [H₂O, 0.0375% TFA] | % Sol [ACN, 0.018% TFA] | Flow [mL/min] | Temp [° C.] |
| --- | --- | --- | --- | --- |
| 0.00 | 100 | 0 | 1.0 | 50 |
| 0.30 | 100 | 0 | 1.0 | 50 |
| 2.10 | 40 | 60 | 1.0 | 50 |
| 2.48 | 40 | 60 | 1.0 | 50 |
| 2.50 | 100 | 0 | 1.0 | 50 |
| 3.00 | 100 | 0 | 1.0 | 50 |

| Method Name: | J |
| --- | --- |
| Column: | XBridge BEH C18, 2.1 × 30 mm, 1.7 μm |
| Column Supplier: | Waters |

| Gradient/Solvent Time [min] | % Sol [H₂O, 0.1% TFA] | % Sol [ACN] | Flow [mL/min] | Temp [° C.] |
| --- | --- | --- | --- | --- |
| 0.00 | 99 | 1 | 1.6 | 60 |
| 0.02 | 99 | 1 | 1.6 | 60 |
| 1.00 | 0 | 100 | 1.6 | 60 |
| 1.10 | 0 | 100 | 1.6 | 60 |

| Method Name: | K |
| --- | --- |
| Column: | Zorbax Eclipse XDB-C18, 4.6 × 50 mm, 3.5 μm |
| Column Supplier: | Waters |

| Gradient/Solvent Time [min] | % Sol [90% H₂O + 10% ACN + NH₄COOH 5 mM] | % Sol [90% ACN + 10% H₂O] | Flow [mL/min] | Temp [° C.] |
| --- | --- | --- | --- | --- |
| 0.00 | 100 | 0 | 1.3 | 35 |
| 4.50 | 0 | 100 | 1.3 | 35 |
| 5.80 | 0 | 100 | 1.3 | 35 |
| 6.00 | 100 | 0 | 1.3 | 35 |

| Method Name: | L |
| --- | --- |
| Column: | XBridge BEH C18, 2.1 × 30 mm, 1.7 μm |
| Column Supplier: | Waters |

| Gradient/Solvent Time [min] | % Sol [H₂O, 0.1% NH₃] | % Sol [ACN] | Flow [mL/min] | Temp [° C.] |
| --- | --- | --- | --- | --- |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

| Method Name: | M |
| --- | --- |
| Column: | BEH C18 1.7 μm 2.1 × 50 mm |
| Column Supplier: | Waters |

| Gradient/Solvent Time [min] | % Sol [90% ACN + NH₄COOH 5 mM] | % Sol [90% ACN + 10% H₂O] | Flow [mL/min] | Temp [° C.] |
| --- | --- | --- | --- | --- |
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

| Method Name: | N |
|---|---|
| Column: | Xselect CSH, 2.5 µm, 4.6 × 50 mm |
| Column Supplier: | Waters |

| Gradient/Solvent Time [min] | % Sol [90% H$_2$O + 10% ACN + 0.1% HCOOH] | % Sol [90% ACN + 10% H$_2$O + 0.1% HCOOH] | Flow [mL/min] | Temp [° C.] |
|---|---|---|---|---|
| 0.00 | 100 | 0 | 1.4 | RT |
| 4.00 | 0 | 100 | 1.4 | RT |
| 5.30 | 0 | 100 | 1.4 | RT |
| 5.50 | 100 | 0 | 1.4 | RT |
| 6.00 | 100 | 0 | 1.4 | RT |

| Method Name: | O |
|---|---|
| Column: | Synergi Hydro RP100A, 2.5 µm, 3 × 50 mm |
| Column Supplier: | Phenomenex |

| Gradient/Solvent Time [min] | % Sol [90% H$_2$O + 10% ACN + 5 mM NH$_4$COOH] | % Sol [90% ACN + 10% H$_2$O] | Flow [mL/min] | Temp [° C.] |
|---|---|---|---|---|
| 0.00 | 100 | 0 | 1.2 | RT |
| 4.00 | 0 | 100 | 1.2 | RT |
| 5.30 | 0 | 100 | 1.2 | RT |
| 5.50 | 100 | 0 | 1.2 | RT |
| 6.00 | 100 | 0 | 1.2 | RT |

| Method Name: | P |
|---|---|
| Column: | Sunfire C18, 3.0 × 30 mm, 3.5 µm |
| Column Supplier: | Waters |

| Gradient/Solvent Time [min] | % Sol [H$_2$O, 0.1 TFA] | % Sol [ACN] | Flow [mL/min] | Temp [° C.] |
|---|---|---|---|---|
| 0.0 | 98 | 2 | 2.0 | 60 |
| 0.3 | 98 | 2 | 2.0 | 60 |
| 1.5 | 0 | 100 | 2.0 | 60 |
| 1.6 | 0 | 100 | 2.0 | 60 |

| Method Name: | Q |
|---|---|
| Column: | XBridge BEH C18, 2.1 × 30 mm, 1.7 µm |
| Column Supplier: | Waters |

| Gradient/Solvent Time [min] | % Sol [H$_2$O, 0.1% TFA] | % Sol [ACN] | Flow [mL/min] | Temp [° C.] |
|---|---|---|---|---|
| 0.00 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

| Method Name: | R |
|---|---|
| Column: | Sunfire C18, 3.0 × 30 mm, 2.5 µm |
| Column Supplier: | Waters |

| Gradient/Solvent Time [min] | % Sol [ACN 0.08% TFA] | Flow [mL/min] | Temp [° C.] |
|---|---|---|---|
| 0.0 | 5.0 | 1.5 | 40 |
| 1.3 | 100.0 | 1.5 | 40 |
| 1.5 | 100.0 | 1.5 | 40 |
| 1.6 | 5.0 | 1.5 | 40 |

| Method Name: | S |
|---|---|
| Column: | XBridge C18_3.0 × 30 mm_2.5 µm |
| Column Supplier: | Waters |

| Gradient/Solvent Time [min] | % Sol [H$_2$O, 0.1% NH$_3$] | % Sol [ACN] | Flow [mL/min] | Temp [° C.] |
|---|---|---|---|---|
| 0.0 | 95.0 | 5.0 | 1.5 | 40 |
| 1.3 | 0.0 | 100.0 | 1.5 | 40 |
| 1.5 | 0.0 | 100.0 | 1.5 | 40 |
| 1.6 | 95.0 | 5.0 | 1.5 | 40 |

| Method Name: | T |
|---|---|
| Column: | Sunfire C18_3.0 × 30 mm_2.5 µm |
| Column Supplier: | Waters |

| Gradient/Solvent Time [min] | % Sol [H$_2$O, 0.1% TFA (v/v)] | % Sol [ACN] | Flow [mL/min] | Temp [° C.] |
|---|---|---|---|---|
| 0.0 | 98.0 | 2.0 | 2.0 | 60 |
| 1.2 | 0.0 | 100.0 | 2.0 | 60 |
| 1.4 | 0.0 | 100.0 | 2.0 | 60 |

| Method Name: | U |
|---|---|
| Column: | BEH C18, 1.7 µm, 2.1 × 50 mm |
| Column Supplier: | Waters |

| Gradient/Solvent Time [min] | % Sol [90% H$_2$O + 10% ACN + 5 nM NH$_4$HCO$_3$] | % Sol [90% ACN + 10% H$_2$O] | Flow [mL/min] | Temp [° C.] |
|---|---|---|---|---|
| 0.00 | 100 | 0 | 0.7 | 35 |
| 1.20 | 0 | 100 | 0.7 | 35 |
| 1.45 | 0 | 100 | 0.7 | 35 |
| 1.55 | 100 | 0 | 0.7 | 35 |
| 1.75 | 100 | 0 | 0.7 | 35 |

| Method Name: | V |
|---|---|
| Column: | Sunfire C18_3.0 × 30 mm_2.5 µm |
| Column Supplier: | Waters |

| Gradient/Solvent Time [min] | % Sol [H$_2$O, 0.1% TFA] | % Sol [ACN, 0.08% TFA] | Flow [mL/min] | Temp [° C.] |
|---|---|---|---|---|
| 0.00 | 95 | 5 | 1.5 | 60 |
| 1.30 | 100 | 0 | 1.5 | 60 |
| 1.50 | 100 | 0 | 1.5 | 60 |
| 1.60 | 95 | 5 | 1.5 | 60 |

| Method Name: | X |
|---|---|
| Column: | Luna-C18 5 µm, 2.0 * 50 mm |
| Column Supplier: | Phenomenex |

| Gradient/Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 99 | 1 | 0.8 | 40 |
| 0.40 | 99 | 1 | 0.8 | 40 |
| 3.40 | 0 | 100 | 0.8 | 40 |
| 3.85 | 0 | 100 | 0.8 | 40 |
| 3.86 | 99 | 1 | 0.8 | 40 |
| 4.50 | 99 | 1 | 0.8 | 40 |

| Method Name: | Z | | | |
|---|---|---|---|---|
| Column: | Venusil XBP-C18, 2.1 × 50 mm, 5 μm | | | |
| Column Supplier: | Agilent | | | |

| Gradient/ Solvent Time [min] | % Sol [H$_2$O, 0.0375% TFA] | % Sol [ACN, 0.018% TFA] | Flow [mL/min] | Temp [° C.] |
|---|---|---|---|---|
| 0.00 | 90 | 10 | 1.0 | 50 |
| 2.00 | 20 | 80 | 1.0 | 50 |
| 2.48 | 20 | 80 | 1.0 | 50 |
| 2.50 | 90 | 10 | 1.0 | 50 |
| 3.00 | 90 | 10 | 1.0 | 50 |

Preparation of Intermediates

Acids

| Intermediate | Name | Structure | Synthesis for Patent drafting |
|---|---|---|---|
| A-1 | 2-[1,2,3]Triazol-2-yl-benzoic acid | 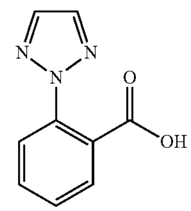 [SMILES: O=C(O)c1ccccc1-n1nccn1] | commercially available from Emolecules catalog number 43677820, MDL number: MFCD20486491 |
| A-2 | 5-Methyl-2-[1,2,3]triazol-2-yl-benzoic acid | 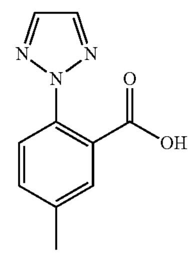 | commercially available from Fluorochem catalog number 244843, MDL number: MFCD18382679 |
| A-3 | 4-Methyl-2-[1,2,3]triazol-2-yl-benzoic acid | 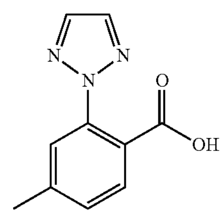 | WO2013/50938, Page 62, Intermediate B1.17 |
| A-4 | 3-Methyl-2-[1,2,3]triazol-2-yl-benzoic acid | 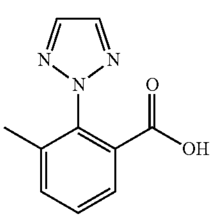 | WO2011/50200, Pages 68-69, Intermediate 37 |
| A-5 | 4,5-Dimethyl-2-[1,2,3]triazol-2-yl-benzoic acid | 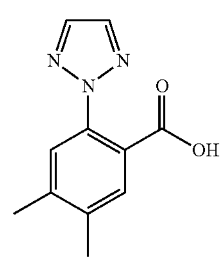 [SMILES: Cc1cc(C(=O)O)c(-n2nccn2)cc1C] | WO2013/50938, Page 61, Intermediate B1.14 |

-continued

| Intermediate | Name | Structure | Synthesis for Patent drafting |
|---|---|---|---|
| A-6 | 3,4-Dimethyl-2-[1,2,3]triazol-2-yl-benzoic acid | 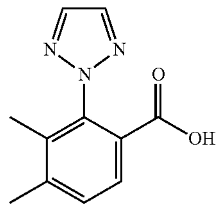 [SMILES: Cc1ccc(C(=O)O)c(-n2nccn2)c1C] | WO2013/68935, Page 58; Intermediate E-20 |
| A-7 | 3-Fluoro-2-[1,2,3]triazol-2-yl-benzoic acid | 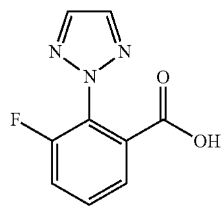 [SMILES: O=C(O)c1cccc(F)c1-n1nccn1] | WO2011/50198, Page 47, Intermediate 5 |
| A-8 | 4-Chloro-2-[1,2,3]triazol-2-yl-benzoic acid | 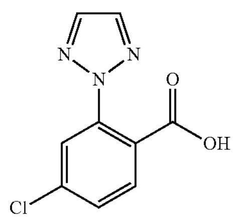 [SMILES: O=C(O)c1ccc(Cl)cc1-n1nccn1] | WO2011/50198, Page 47, Intermediate 6 |
| A-9 | 4-Fluoro-2-[1,2,3]triazol-2-yl-benzoic acid | 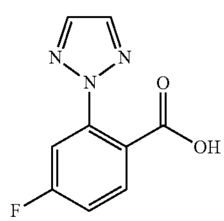 [SMILES: O=C(O)c1ccc(F)cc1-n1nccn1] | WO2011/50200, Page 54, Intermediate 16 |
| A-10 | 3,5-Dimethyl-2-[1,2,3]triazol-2-yl-benzoic acid | 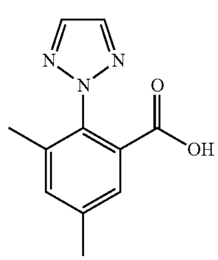 [SMILES: Cc1cc(C)c(-n2nccn2)c(C(=O)O)c1] | WO2013/68935, Page 58, Intermediate E-16 |
| A-11 | 5-Fluoro-2-[1,2,3]triazol-2-yl-benzoic acid | 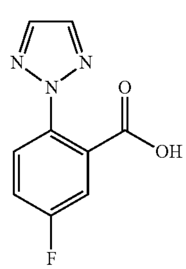 [SMILES: O=C(O)c1cc(F)ccc1-n1nccn1] | WO2011/50198, Pages 45-46, Intermediate 1 |

-continued

| Intermediate | Name | Structure | Synthesis for Patent drafting |
|---|---|---|---|
| A-12 | 4,5-Difluoro-2-[1,2,3]triazol-2-yl-benzoic acid | 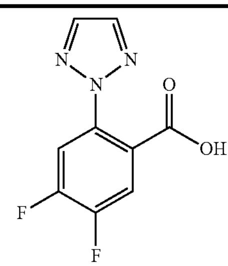 | WO2013/68935, Page 58, Intermediate E-24 |
| A-13 | 5-Cyano-2-[1,2,3]triazol-2-yl-benzoic acid | 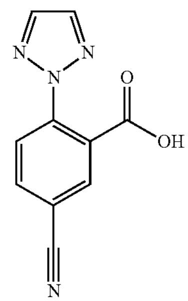 [SMILES: N#Cc1ccc(-n2nccn2)c(C(=O)O)c1] | WO2012/85852, Page 50, Intermediate 39 |
| A-15 | 5-Methoxy-2-[1,2,3]triazol-2-yl-benzoic acid | 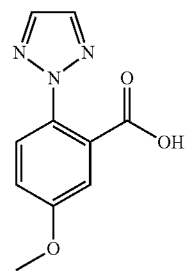 [SMILES: COc1ccc(-n2nccn2)c(C(=O)O)c1] | WO2011/50198, Page 49, Intermediate 10 |
| A-17 | 5-Methyl-2-pyrazol-1-yl-benzoic acid | 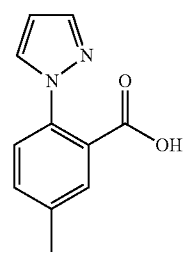 | WO2013/50938, Page 62, Intermediate B1.21 |
| A-18 | 3-Chloro-2-[1,2,3]triazol-2-yl-benzoic acid | 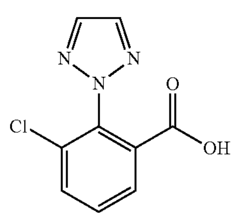 [SMILES: O=C(O)c1cccc(Cl)c1-n1nccn1] | WO2013/68935, Page 58, Intermediate E-23 |
| A-19 | 5-Fluoro-2-pyrazol-1-yl-benzoic acid | 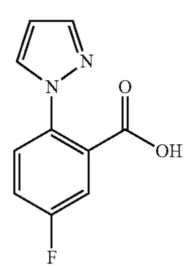 [SMILES: O=C(O)c1cc(F)ccc1-n1cccn1] | commercially available from Emolecules catalog number 28304663, MDL number: MFCD09054728 |

-continued

| Intermediate | Name | Structure | Synthesis for Patent drafting |
|---|---|---|---|
| A-21 | 2-(3-Methyl-[1,2,4]oxadiazol-5-yl)-benzoic acid | 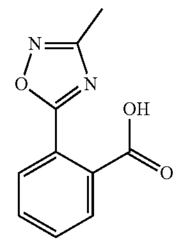 | commercially available from ABCR, catalog number AB225015, MDL number: MFCD08741426 |
| A-22 | 2-(5-Methyl-[1,3,4]oxadiazol-2-yl)-benzoic acid | 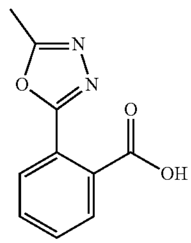 | commercially available from Emolecules catalog number 43618061, MDL number: MFCD09880459 |
| A-23 | 5-Methyl-2-pyridin-2-yl-benzoic acid | 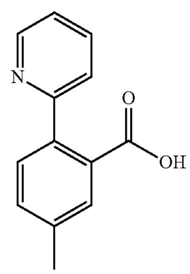 [SMILES: Cc1ccc(-c2ccccn2)c(C(=O)O)c1] | WO2013/50938, page 60, Intermediate B1.7 |
| A-24 | 5-Methyl-2-pyrimidin-2-yl-benzoic acid | 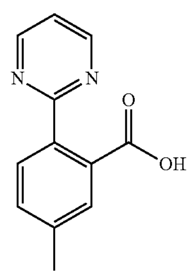 [SMILES: Cc1ccc(-c2ncccn2)c(C(=O)O)c1] | commercially available from Fluorochem catalog number 220053, MDL number: MFCD14706695 |
| A-25 | 2-Oxazol-5-yl-benzoic acid | 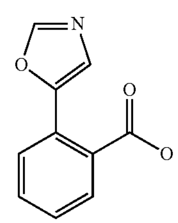 [SMILES: O=C(O)c1ccccc1-c1cnco1] | commercially available from Fluorochem catalog number 387559, MDL number: MFCD18375277 |
| A-26 | 2-Fluoro-6-pyrimidin-2-yl-benzoic acid | 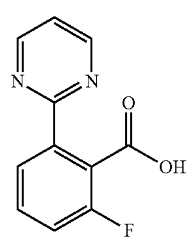 [SMILES: O=C(O)c1c(F)cccc1-c1ncccn1] | WO2011/50198 A1, page 52, Intermediate 14 |

-continued

| Intermediate | Name | Structure | Synthesis for Patent drafting |
|---|---|---|---|
| A-27 | Biphenyl-2-carboxylic acid | 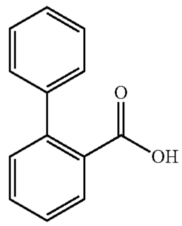 [SMILES: O=C(O)c1ccccc1-c1ccccc1] | commercially available from Aldrich catalog number B34702, MDL number: MFCD00002463 |
| A-28 | 4-Methoxy-2-pyrimidin-2-yl-benzoic acid | 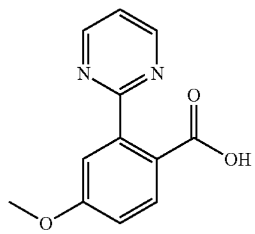 [SMILES: COc1ccc(C(=O)O)c(-c2ncccn2)c1] | WO2012/145581 A1, page 93, Intermediate 88 |
| A-29 | 5-Fluoro-2-pyrimidin-2-yl-benzoic acid | 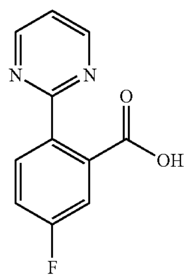 [SMILES: O=C(O)c1cc(F)ccc1-c1ncccn1] | commercially available from FCHGROUP catalog number FCH1791209, MDL number: MFCD24481550 |
| A-30 | 4-Fluoro-2-pyrimidin-2-yl-benzoic acid | 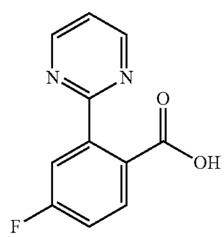 [SMILES: O=C(O)c1ccc(F)cc1-c1ncccn1] | WO2011/50200, page 95, Intermediate 85 |
| A-32 | 2-Fluoro-3-methyl-6-[1,2,3]triazol-2-yl-benzoic acid | 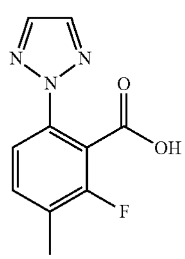 [SMILES: Cc1ccc(-n2nccn2)c(C(=O)O)c1F] | WO2013/50938, Page 59, Intermediate B1.1 |
| A-33 | 2-Fluoro-6-[1,2,3]triazol-2-yl-benzoic acid | 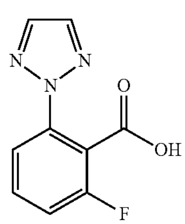 [SMILES: O=C(O)c1c(F)cccc1-n1nccn1] | WO2012/145581, Page 49, Intermediate 12 |

-continued

| Intermediate | Name | Structure | Synthesis for Patent drafting |
|---|---|---|---|
| A-34 | 4-Methyl-2-[1,2,3]triazol-1-yl-benzoic acid | 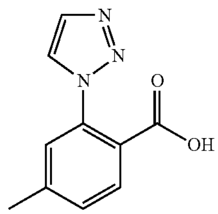 | side product in the preparation following WO2013/50938, Page 62, Intermediate B1.17 |
| A-35 | 2-Pyrazol-1-yl-benzoic acid | 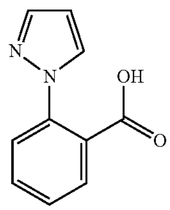 [SMILES: O=C(O)c1ccccc1-n1cccn1] | commercially available from Fluorochem catalog number 065672, MDL number: MFCD03086184 |
| A-36 | 3-Fluoro-2-pyrimidin-2-yl-benzoic acid | 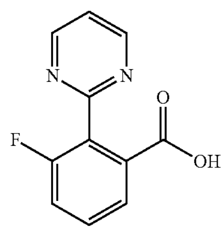 [SMILES: O=C(O)c1cccc(F)c1-c1ncccn1] | WO2011/50200, page 78, Intermediate 52 |
| A-39 | 4'-Methoxy-biphenyl-2-carboxylic acid | 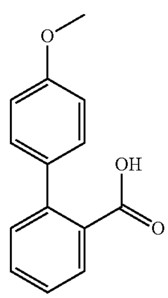 [SMILES: COc1ccc(-c2ccccc2C(=O)O)cc1] | commercially available from Fluorochem catalog number 011466, MDL number: MFCD03426469 |
| A-40 | 4-Chloro-2-pyrrol-1-yl-benzoic acid | 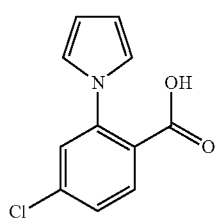 [SMILES: O=C(O)c1ccc(Cl)cc1-n1cccc1] | commercially available from Fluorochem catalog number 351423, MDL number: MFCD09732958 |
| A-41 | 3'-Methyl-biphenyl-2-carboxylic acid | 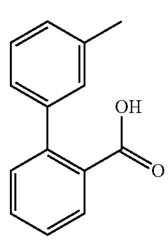 [SMILES: Cc1cccc(-c2ccccc2C(=O)O)c1] | commercially available from Fluorochem catalog number 313750, MDL number: MFCD04039113 |

-continued

| Intermediate | Name | Structure | Synthesis for Patent drafting |
|---|---|---|---|
| A-42 | 3-Methyl-2-pyrimidin-2-yl-benzoic acid | 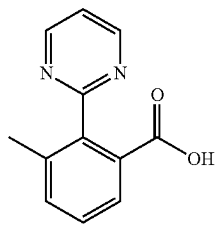 [SMILES: Cc1cccc(C(=O)O)c1-c1ncccn1] | commercially available from DEBYESCI catalog number DA-10619, MDL number: MFCD26401335 |
| A-43 | 4-Methyl-2-pyrimidin-2-yl-benzoic acid | 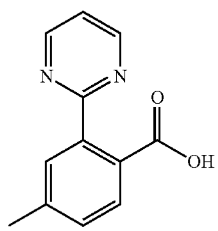 [SMILES: Cc1ccc(C(=O)O)c(-c2ncccn2)c1] | Organic Letters, 2014, vol. 16, # 22 p. 5890-5893 |
| A-44 | 2-Pyrimidin-2-yl-benzoic acid | 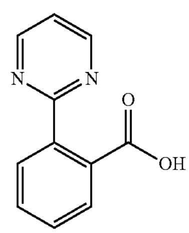 [SMILES: O=C(O)c1ccccc1-c1ncccn1] | commercially available from DEBYESCI catalog number DA-06142, MDL number: MFCD09999084 |
| A-45 | 4-Methoxy-2-[1,2,3]triazol-2-yl-benzoic acid | 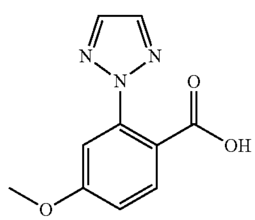 [SMILES: COc1ccc(C(=O)O)c(-n2nccn2)c1] | WO2011/50198, Pages 73-74, Intermediate 73 |
| A-46 | 2-Oxazol-2-yl-benzoic acid | 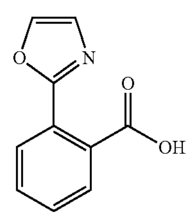 [SMILES: O=C(O)c1ccccc1-c1ncco1] | WO2006/76644, Page 212-213, Example 184 [00592] |

3,5-Difluoro-2-[1,2,3]triazol-2-yl-benzoic Acid A-47

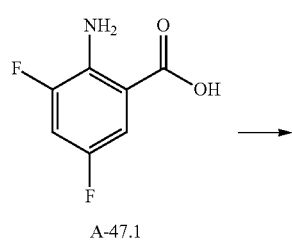

A-47.1

-continued

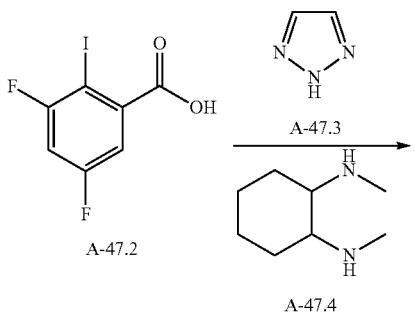

A-47.2

A-47.3

A-47.4

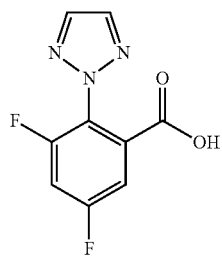

A-47

Step 1:

A-47.1 (50 g, 283 mmol) in H$_2$SO$_4$ (519 mL, 3114 mmol) is stirred for 15 min at RT before being cooled to 0° C., at which point NaNO$_2$ (26 g, 368 mmol) in H$_2$O (50 mL) is added dropwise and the mixture is stirred for 1.5 h. To this mixture is added slowly KI (275 g, 1415 mmol) in H$_2$O (300 mL). The reaction mixture is allowed to warm to RT and then heated to 90° C. for 6 h. The mixture is poured into water and extracted with EA, the organic phase is washed with Na$_2$S$_2$O$_3$ (aq. solution), then washed with brine, dried and concentrated. The residue is dissolved in NaOH (4 M, aq. solution) and filtered, the filtrate is acidified with HCl (4 M, aq. solution). The precipitate is filtered off, washed with water and dried to give 4.0 g of A-47.2. ESI-MS: 285 [M+H]$^+$; HPLC (Rt): 0.74 min (Method C).

Step 2:

A mixture of A-47.2 (3.5 g, 11 mmol), A-47.3 (1.6 g, 22 mmol), CuI (0.18 g, 0.89 mmol), A-47.4 (0.70 mL, 4.4 mmol) and K$_2$CO$_3$ (3.5 g, 24 mmol) in DMF is heated to 100° C. by microwave irradiation for 1.5 h. The mixture is poured into water and extracted with EA, the organic phase is washed with water. The combined aq. phases are acidified with HCl (0.5 N, aq. solution) and extracted with EA. The organic phase is washed with brine, dried and concentrated to give the crude product which is purified by HPLC-MS (using a solvent gradient H$_2$O/ACN with TFA) to provide 1.25 g of A-47. ESI-MS: 226 [M+H]$^+$; HPLC (Rt): 1.88 min (Method A).

4-Cyano-2-[1,2,3]triazol-2-yl-benzoic Acid A-48

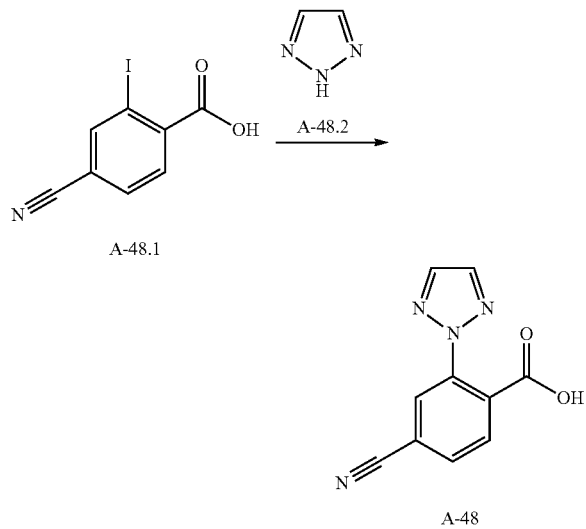

To a mixture of A-48.1 (0.70 g, 2.56 mmol) in DMF (10 mL) at RT under a nitrogen atmosphere is added A-48.2 (0.30 mL, 5.13 mmol) and Cs$_2$CO$_3$ (1.67 g, 5.13 mmol) and CuI (24 mg, 0.13 mmol) and the mixture is heated to 110° C. for 1 h before being cooled to RT. Water (20 mL) is added, the aq. phase is acidified with HCl (4M, aq. solution) and then extracted with EA, the organic phase is dried and concentrated. The crude product is purified by HPLC-MS (using a solvent gradient H$_2$O/ACN with TFA) to provide 0.40 g of A-48. ESI-MS: 215 [M+H]$^+$; HPLC (Rt): 0.39 min (Method B).

3,4-Difluoro-2-[1,2,3]triazol-2-yl-benzoic Acid A-49

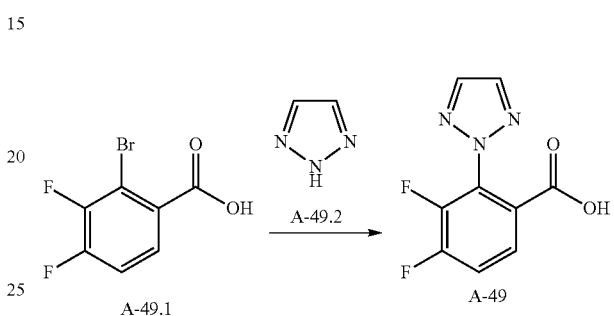

A mixture of A-49.1 (9.0 g, 36 mmol), A-49.2 (5.3 g, 72 mmol), CuI (0.70 g, 3.6 mmol) and K$_2$CO$_3$ (11 g, 78 mmol) in DMF (100 mL) is heated at 120° C. for 16 h. The mixture is cooled to RT, the pH adjusted to pH2 with HCl (4M, aq. solution) and extracted with EA. The organic phase is washed with brine, dried and concentrated to provide 3.0 g of A-49. ESI-MS: 226 [M+H]$^+$; HPLC (Rt): 0.45 min (Method B).

2-(1-Methyl-1H-pyrazol-4-yl)-benzoic Acid A-50

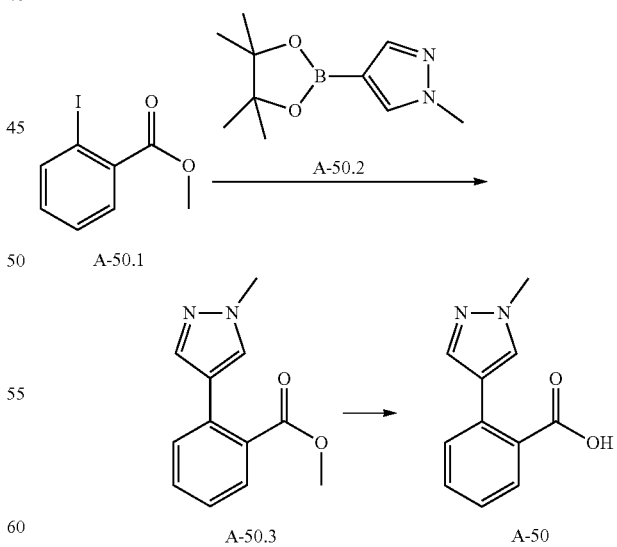

Step 1:

A mixture of A-50.1 (2.0 g, 7.6 mmol), A-50.2 (1.8 g, 8.4 mmol), K$_2$CO$_3$ (1.6 g, 15 mmol), Pd(dppf)Cl$_2$ (0.28 g, 0.38 mmol) in 1,4-dioxane (6 mL) and water (3 mL) is heated for 24 h at 160° C. by microwave irradiation. The mixture is cooled to RT, filtered and concentrated. The crude product is purified by HPLC-MS (using a solvent gradient H$_2$O/ACN with NH$_4$OH) to provide 1.3 g of A-50.3. ESI-MS: 217 [M+H]$^+$; HPLC (Rt): 0.49 min (Method Q).

Step 2:

A mixture of A-50.3 (1.3 g, 6.1 mmol), NaOH (4M, aq. solution) (7.5 mL, 30 mmol) in MeOH (7.5 mL) is stirred overnight at RT. The mixture is concentrated and then extracted with DCM and EA. The combined organics were concentrated to provide 750 mg of A-50. ESI-MS: 203 [M+H]$^+$; HPLC (Rt): 0.40 min (Method Q).

4-Fluoro-2-(5-methyl-[1,3,4]oxadiazol-2-yl)-benzoic Acid A-51

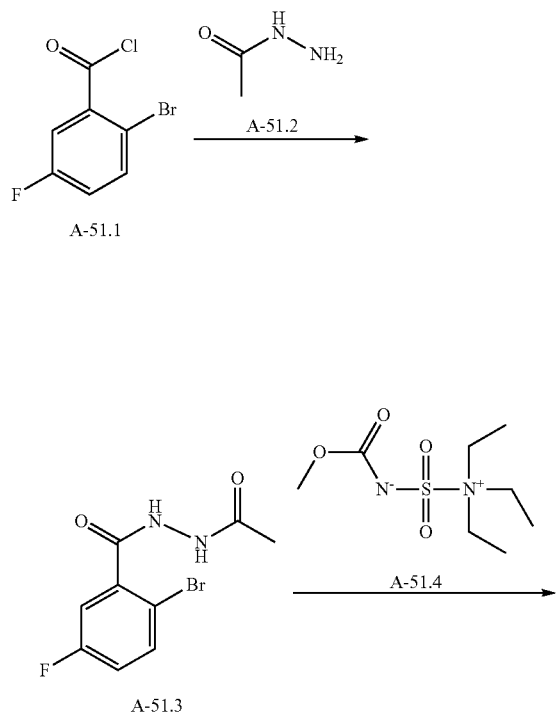

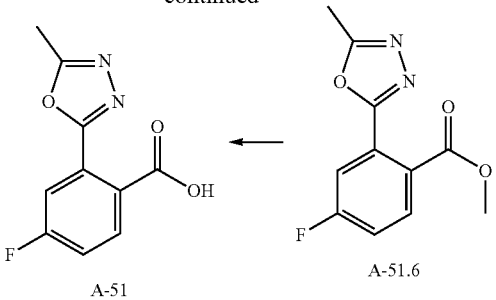

Step 1:

To A-51.1 (2.0 g, 8.4 mmol) in dry DCM (50 mL) is added A-51.2 (0.83 g, 10 mmol) and the reaction is stirred at RT for 1 h. Another portion of A-51.2 (0.83 g, 10 mmol) is added and the reaction is stirred overnight. MeOH (5 mL) is added and the solvent is reduced to half the volume. The precipitate is filtered to provide 0.50 g of A-51.3. The filtrate is concentrated and purified by flash column chromatography on silica gel (using a solvent gradient from 100% DCM to 95% DCM and 5% MeOH) to provide a further 1.1 g of A-51.3. ESI-MS: 275 [M+H]$^+$; HPLC (Rt): 0.47 min (Method D).

Step 2:

To a mixture of A-51.3 (1.6 g, 5.7 mmol) in DCM (50 mL) is added A-51.4 (2.7 g, 11 mmol) and the mixture stirred overnight. Na$_2$CO$_3$ (2M aq. solution) is added, the aqueous phase is extracted with DCM, the combined organic phases are washed with brine and concentrated to provide 0.80 g of A-51.5. ESI-MS: 257 [M+H]$^+$; HPLC (Rt): 0.47 min (Method D).

Step 3:

To A-51.5 (0.80 g, 3.1 mmol) in dry MeOH (10 mL) is added TEA (1.1 mL, 7.5 mmol) followed by Pd(dppf)Cl$_2$.DCM (152 mg, 0.19 mmol) and the reaction is stirred at 70° C. under a pressure of 3 bar carbon monoxide for 4 h. The mixture is filtered, concentrated and purified by HPLC-MS (using a solvent gradient H$_2$O/ACN with NH$_4$OH) to provide 0.55 g of A-51.6. ESI-MS: 237 [M+H]$^+$; HPLC (Rt): 0.88 min (Method E).

Step 4:

To A-51.6 (0.55 g, 2.3 mmol) in MeOH (4 mL) is added NaOH (4M, aq. solution, 3.9 mL, 12 mmol) and the reaction is stirred at RT for 30 min. The mixture is concentrated, the pH adjusted to pH 2 with HCl (4M, aq. solution) and extracted with EA, dried and concentrated to provide 0.42 g of A-51. ESI-MS: 223 [M+H]$^+$; HPLC (Rt): 0.10 min (Method D).

The following acids are prepared in analogy to the above described procedure using the corresponding starting material:

| Intermediate | Name | Structure | ESI-MS [M + H]+ | HPLC (Rt) [min] | methode Name |
|---|---|---|---|---|---|
| A-52 | 3-Fluoro-2-(5-methyl-[1,3,4]oxadiazol-2-yl)-benzoic acid | 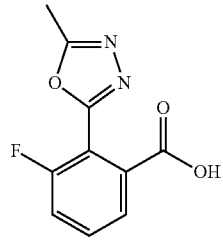 [SMILES: Cc1nnc(-c2c(F)cccc2C(=O)O)o1] | 223 | 0.10 | D |
| A-53 | 4-Methyl-2-(5-methyl-[1,3,4]oxadiazol-2-yl)-benzoic acid | 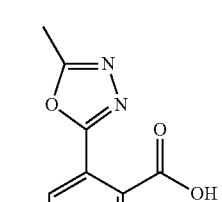 | 271 | 0.22 | D |
| A-54 | 3-Methyl-2-(5-methyl-[1,3,4]oxadiazol-2-yl)-benzoic acid | 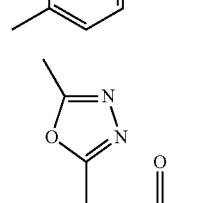 | 219 | 0.10 | D |

2-(5-Methyl-oxazol-2-yl)-benzoic Acid A-55

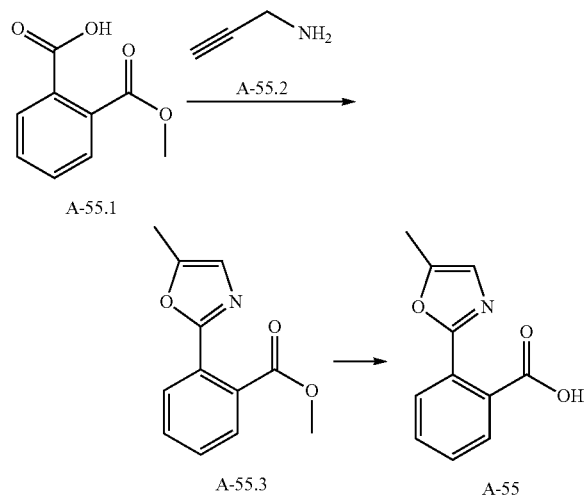

Step 1:

To A-55.1 (2.0 g, 11 mmol) in DCM (100 mL) and dry DMF (90 µL, 1.1 mmol) at 0° C. is added thionyl chloride (805 µL, 11 mmol) and the mixture is stirred at RT for 1 h. The reaction is then cooled to 0° C. and DIPEA (3.9 mL, 22 mmol) and A-55.2 (853 µL, 13 mmol) are added. The mixture is stirred at 0° C. for 45 min, NH$_4$Cl (sat. aq. solution) is added and the product is extracted with DCM. The organic phase is washed with NH$_4$Cl (sat. aq. solution), water, NaHCO$_3$ (sat. aq. solution) and brine. The organic phase is concentrated and 1,4-dioxane (100 mL) is added. The mixture is cooled with an ice bath and NaH (60% disp. in mineral oil, 488 mg, 12 mmol) is added. The mixture is stirred at RT for 30 min and then heated to reflux for 4 h. After cooling, NH$_4$Cl (sat. aq. solution, 5 mL) is added, the mixture is concentrated and extracted with DCM. The organic phase is washed with NH$_4$Cl (sat. aq. solution) and water. Solvent is evaporated and the crude product is purified by flash column chromatography on silica gel (using a solvent mixture cyclohexane/EA=7/3) to provide 240 mg of A-55.3. ESI-MS: 218 [M+H]+; HPLC (Rt): 0.95 min (Method M).

Step 2:

A mixture of A-55.3 (390 mg, 1.8 mmol) and LiOH—H$_2$O (150 mg, 3.6 mmol) in THF (30 mL) and water (10 mL) is heated at reflux for 5 h. Another portion of LiOH.H$_2$O (150 mg, 3.6 mmol) is added and the reaction mixture heated at reflux for another 4 h and then stirred overnight at RT. After cooling, the mixture is acidified with HCl (4M, aq. solution) and extracted with EA. The organic phase is concentrated to provide 170 mg of A-55. ESI-MS: 204 [M+H]+; HPLC (Rt): 0.48 min (Method M).

2-(5-Methyl-[1,2,4]oxadiazol-3-yl)-benzoic Acid
A-57

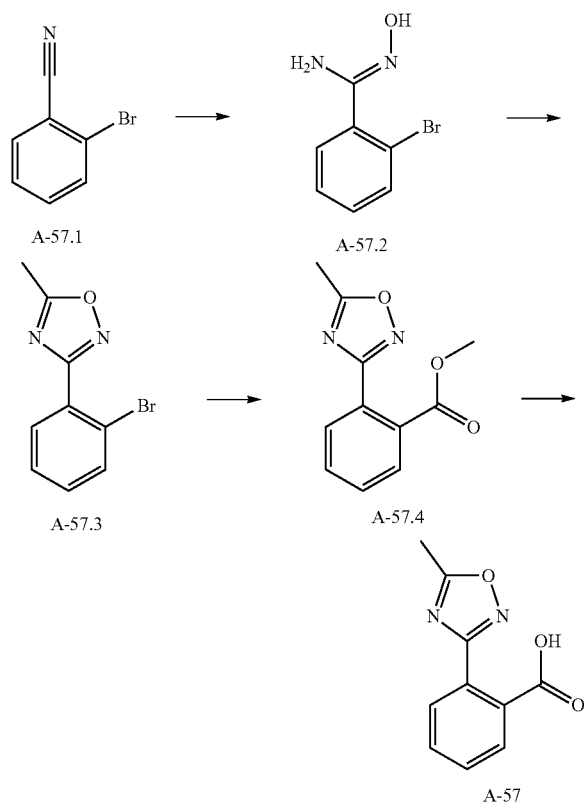

2-(2-Methyl-oxazol-5-yl)-benzoic Acid A-58

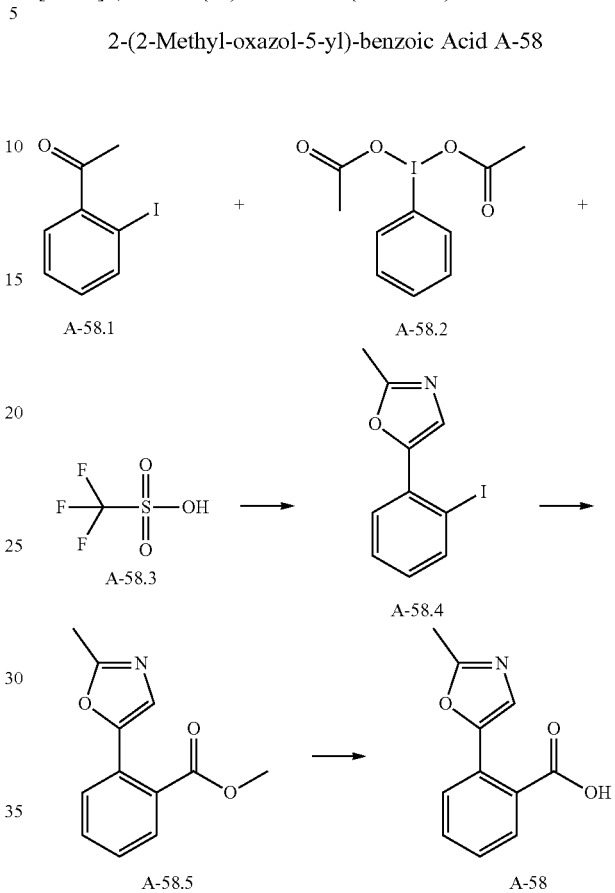

Step 1:

A mixture of NH$_2$OH.HCl (29 g, 0.41 mol) and K$_2$CO$_3$ (57 g, 0.41 mol) in EtOH (500 mL) is stirred at RT for 30 min. A-57.1 (30 g, 0.17 mol) is added and the reaction mixture is heated to 70° C. for 12 h. After filtration, the solvent is evaporated under reduced pressure and the residue purified by flash column chromatography (using a solvent gradient petroleum ether/EA 5:1 to 2:1) to obtain 25 g of A-57.2.

Step 2:

To A-57.2 (18 g, 0.084 mol) in ACN (200 mL) are added Ac$_2$O (10 g; 0.1 mol) and TEA (17 g, 0.17 mol). The mixture is stirred at 120° C. for 48 h. The mixture is concentrated in vacuum and the residue purified by flash column chromatography on silica gel (using a solvent gradient petroleum ether/EA 10/0 to 10/1) to afford 9 g of A-57.3. ESI-MS: 239/241 [M+H]$^+$; HPLC (Rt): 1.43 min (method Z)

Step 3:

To a mixture of A-57.3 (9 g, 0.038 mol) and TEA (12 g, 0.11 mol) in MeOH (200 mL) is added Pd(dppf)Cl$_2$ (1 g). Then the mixture is stirred at 50° C. under an atmosphere of carbon monoxide (50 psi) for 16 h. The mixture is concentrated and the residue purified by flash column chromatography on silica gel (using a solvent gradient petroleum ether/EA 10/0 to 5/1) to afford 4 g of A-57.4. ESI-MS: 219 [M+H]$^+$; HPLC (Rt): 1.29 min (method Z)

Step 4:

To a mixture of A-57.4 (4 g, 0.018 mol) in MeOH (40 mL) and H$_2$O (4 mL) is added NaOH (1.5 g, 0.037 mol) at 25° C. under a nitrogen atmosphere. The mixture is stirred at 70° C. for 4 h, then concentrated and the residue dissolved in H$_2$O. The pH is adjusted to pH3 with HCl (4M, aq. solution) and the product filtered to obtain 2.2 g of A-57. ESI-MS: 205 [M+H]$^+$; HPLC (Rt): 1.72 min (method I)

Step 1:

To A-58.2 (1.3 g, 4.1 mmol) in DCM (20 mL) is added A-58.3 (1.2 g, 8.1 mmol) and the mixture is stirred for 1 h. Then A-58.1 (0.50 g, 2.0 mmol) and ACN (0.83 g, 20 mmol) are added and the mixture is stirred at 45° C. for 5 h. The pH of the mixture is adjusted with NaHCO$_3$ (aq. sat. solution) to pH8, extracted with DCM and concentrated. The residue is purified by flash column chromatography on silica gel (using a solvent gradient petroleum ether/EA from 40/1 to 20/1) to provide 0.20 g of A-58.4. ESI-MS: 286 [M+H]$^+$; HPLC (Rt): 1.60 min (Method Z)

Step 2:

A mixture of A-58.4 (2.3 g, 7.9 mmol), TEA (4.0 g, 39 mmol), Pd(dppf)Cl$_2$ (0.58 g, 0.79 mmol) and MeOH (70 mL) is stirred at 50° C. under an atmosphere of carbon monoxide (50 psi) for 16 h. The mixture is concentrated and purified by flash column chromatography on silica gel (using a solvent gradient petroleum ether/EA from 80/1 to 40/1) to provide 2.0 g of A-58.5. ESI-MS: 218 [M+H]$^+$; HPLC (Rt): 0.71 min (method C).

Step 3:

A mixture of A-58.5 (2.0 g, 9.2 mmol), MeOH (10 mL) and LiOH—H$_2$O (0.46 g, 11 mmol) is stirred at 25° C. for 16 h. The organic solvent is evaporated, the residue is treated with HCl (1M, aq. solution) (pH 3-4). The precipitate is filtered and dried to provide 1.4 g of A-58. ESI-MS: 204 [M+H]$^+$; HPLC (Rt): 2.38 min (method X).

3,5-Difluoro-2-[1,2,3]triazol-2-yl-benzoic Acid A-59

Amine Intermediates

Ethyl-[(S)-1-methyl-2-(5-trifluoromethyl-pyridin-2-yloxy)-ethyl]-amine B-1a

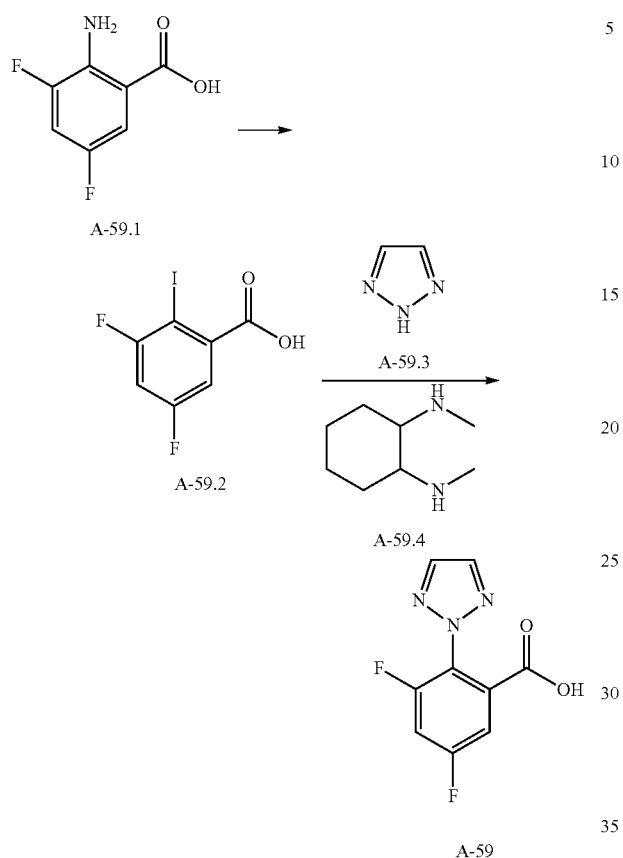

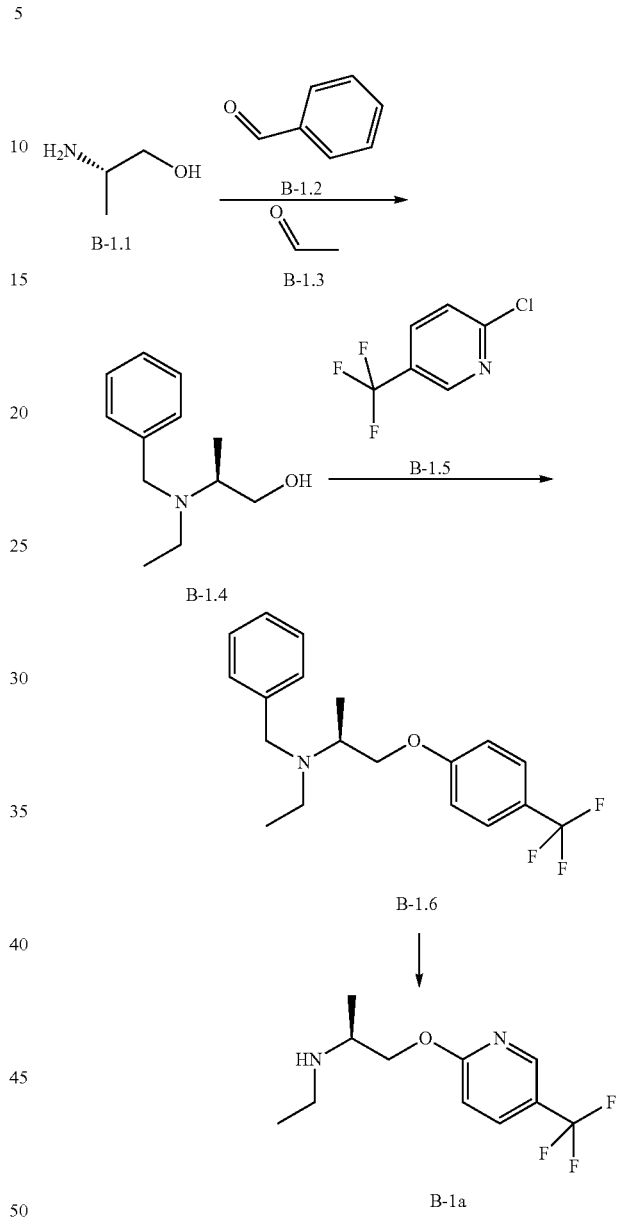

Step 1:

A mixture of A-59.1 (50 g, 283 mmol) in H$_2$SO$_4$ (519 mL, 3.1 mmol) is stirred for 15 min at RT and then cooled to 0° C. NaNO$_2$ (26 g, 368 mmol) in H$_2$O (50 mL) is added dropwise and stirred for 1.5 h. To this mixture KI (275 g, 1.4 mmol) in H$_2$O (300 mL) is added slowly. The reaction mixture is allowed to warm to RT and then heated to 90° C. for 6 h. The mixture is poured into water and extracted with EA, the organic phase is washed with Na$_2$S$_2$O$_3$ (aq. solution), then washed with brine, dried and concentrated. The solid is dissolved in NaOH (4M, aq. solution) and filtered, the filtrate is acidified with HCl (4M, aq. solution). The precipitate is filtered off, washed with water and dried to give 57 g (90% purity) of A-59.2. ESI-MS: 285 [M+H]$^+$; HPLC (Rt): 0.74 min (Method C).

Step 2:

A mixture of A-59.2 (3.5 g, 11 mmol), A-59.3 (1.6 g, 22 mmol), CuI (0.18 g, 0.89 mmol), A-59.4 (0.70 mL) and K$_2$CO$_3$ (3.5 g, 24 mmol) in DMF (10 mL) is heated to 100° C. by microwave irradiation for 1.5 h. The mixture is poured into water and extracted with EA, the organic phase is washed with water. The combined aq. phases are acidified with HCl (0.5 N, aq. solution) and extracted with EA. The organic phase is washed with brine, dried and concentrated to give the crude product which is purified by HPLC-MS (using a solvent gradient H$_2$O/ACN with TFA) to provide 1.3 g of A-59. ESI-MS: 226 [M+H]$^+$; HPLC (Rt): 1.88 min (Method A).

Step 1:

A mixture of B-1.1 (5.0 g, 66 mmol) and B-1.2 (6.8 mL, 66 mmol) in THF (180 mL) is stirred at RT for 1 h. NaBH(OAc)$_3$ (44 g, 199 mmol) is added at 0° C. and stirred at RT for 30 min. B-1.3 (11 mL, 199 mmol) in THF (20 mL) is added dropwise within 10 min at 0° C. and the mixture is stirred at RT overnight. Additional B-1.3 (10 mL) is added and stirred at RT for 3 h. The precipitate is filtrated and washed with THF and DCM. NaHCO$_3$ (sat. aq. solution, 200 mL) is added and solid NaHCO$_3$ until gas formation subsides. The water phase is extracted with DCM, dried and concentrated to provide 12 g of B-1.4. ESI-MS: 194 [M+H]$^+$; HPLC (Rt): 1.13 min (Method E).

Step 2:

To a mixture of B-1.4 (2.8 g, 15 mmol) and potassium tert-butoxide (3.5 g, 31 mmol) in dry 1,4-dioxane (80 mL)

under nitrogen B-1.5 (2.8 g, 15 mmol) is added. The mixture is heated to 60° C. for 2 h, poured into water and extracted with EA. The organic phase is extracted with NaCl (sat. aq. solution), dried and concentrated to provide 4.7 g of B-1.6. ESI-MS: 339 [M+H]$^+$; HPLC (Rt): 1.31 min (Method F).

Step 3:

To a mixture of B-1.6 (4.7 g, 12 mmol) in MeOH (40 mL) is added Pd/C (0.50 g). The reaction is stirred at RT under an atmosphere of hydrogen (3.5 bar) for 2 h. The catalyst is filtered off and the solvent is removed under reduced pressure to provide 3.1 g of B-1a. ESI-MS: 249 [M+H]$^+$; HPLC (Rt): 1.04 min (Method F); $^1$H NMR (300 MHz, DMSO-$d_6$) δ ppm 0.96-1.03 (m, 3H), 1.06 (d, 3H), 2.60 (m, 2H), 2.99 (m, 1H), 4.13 (dd, 1H), 4.24 (dd, 1H), 7.01 (d, 1H), 8.05 (dd, 1H), 8.56 (m, 1H).

Ethyl-[(S)-1-methyl-2-(5-trifluoromethyl-pyridin-2-yloxy)-ethyl]-amine Hydrochloride B-1a.HCl

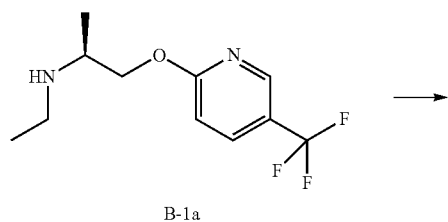

To a mixture of B-1a (400 mg, 1.6 mmol) in 1,4-dioxane (20 mL) is added HCl (4M, in 1,4-dioxane, 0.81 mL, 3.22 mmol) and the mixture is stirred for 1 h. The solvent is evaporated to afford 450 mg of B-1a.HCl. ESI-MS: 249 [M+H]$^+$; HPLC (Rt): 0.72 min (Method M). $^1$H NMR (400 MHz, DMSO-$d_6$) δ ppm 1.22 (t, J 7.24 Hz, 3H), 1.33 (d, J 6.75 Hz, 3H), 2.98-3.10 (m, 2H), 3.60-3.70 (m, 1H), 4.48 (dd, 1H), 4.55 (dd, 1H), 7.09 (d, 1H), 8.14 (dd, 1H), 8.62 (m, 1H), 8.76 (br. s., 3H).

Ethyl-[(S)-2-(3-fluoro-5-trifluoromethyl-pyridin-2-yloxy)-1-methyl-ethyl]-amine B-1b

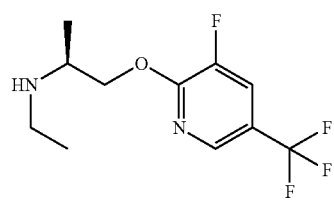

Intermediate B-1b was synthesized in analogy to the procedure of B-1a with the modification that in step 3 the deprotection was performed using Pd(OH)$_2$ instead of Pd/C.

ESI-MS: 357 [M+H]$^+$; HPLC (Rt): 1.32 min (Method G); $^1$H NMR (400 MHz, DMSO-$d_6$) δ ppm 0.98-1.01 (t, 3H), 1.08 (d, 3H); 2.61 (m, 1H) 2.51-2.56 (m, 2H); 3.03 (m, 1H); 4.21-4.26 (dd, 1H); 4.33-4.37 (dd, 1H); 8.19 (d, 1H); 8.4 (m, 1H).

(S)-2-Ethylamino-propan-1-ol Hydrochloride B-2

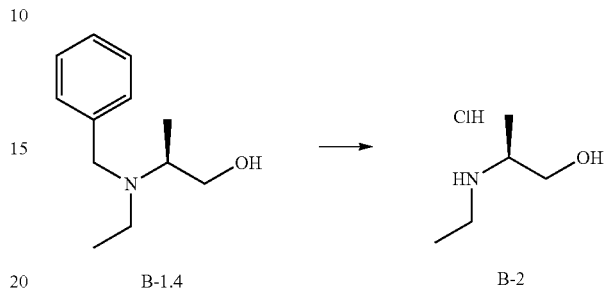

Step 1:

To a mixture of B-1.4 (9.0 g, 47 mmol) in MeOH (200 mL), Pd/C (900 mg) is added. The reaction is stirred at RT and under an atmosphere of hydrogen (4 bar) for 4 h. The catalyst is filtered and HCl (4M in 1,4-dioxane, 14 mL, 56 mmol) is added and and the resulting mixture is concentrated to provide 6.0 g of B-2. ESI-MS: 104 [M+H]$^+$; HPLC (Rt): 0.20 min (Method L).

[(S)-2-(5-Chloro-pyridin-2-yloxy)-1-methyl-ethyl]-ethyl-amine B-3a

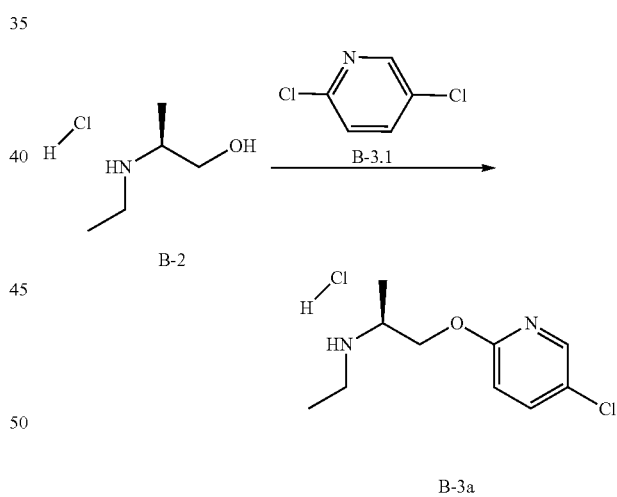

To a mixture of B-2 (2.6 g, 19 mmol) in dry DMF (100 mL) at 5° C. under nitrogen is added NaH (60% disp. in mineral oil, 3.0 g, 75 mmol) portionwise and the mixture is stirred at RT for 1 h. B-3.1 (4.2 g, 29 mmol) is added portionwise and the mixture is heated to 70° C. for 2 h. After cooling citric acid (10% aq. solution) is added and extracted with Et$_2$O. The water phase is separated, the pH adjusted to pH10 with NH$_4$OH and extracted with DCM. The organic layer is dried and evaporated. The residue is dissolved in EA and treated with HCl (1M in Et$_2$O) at 0° C. The resultant solid was filtered, washed with EA and n-hexane to provide 3.50 g of B-3a. ESI-MS: 215 [M+H]$^+$; HPLC (Rt): 3.17 min (Method 0); $^1$H NMR (500 MHz, DMSO-$d_6$) δ ppm 1.24 (t, 3H), 1.34 (d, 3H), 2.95-3.08 (m, 2H), 3.59 (m, 1H), 4.39-4.49 (m, 2H), 6.91-6.97 (m, 1H), 7.86 (dd, 1H), 8.23 (d, 1H), 9.09-9.23 (br. s., 2H).

Ethyl-[(S)-1-methyl-2-(5-trifluoromethoxy-pyridin-2-yloxy)-ethyl]-amine Hydrochloride B-3b

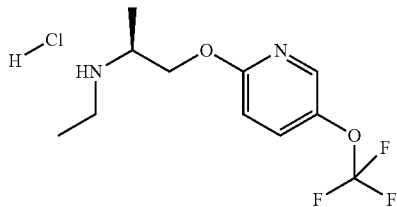

Intermediate B-3b was synthesized in analogy to the procedure of B-3a. ESI-MS: 265 [M+H]+; HPLC (Rt): 0.79 min (Method M); $^1$H NMR (500 MHz, DMSO-$d_6$) δ ppm 1.23 (t, 3H), 1.34 (d, 3H), 2.94-3.10 (m, 2H), 3.56-3.66 (m, 1H), 4.39-4.53 (m, 2H), 7.02 (d, 1H), 7.88 (ddt, 1H), 8.30 (d, 1H), 8.94 (br. s., 2H).

[(S)-2-(5-Bromo-pyridin-2-yloxy)-1-methyl-ethyl]-ethyl-amine Hydrochloride B-3c

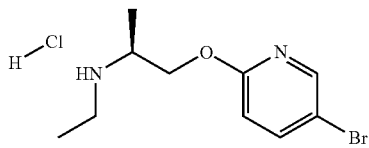

Intermediate B-3c was synthesized in analogy to the procedure of B-3a. ESI-MS: 296 [M+H]+; HPLC (Rt): 0.68 min (Method M); $^1$H NMR (300 MHz, DMSO-$d_6$) δ ppm 1.23 (t, 3H), 1.33 (d, 3H), 3.60 (m, 1H), 4.32-4.54 (m, 2H), 6.90 (d, 1H), 7.96 (dd, 1H), 8.31 (d, 1H), 8.94-9.06 (br. d., 2H).

(S)-1-Methyl-2-(5-trifluoromethyl-pyridin-2-yloxy)-ethylamine B-4

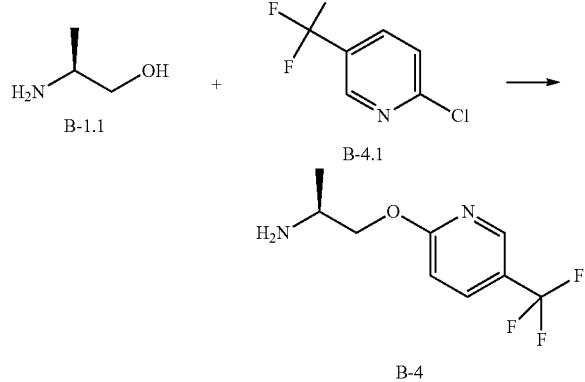

To a mixture of B-1.1 (0.80 g, 11 mmol) in dry DMF (5 mL) at 5° C. under nitrogen is added NaH (60% disp. in mineral oil, 0.51 g, 13 mmol) and the mixture is stirred at RT for 1 h. B-4.1 (2.3 g, 13 mmol) is added and the mixture is stirred at RT for 2 h. The reaction is treated with water and extracted with Et$_2$O. The organic phase is separated, dried and evaporated. The residue is purified by flash column chromatography on silica gel (using a solvent gradient from DCM/MeOH 10/0 to 9/1) to provide 1.6 g B-4. ESI-MS: 221 [M+H]+; HPLC (Rt): 0.66 min (Method M); $^1$H NMR (500 MHz, DMSO-$d_6$) δ ppm 1.03-1.09 (d, 3H), 3.16-3.23 (m, 1H), 4.07-4.16 (m, 2H), 7.02 (d, 1H), 8.06 (dd, 1H), 8.54-8.57 (m, 1H).

Alcohol Intermediates

N-Ethyl-3-fluoro-N—((S)-2-hydroxy-1-methyl-ethyl)-2-[1,2,3]triazol-2-yl-benzamid C-1

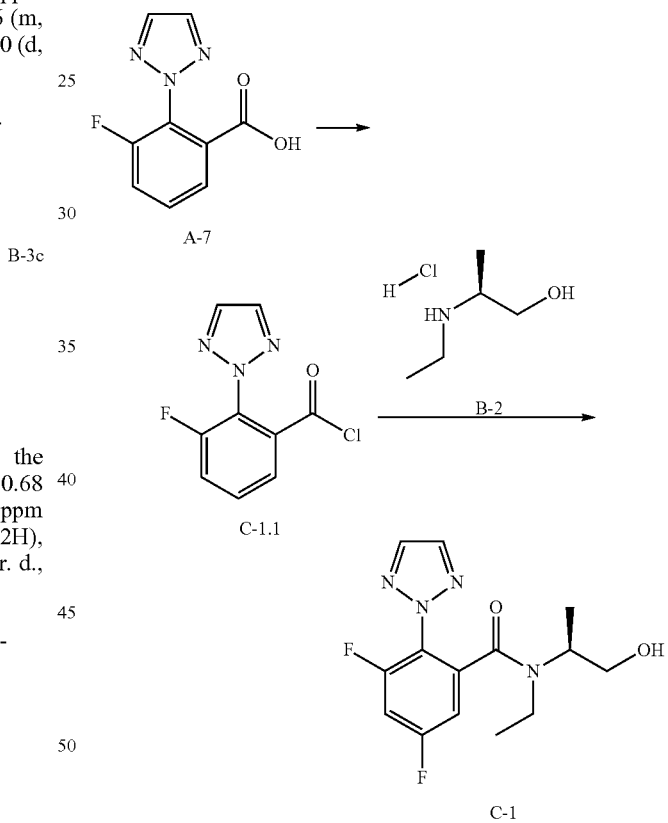

Step 1:

A mixture of A-7 (1.2 g, 6.0 mmol), thionyl chloride (9.0 mL, 123 mmol), DMF (0.25 mL) and DCM (7.0 mL) is stirred at RT for 1 h. The mixture is concentrated and evaporated with toluene to provide 1.7 g of C-1.1. ESI-MS: 222 [M+H]+; HPLC (Rt): 0.53 min (Method H).

Step 2:

To a mixture of C-1.1 (1.7 g, 6.0 mmol) and TEA (2.1 mL, 15 mmol) in THF (50 mL) and DCM (20 mL) is added B-2 (0.92 g, 6.6 mmol). The mixture is stirred at RT overnight. The precipitate is filtered, washed with EA and the filtrate is concentrated. The crude product is purified by HPLC-MS (using a solvent gradient H₂O/ACN with NH₄OH) to provide 1.33 g of C-1. ESI-MS: 291 [M+H]⁺; HPLC (Rt): 0.46 min (Method H).

N-Ethyl-N—((S)-2-hydroxy-1-methyl-ethyl)-5-methyl-2-[1,2,3]triazol-2-yl-benzamide C-2

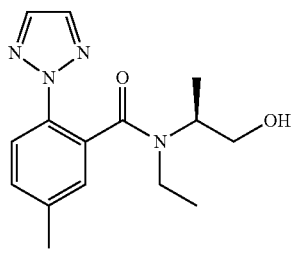

C-2

C-2 was synthesized in analogy to the procedure described for C-1. ESI-MS: 289 [M+H]⁺; HPLC (Rt): 0.86 min (Method G).

N-Ethyl-N—((S)-2-hydroxy-1-methyl-ethyl)-4-methoxy-2-[1,2,3]triazol-2-yl-benzamide C-3

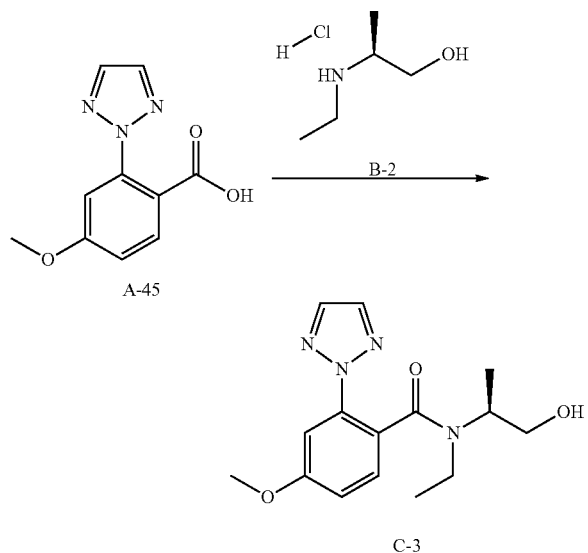

Step 5:
To a mixture of A-45 (0.31 g, 1.4 mmol) in DMF (5.0 mL) is added HATU (0.60 g, 1.6 mmol), DIPEA (0.75 mL, 4.3 mmol) and B-2 (0.20 g, 1.4 mmol) and the mixture is stirred at RT overnight. EA is added and the organic phase is washed with citric acid (10% aq. solution) and brine. The organic phase is dried and concentrated and the residue is purified by flash column chromatography on silica gel (using a solvent gradient DCM/MeOH 95/5) to provide 280 mg of C-3. ESI-MS: 305 [M+H]⁺; HPLC (Rt): 0.77 min (method M).

Amides

2-Bromo-N-ethyl-N—[(S)-1-methyl-2-(5-trifluoromethyl-pyridin-2-yloxy)-ethyl]-benzamide D-1

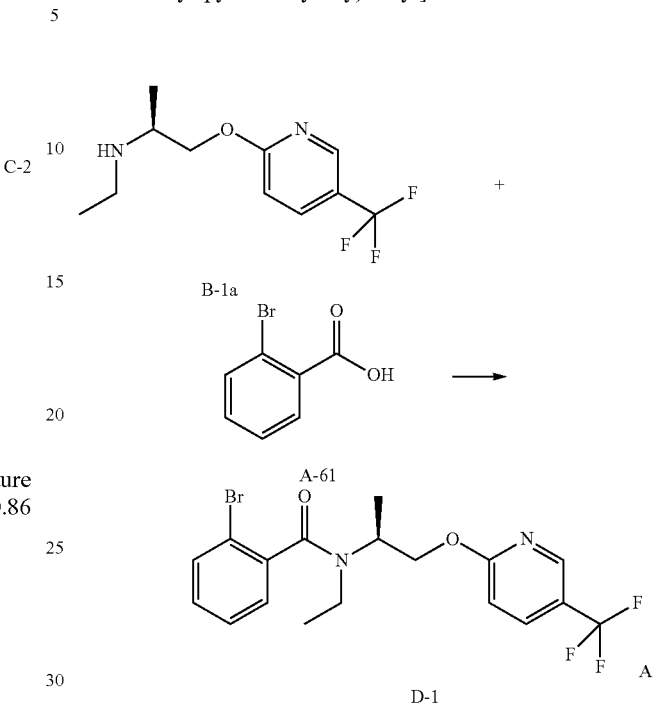

A mixture of A-61 (2.1 g, 11 mmol), B-1a (2.4 g, 9.7 mmol), DIPEA (5.0 mL, 29 mmol) and CIP (3.5 g, 13 mmol) in ACN (50 mL) is stirred at RT for 1 h. The mixture is concentrated and the crude product is purified by HPLC-MS (using a solvent gradient H₂O/ACN with NH₃) to provide 3.1 g of D-1. ESI-MS: 431 [M+H]⁺; HPLC (Rt): 1.16 min (method F).

N—[(S)-2-(5-Bromo-pyridin-2-yloxy)-1-methyl-ethyl]-N-ethyl-3-fluoro-2-[1,2,3]triazol-2-yl-benzamide D-2

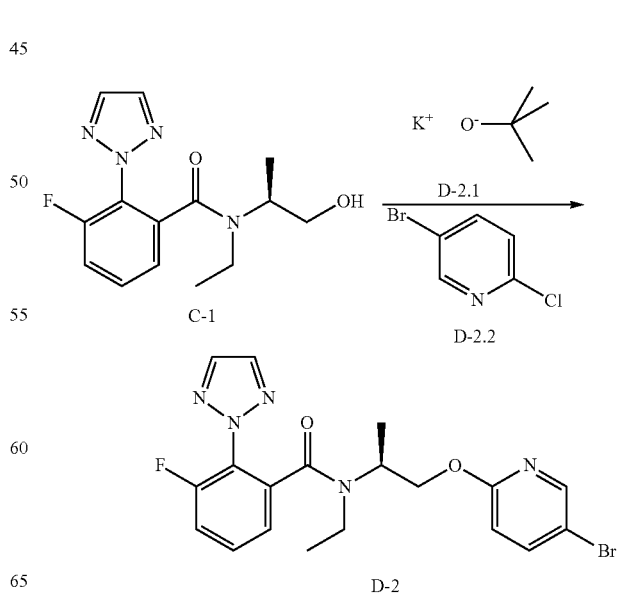

Under a nitrogen atmosphere, D-2.1 (46 mg, 0.41 mmol) is added to a mixture of C-1 (100 mg, 0.34 mmol) and D-2.2 (79 mg, 0.41 mmol) in dry DMSO. The mixture is stirred at RT overnight. Water is added to the reaction and the product is extracted with EA. The organic layer is separated, dried and solvent evaporated. The crude product is purified by flash column chromatography on silica gel (using a solvent gradient n-hexane/EA 10/0 to 5/5) to afford 75 mg of D-2. ESI-MS: 448 [M+H]$^+$; HPLC (Rt): 1.27 min (Method U).

N-Ethyl-2-fluoro-6-iodo-N—[(S)-1-methyl-2-(5-trifluoromethyl-pyridin-2-yloxy)-ethyl]-Benzamide
D-3

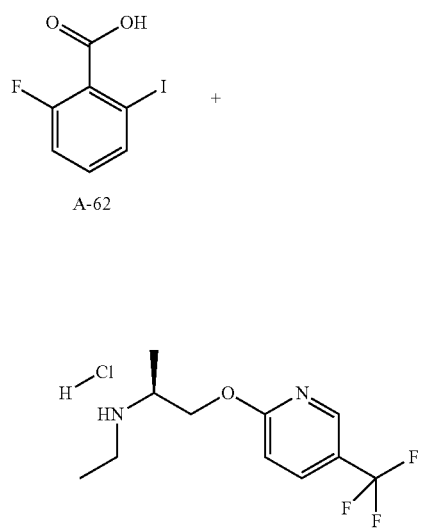

4-Methoxy-N—[(S)-1-methyl-2-(5-trifluoromethyl-pyridin-2-yloxy)-ethyl]-2-pyrimidin-2-yl-Benzamide
D-4

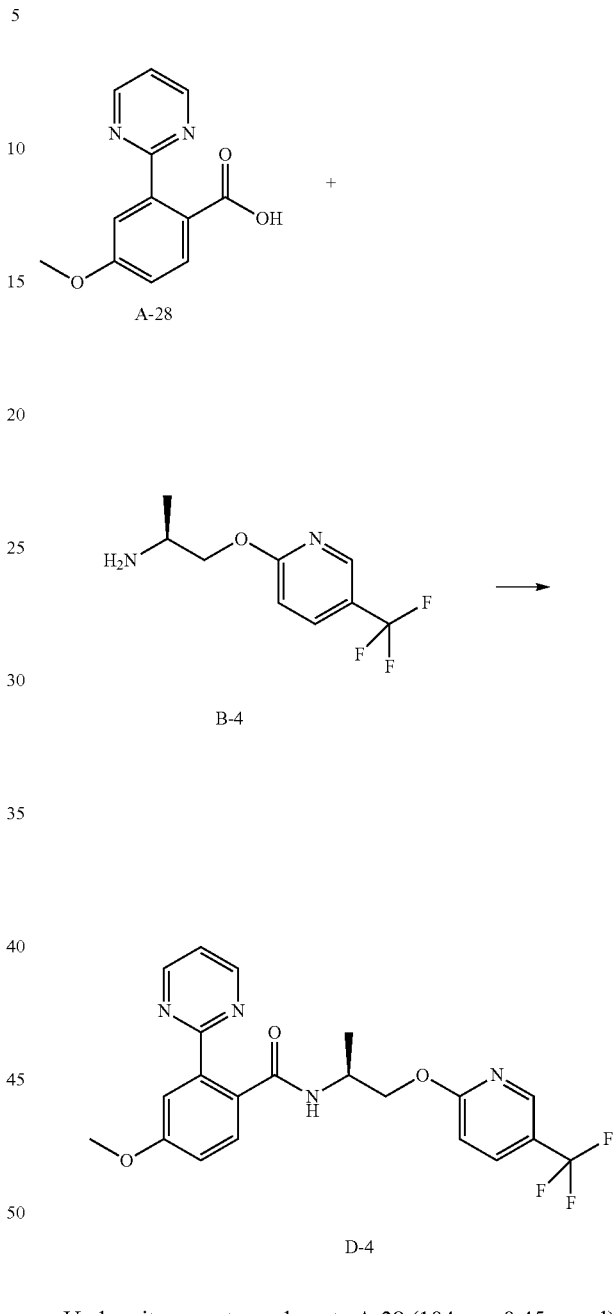

To A-62 (150 mg, 0.56 mmol) dissolved in dry DMF (4 mL) under a nitrogen atmosphere, TBTU (199 mg, 0.62 mmol) and DIPEA (290 µL, 1.7 mmol) are added. The mixture is stirred for 30 min at RT, then B-1a.HCl (177 mg, 0.62 mmol) is added and the mixture is stirred overnight. The crude mixture is poured into water and extracted with Et$_2$O. The organic layer is dried and the solvent evaporated. The crude product is purified by flash column chromatography on silica gel (using a solvent gradient cyclohexane/EA 10/0 to 8/2) to afford 210 mg of D-3. ESI-MS: 497 [M+H]$^+$; HPLC (Rt): 1.41 min (Method M).

Under nitrogen atmosphere to A-28 (104 mg, 0.45 mmol) in dry DMF (2 mL) are added B-4 (100 mg, 0.45 mmol), HATU (206 mg, 1.2 mmol) and DIPEA (232 µL, 1.4 mmol). The mixture is stirred at RT for 3 h. Water is added to the reaction and the product is extracted with EA. The organic layer is washed with brine, separated, dried and concentrated. The crude product is directly purified by preparative LCMS to afford 80 mg of D-4. ESI-MS: 433 [M+H]$^+$; HPLC (Rt): 1.07 min (Method M).

The following examples are prepared in analogy to the above described procedure adjusting the purification conditions: the crude product is purified by flash column chromatography on silica gel.

| Example | Structure | ESI-MS [M + H]⁺ | HPLC (Rt) [min] | HPLC method |
|---|---|---|---|---|
| D-5 | 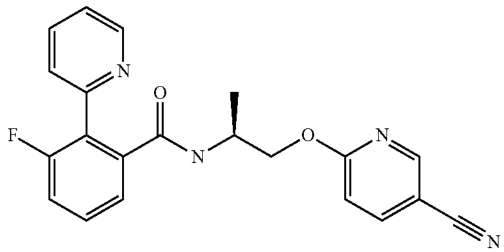 [SMILES: C[C@@H](COc1ccc(C#N)cn1)NC(=O)c1cccc(F)c1-c1ccccn1] | 378 | 0.83 | M |
| D-6 | 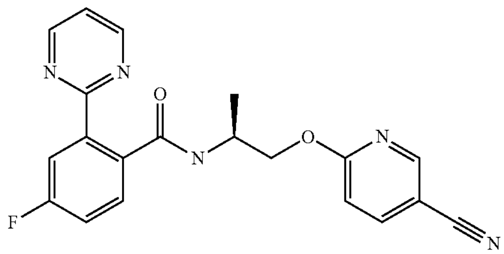 [SMILES: C[C@@H](COc1ccc(C#N)cn1)NC(=O)c1ccc(F)cc1-c1ncccn1] | 378 | 0.87 | M |
| D-7 | 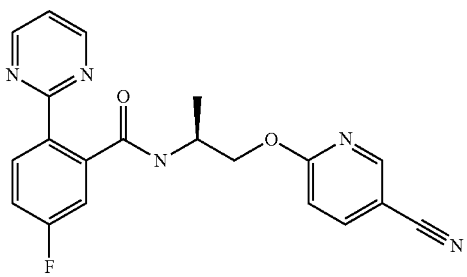 [SMILES: C[C@@H](COc1ccc(C#N)cn1)NC(=O)c1cc(F)ccc1-c1ncccn1] | 378 | 0.90 | M |

Preparation of Compounds of the Present Invention

Example 1

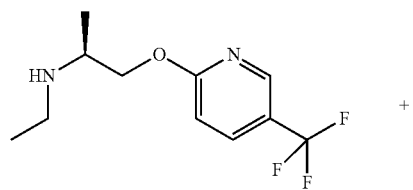

B-1a

+

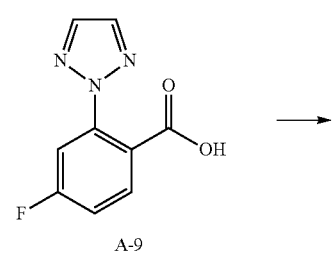

A-9

-continued

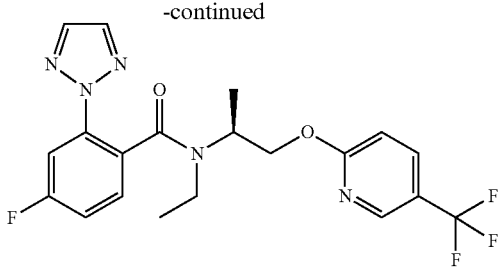

Example 1

To a mixture of A-9 (2.1 mg, 0.010 mmol) and DIPEA (5 μL, 0.030 mmol) in ACN (85 μL) is added a mixture of B-1a (2.5 mg, 0.010 mmol) in ACN (100 μL) and CIP (3.6 mg, 0.013 mmol) in ACN (50 μL). The reaction is stirred overnight, then DMF (50 μL) and 3 M aq. K₂OO₃ (15 μL) is added and the mixture is shaken for 20 min. The mixture is filtered through basic alumina, washed with DMF/MeOH=9/1 and concentrated to provide 3.9 mg of Example 1. ESI-MS: 438 [M+H]⁺; HPLC (Rt): 1.03 min (method R).

The following examples are prepared in analogy to the above described procedure using the corresponding acid (see Acid Intermediates) and amine (see Amine Intermediates) as described before. Example 27 was stirred for 4 h instead of overnight.

| Example | Structure | ESI-MS [M + H]+ | HPLC (Rt) [min] | HPLC method |
|---|---|---|---|---|
| 3 | 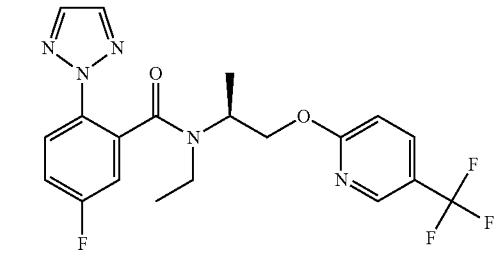 [SMILES: CCN(C(=O)c1cc(F)ccc1-n1nccn1)[C@@H](C)COc1ccc(C(F)(F)F)cn1] | 438 | 1.02 | R |
| 4 | 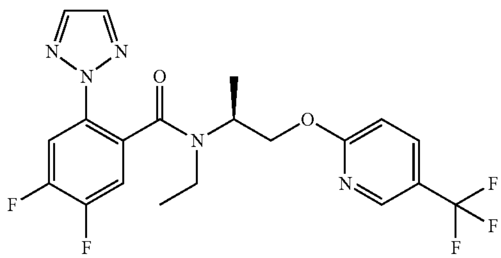 | 456 | 1.05 | R |
| 8 | 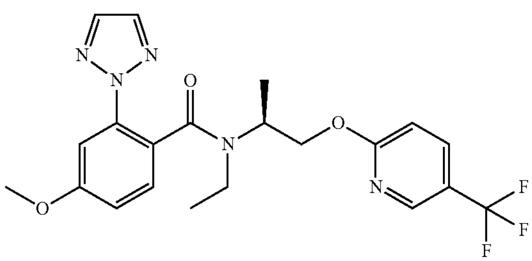 [SMILES: CCN(C(=O)c1ccc(OC)cc1-n1nccn1)[C@@H](C)COc1ccc(C(F)(F)F)cn1] | 450 | 1.01 | R |
| 10 | 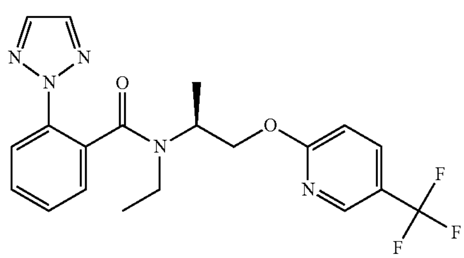 [SMILES: CCN(C(=O)c1ccccc1-n1nccn1)[C@@H](C)COc1ccc(C(F)(F)F)cn1] | 420 | 0.99 | R |
| 13 | 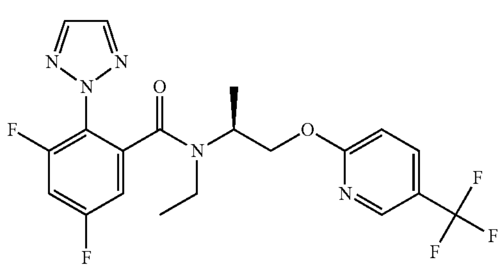 [SMILES: CCN(C(=O)c1cc(F)cc(F)c1-n1nccn1)[C@@H](C)COc1ccc(C(F)(F)F)cn1] | 478 (M + Na)+ | 1.03 | R |
| 14 | 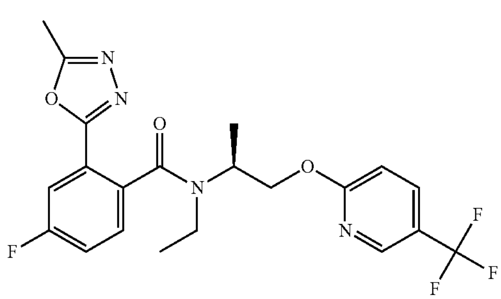 [SMILES: CCN(C(=O)c1ccc(F)cc1-c1nnc(C)o1)[C@@H](C)COc1ccc(C(F)(F)F)cn1] | 475 (M + Na)+ | 0.94 | R |

-continued

| Example | Structure | ESI-MS [M + H]+ | HPLC (Rt) [min] | HPLC method |
|---|---|---|---|---|
| 15 | 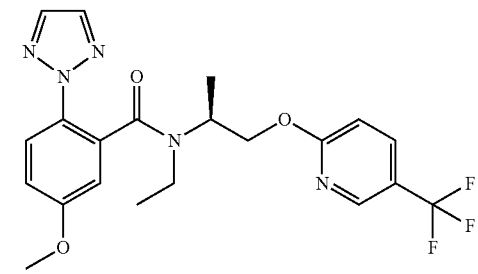 [SMILES: CCN(C(=O)c1cc(OC)ccc1-n1nccn1)[C@@H](C)COc1ccc(C(F)(F)F)cn1] | 450 | 1.01 | R |
| 18 | 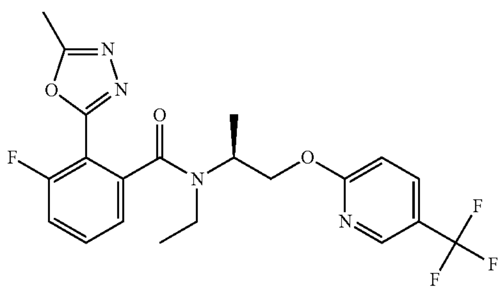 [SMILES: CCN(C(=O)c1cccc(F)c1-c1nnc(C)o1)[C@@H](C)COc1ccc(C(F)(F)F)cn1] | 475 (M + Na)+ | 0.92 | R |
| 20 | 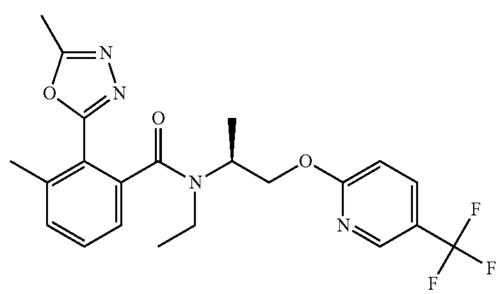 [SMILES: CCN(C(=O)c1cccc(C)c1-c1nnc(C)o1)[C@@H](C)COc1ccc(C(F)(F)F)cn1] | 471 (M + Na)+ | 0.96 | R |
| 22 | 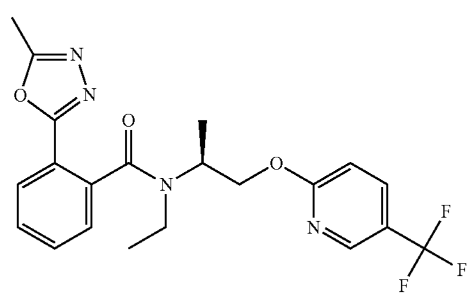 [SMILES: CCN(C(=O)c1ccccc1-c1nnc(C)o1)[C@@H](C)COc1ccc(C(F)(F)F)cn1] | 457 (M + Na)+ | 0.91 | R |
| 26 | 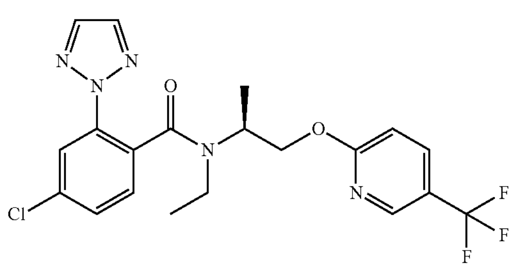 [SMILES: CCN(C(=O)c1ccc(Cl)cc1-n1nccn1)[C@@H](C)COc1ccc(C(F)(F)F)cn1] | 454 | 1.09 | R |

| Example | Structure | ESI-MS [M + H]+ | HPLC (Rt) [min] | HPLC method |
|---|---|---|---|---|
| 127 | 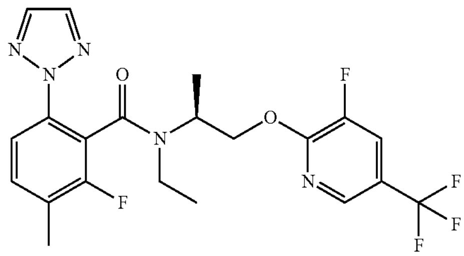 [SMILES: CCN(C(=O)c1c(-n2nccn2)ccc(C)c1F)[C@@H](C)COc1ncc(C(F)(F)F)cc1F] | 470 | 1.04 | V |
| 132 | 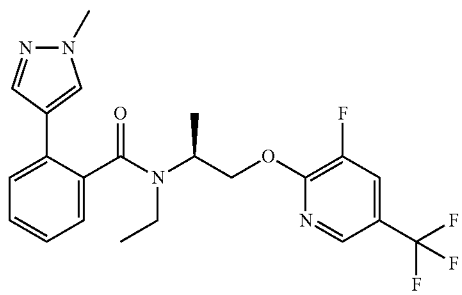 [SMILES: CCN(C(=O)c1ccccc1-c1cnn(C)c1)[C@@H](C)COc1ncc(C(F)(F)F)cc1F] | 473 [M + Na]+ | 0.95 | V |
| 124 | 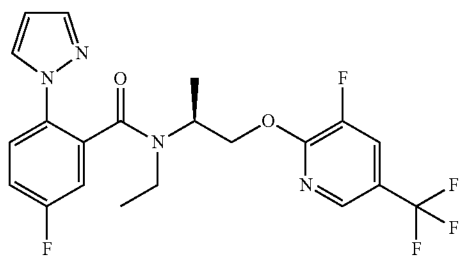 [SMILES: CCN(C(=O)c1cc(F)ccc1-n1cccn1)[C@@H](C)COc1ncc(C(F)(F)F)cc1F] | 477 [M + Na]+ | 1.03 | V |

Example 46

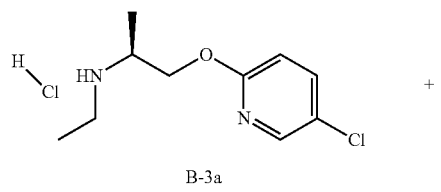

B-3a

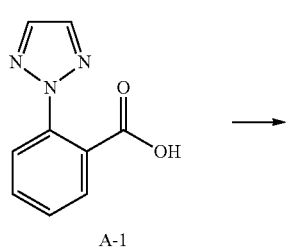

A-1

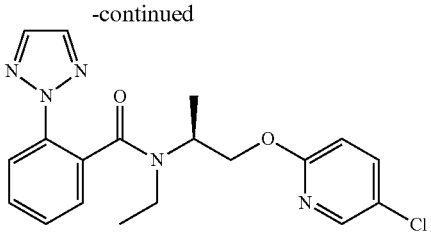

Example 46

To a mixture of A-1 (19 mg, 0.10 mmol), B-3a (21 mg, 0.085 mmol) and DIPEA (44 µL) in ACN (3 mL) is added CIP (31 mg, 0.11 mmol) and the mixture is stirred overnight. DMF (1 mL) is added and the product is directly purified from this mixture by HPLC-MS (using a solvent gradient H₂O/ACN with NH₄OH) to provide 19 mg of Example 46. ESI-MS: 386 [M+H]+; HPLC (Rt): 0.95 min (method R).

The following examples are prepared in analogy to the above described procedure using the corresponding acid (see Acid Intermediates) and amine (see Amine Intermediates) as described before, adjusting the reaction conditions: 30 min at 65° C. for Examples 117, 120, 125, 129, 130; 2 h at RT for Examples 121, 126

| Example | Structure | ESI-MS [M + H]+ | HPLC (Rt) [min] | HPLC method |
|---|---|---|---|---|
| 28 | 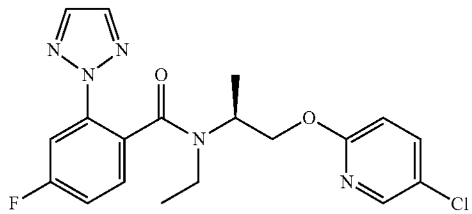 [SMILES: CCN(C(=O)c1ccc(F)cc1-n1nccn1)[C@@H](C)COc1ccc(Cl)cn1] | 404 | 0.99 | R |
| 29 | 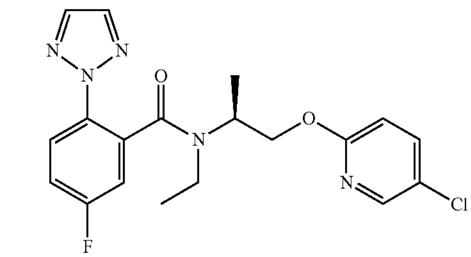 [SMILES: CCN(C(=O)c1cc(F)ccc1-n1nccn1)[C@@H](C)COc1ccc(Cl)cn1] | 404 | 0.98 | R |
| 30 | 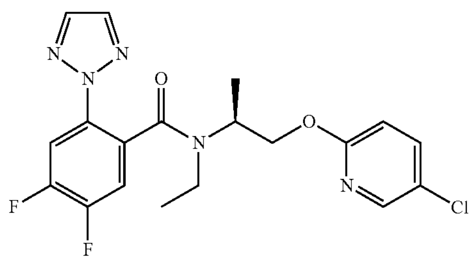 [SMILES: CCN(C(=O)c1cc(F)c(F)cc1-n1nccn1)[C@@H](C)COc1ccc(Cl)cn1] | 422 | 1.03 | R |
| 32 | 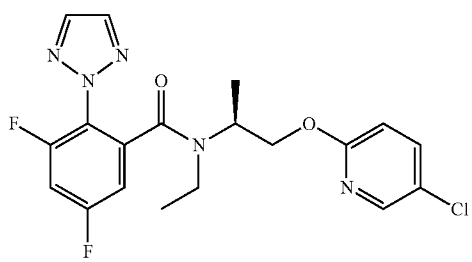 [SMILES: CCN(C(=O)c1cc(F)cc(F)c1-n1nccn1)[C@@H](C)COc1ccc(Cl)cn1] | 422 | 0.99 | R |
| 33 | 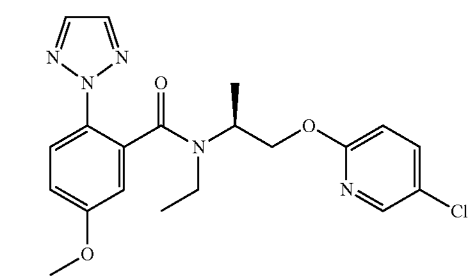 [SMILES: CCN(C(=O)c1cc(OC)ccc1-n1nccn1)[C@@H](C)COc1ccc(Cl)cn1] | 416 | 0.96 | R |
| 36 | 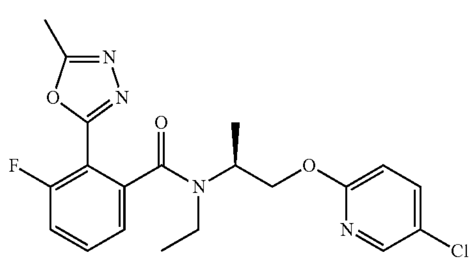 [SMILES: CCN(C(=O)c1cccc(F)c1-c1nnc(C)o1)[C@@H](C)COc1ccc(Cl)cn1] | 419 | 0.88 | R |

-continued

| Example | Structure | ESI-MS [M + H]+ | HPLC (Rt) [min] | HPLC method |
|---|---|---|---|---|
| 38 | 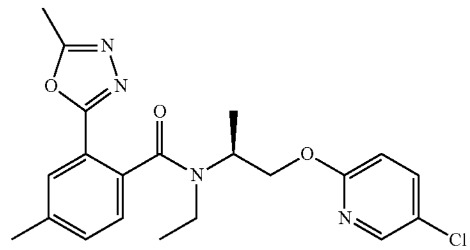 [SMILES: CCN(C(=O)c1ccc(C)cc1-c1nnc(C)o1)[C@@H](C)COc1ccc(Cl)cn1] | 415 | 0.92 | R |
| 39 | 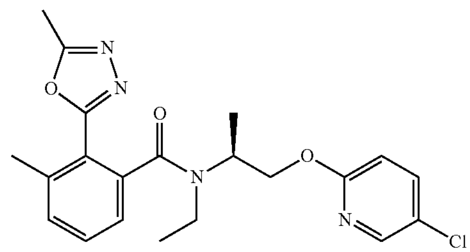 [SMILES: CCN(C(=O)c1cccc(C)c1-c1nnc(C)o1)[C@@H](C)COc1ccc(Cl)cn1] | 415 | 0.91 | R |
| 45 | 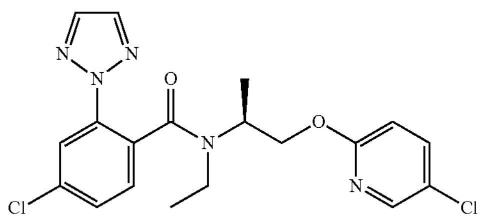 [SMILES: CCN(C(=O)c1ccc(Cl)cc1-n1nccn1)[C@@H](C)COc1ccc(Cl)cn1] | 421 | 1.06 | R |
| 47 | 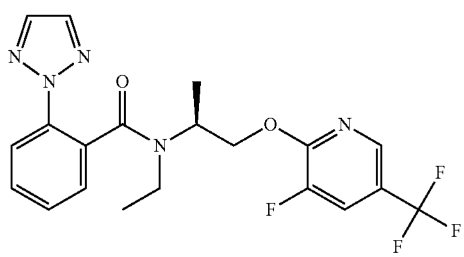 [SMILES: CCN(C(=O)c1ccccc1-n1nccn1)[C@@H](C)COc1ncc(C(F)(F)F)cc1F] | 438 | 0.94 | T |
| 48 | 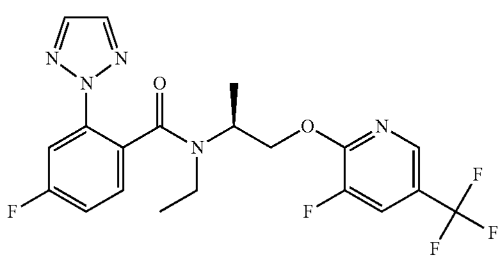 [SMILES: CCN(C(=O)c1ccc(F)cc1-n1nccn1)[C@@H](C)COc1ncc(C(F)(F)F)cc1F] | 456 | 0.97 | T |
| 49 | 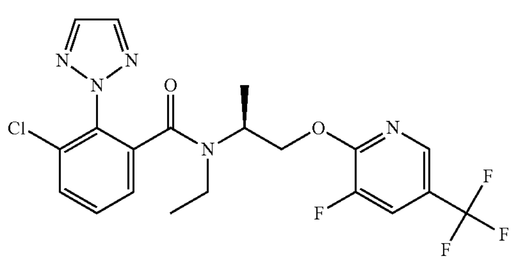 [SMILES: CCN(C(=O)c1cccc(Cl)c1-n1nccn1)[C@@H](C)COc1ncc(C(F)(F)F)cc1F] | 472 | 0.96 | T |

-continued

| Example | Structure | ESI-MS [M + H]+ | HPLC (Rt) [min] | HPLC method |
|---|---|---|---|---|
| 50 | 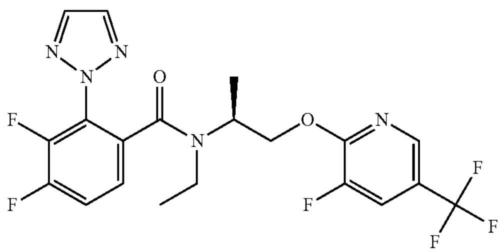 [SMILES: CCN(C(=O)c1ccc(F)c(F)c1-n1nccn1)[C@@H](C)COc1ncc(C(F)(F)F)cc1F] | 474 | 0.96 | T |
| 51 | 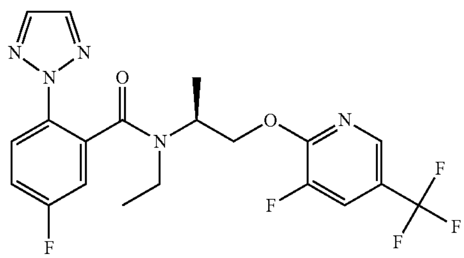 [SMILES: CCN(C(=O)c1cc(F)ccc1-n1nccn1)[C@@H](C)COc1ncc(C(F)(F)F)cc1F] | 456 | 0.96 | T |
| 52 | 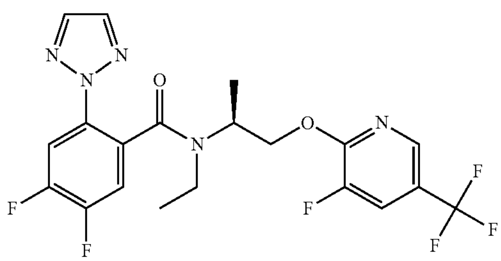 [SMILES: CCN(C(=O)c1cc(F)c(F)cc1-n1nccn1)[C@@H](C)COc1ncc(C(F)(F)F)cc1F] | 474 | 0.99 | T |
| 54 | 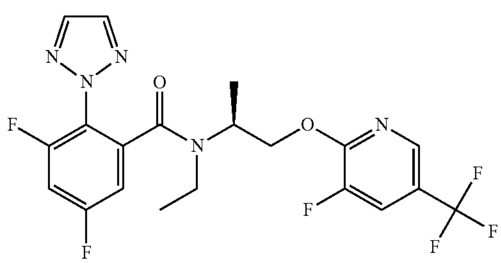 [SMILES: CCN(C(=O)c1cc(F)cc(F)c1-n1nccn1)[C@@H](C)COc1ncc(C(F)(F)F)cc1F] | 474 | 0.96 | T |
| 55 | 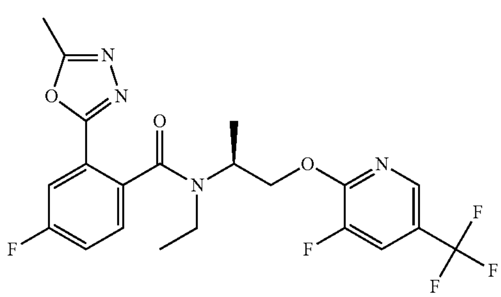 [SMILES: CCN(C(=O)c1ccc(F)cc1-c1nnc(C)o1)[C@@H](C)COc1ncc(C(F)(F)F)cc1F] | 471 | 0.89 | T |

-continued

| Example | Structure | ESI-MS [M + H]+ | HPLC (Rt) [min] | HPLC method |
|---|---|---|---|---|
| 56 | 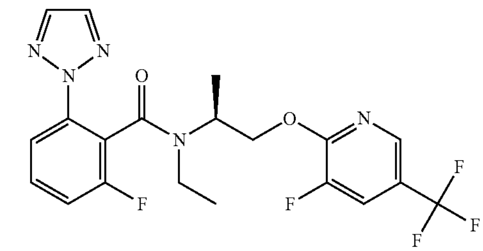 [SMILES: CCN(C(=O)c1c(F)cccc1-n1nccn1)[C@@H](C)COc1ncc(C(F)(F)F)cc1F] | 456 | 0.99 | T |
| 57 | 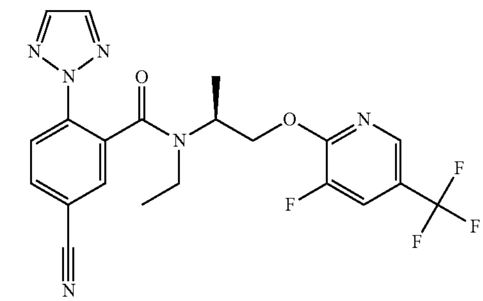 [SMILES: CCN(C(=O)c1cc(C#N)ccc1-n1nccn1)[C@@H](C)COc1ncc(C(F)(F)F)cc1F] | 463 | 0.91 | T |
| 61 | 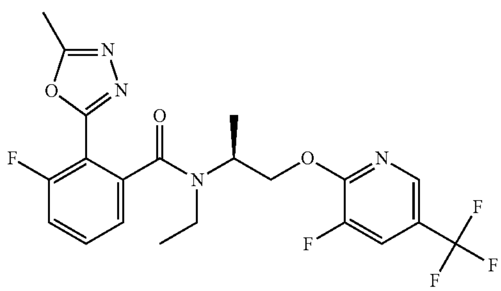 [SMILES: CCN(C(=O)c1cccc(F)c1-c1nnc(C)o1)[C@@H](C)COc1ncc(C(F)(F)F)cc1F] | 471 | 0.88 | T |
| 64 | 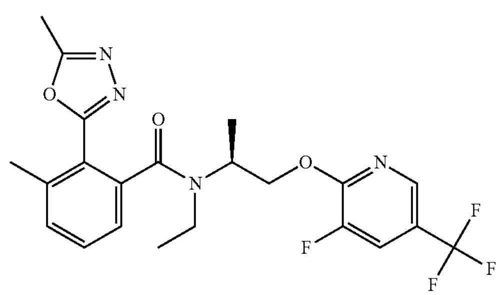 [SMILES: CCN(C(=O)c1cccc(C)c1-c1nnc(C)o1)[C@@H](C)COc1ncc(C(F)(F)F)cc1F] | 467 | 0.91 | T |
| 68 | 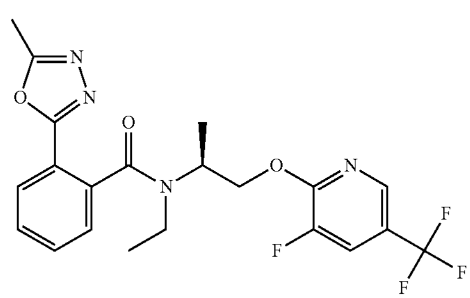 [SMILES: CCN(C(=O)c1ccccc1-c1nnc(C)o1)[C@@H](C)COc1ncc(C(F)(F)F)cc1F] | 453 | 0.87 | T |

-continued

| Example | Structure | ESI-MS [M + H]+ | HPLC (Rt) [min] | HPLC method |
|---|---|---|---|---|
| 69 | 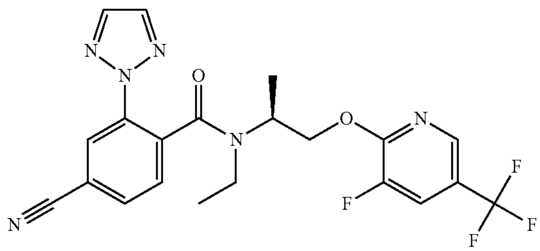 [SMILES: CCN(C(=O)c1ccc(C#N)cc1-n1nccn1)[C@@H](C)COc1ncc(C(F)(F)F)cc1F] | 463 | 0.92 | T |
| 73 | 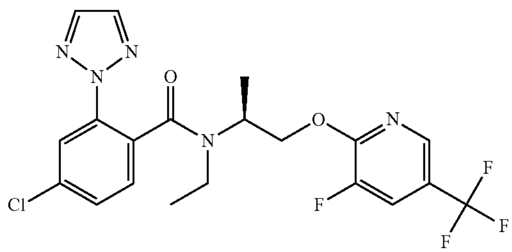 [SMILES: CCN(C(=O)c1ccc(Cl)cc1-n1nccn1)[C@@H](C)COc1ncc(C(F)(F)F)cc1F] | 472 | 1.02 | T |
| 114 | 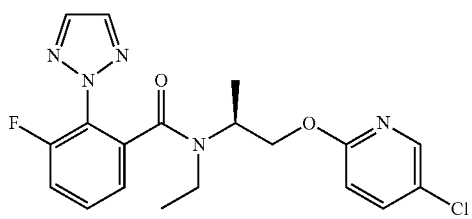 [SMILES: CCN(C(=O)c1cccc(F)c1-n1nccn1)[C@@H](C)COc1ccc(Cl)cn1] | 404 | 1.08 | F |
| 134 | 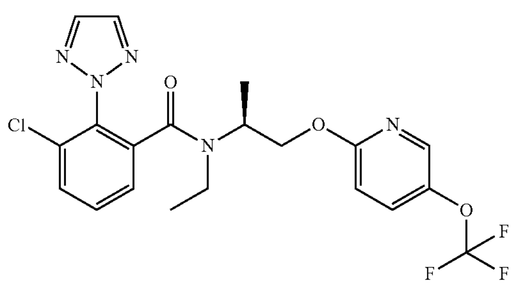 [SMILES: CCN(C(=O)c1cccc(Cl)c1-n1nccn1)[C@@H](C)COc1ccc(OC(F)(F)F)cn1] | 470 | 1.16 | F |
| 130 | 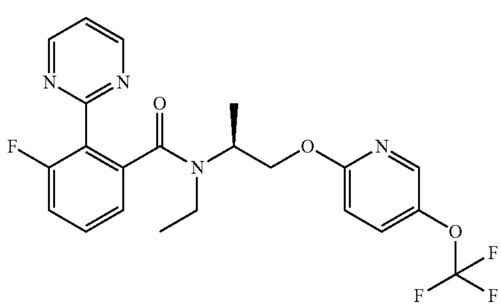 [SMILES: CCN(C(=O)c1cccc(F)c1-c1ncccn1)[C@@H](C)COc1ccc(OC(F)(F)F)cn1] | 465 | 1.11 | F |

-continued

| Example | Structure | ESI-MS [M + H]+ | HPLC (Rt) [min] | HPLC method |
|---|---|---|---|---|
| 126 | 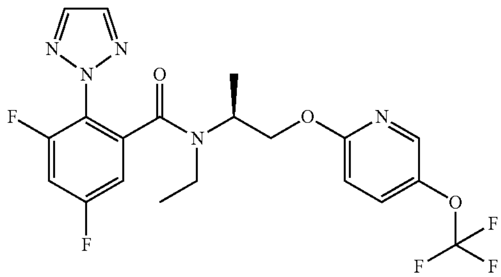 [SMILES: CCN(C(=O)c1cc(F)cc(F)c1-n1nccn1)[C@@H](C)COc1ccc(OC(F)(F)F)cn1] | 472 | 1.16 | F |
| 121 | 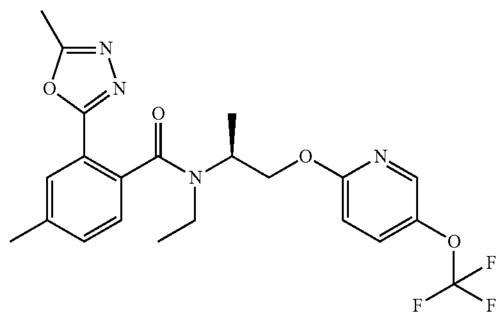 [SMILES: CCN(C(=O)c1ccc(C)cc1-c1nnc(C)o1)[C@@H](C)COc1ccc(OC(F)(F)F)cn1] | 465 | 1.12 | F |
| 129 | 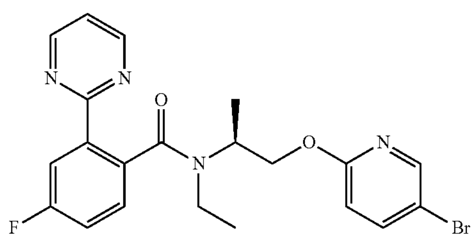 [SMILES: CCN(C(=O)c1ccc(F)cc1-c1ncccn1)[C@@H](C)COc1ccc(Br)cn1] | 459 | 1.13 | F |
| 117 | 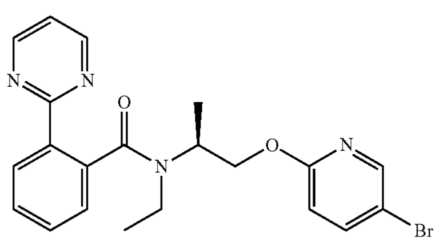 [SMILES: CCN(C(=O)c1ccccc1-c1ncccn1)[C@@H](C)COc1ccc(Br)cn1] | 441 | 1.11 | F |
| 120 | 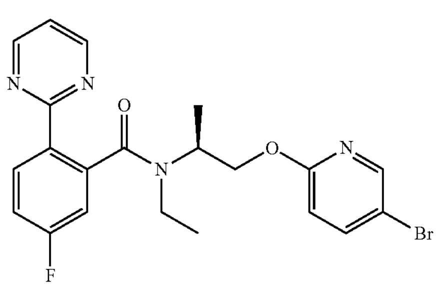 [SMILES: CCN(C(=O)c1cc(F)ccc1-c1ncccn1)[C@@H](C)COc1ccc(Br)cn1] | 459 | 1.13 | F |

| Example | Structure | ESI-MS [M + H]+ | HPLC (Rt) [min] | HPLC method |
|---|---|---|---|---|
| 125 | 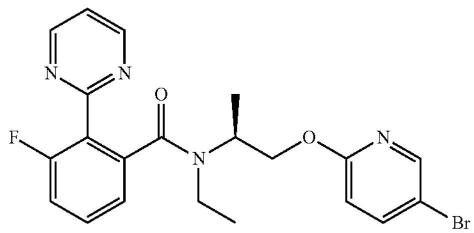 [SMILES: CCN(C(=O)c1cccc(F)c1-c1ncccn1)[C@@H](C)COc1ccc(Br)cn1] | 459 | 1.08 | F |

Example 90

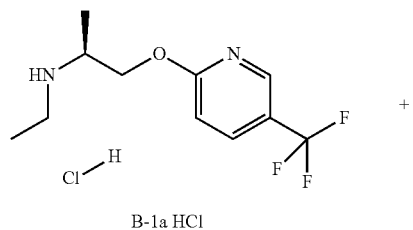

B-1a HCl

+

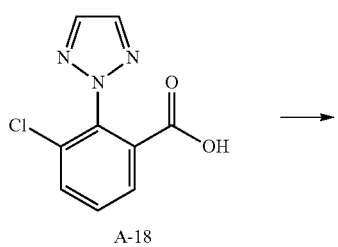

A-18

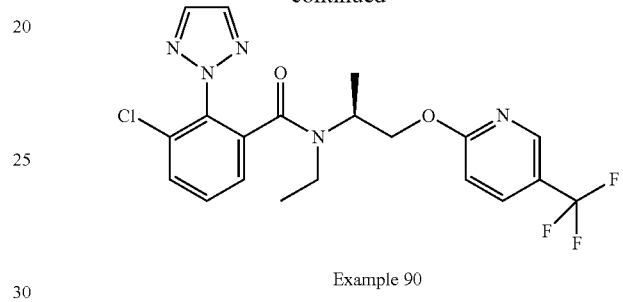

Example 90

To a mixture of A-18 (22 mg, 0.10 mmol), B-1a.HCl (25 mg, 0.09 mmol) and DIPEA (46 µL) in ACN (2 mL) is added CIP (32 mg, 0.11 mmol) and the mixture is stirred for 1 h. DMF (1 mL) is added and the mixture purified by HPLC-MS (using a solvent gradient $H_2O$/ACN with $NH_4OH$) to provide 40 mg of Example 90. ESI pos.+neg. (Loop-Inj.): 454 [M+H]+; HPLC (Rt): 1.13 min (method F).

The following examples are prepared in analogy to the above described procedure using the corresponding acid (see Acid Intermediates) and amine (see Amine Intermediates) as described before:

| Example | Structure | ESI-MS [M + H]+ | HPLC (Rt) [min] | HPLC method |
|---|---|---|---|---|
| 95 | 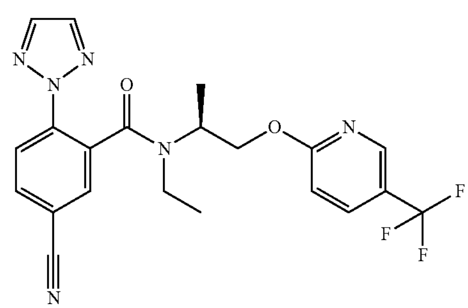 [SMILES: CCN(C(=O)c1cc(C#N)ccc1-n1nccn1)[C@@H](C)COc1ccc(C(F)(F)F)cn1] | 445 | 1.09 | F |

-continued

| Example | Structure | ESI-MS [M + H]+ | HPLC (Rt) [min] | HPLC method |
|---|---|---|---|---|
| 103 | 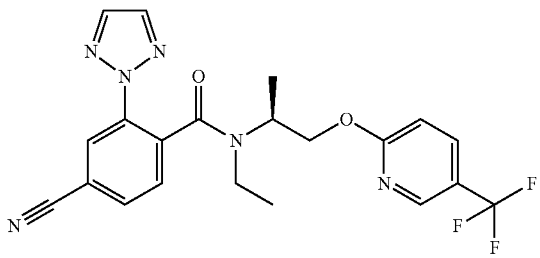 [SMILES: CCN(C(=O)c1ccc(C#N)cc1-n1nccn1)[C@@H](C)COc1ccc(C(F)(F)F)cn1] | 445 | 1.10 | F |
| 91 | 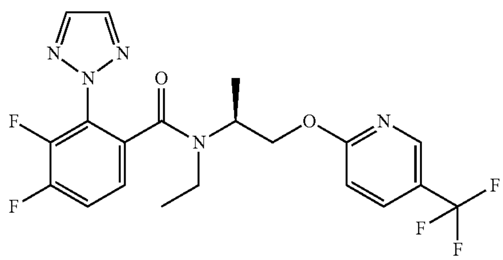 [SMILES: CCN(C(=O)c1ccc(F)c(F)c1-n1nccn1)[C@@H](C)COc1ccc(C(F)(F)F)cn1] | 456 | 1.17 | F |
| 92 | 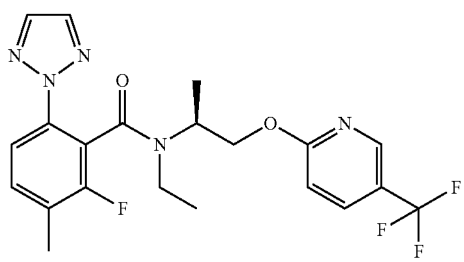 [SMILES: CCN(C(=O)c1c(-n2nccn2)ccc(C)c1F)[C@@H](C)COc1ccc(C(F)(F)F)cn1] | 452 | 1.14 | F |
| 93 | 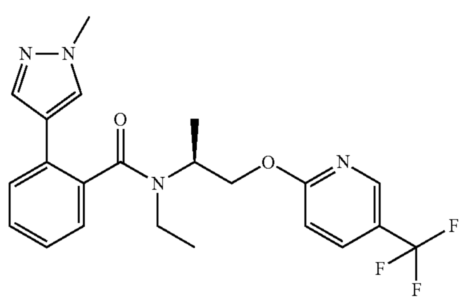 [SMILES: CCN(C(=O)c1ccccc1-c1cnn(C)c1)[C@@H](C)COc1ccc(C(F)(F)F)cn1] | 433 | 1.07 | F |
| 94 | 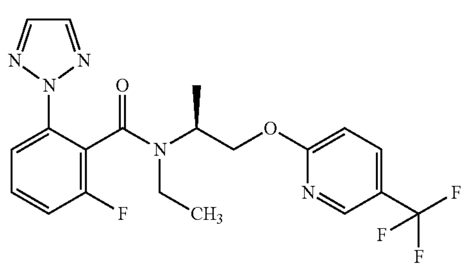 [SMILES: CCN(C(=O)c1c(F)cccc1-n1nccn1)[C@@H](C)COc1ccc(C(F)(F)F)cn1] | 438 | 1.13 | F |

Example 74

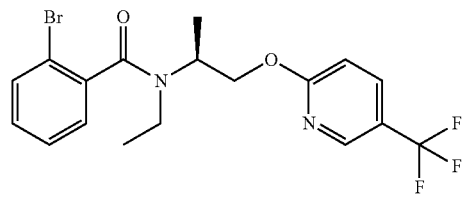

D-1

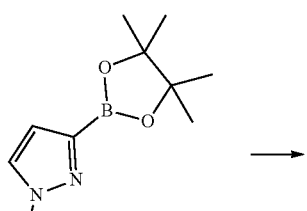

74.1

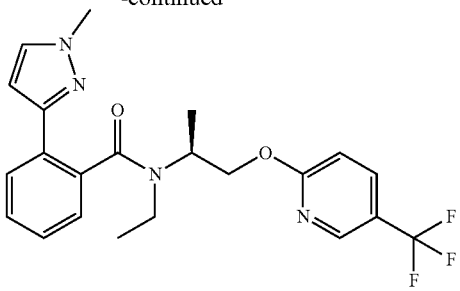

Example 74

A mixture of D-1 (43 mg, 0.10 mmol) in 1,4-dioxane (2.0 mL) is degassed for 15 min with Argon and 74.1 (31 mg, 0.15 mmol) and 3 M $K_2CO_3$ (133 µL, 0.40 mmol) is added. The mixture is flushed with argon and $Pd(dppf)Cl_2 \cdot DCM$ (8 mg, 0.01 mmol) is added and the reaction is stirred at 80° C. overnight. The mixture is filtered through a 1 mL SPE-Thiol-cartidge and basic alumina, washed with DMF/MeOH=9/1 and purified by HPLC-MS (using a solvent gradient $H_2O$/ACN with $NH_4OH$) to provide 17 mg of Example 74. ESI-MS: 433 [M+H]$^+$; HPLC (Rt): 0.92 min (Method T).

The following examples are prepared in analogy to the above described procedure using the corresponding amide (see Amide Intermediates) as described before.

| Example | Structure | ESI-MS [M + H]$^+$ | HPLC (Rt) [min] | HPLC Method |
|---|---|---|---|---|
| 76 | 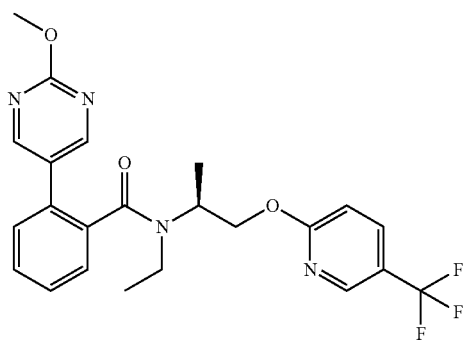 | 455 | 0.94 | T |
| 79 | 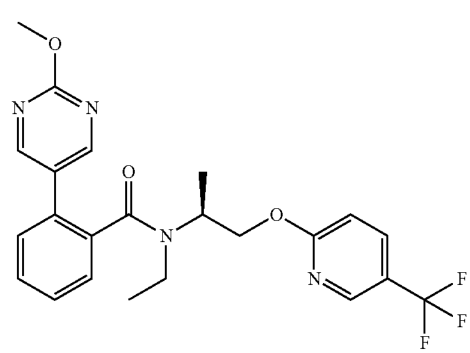 [SMILES: CCN(C(=O)c1ccccc1-c1cnc(OC)nc1)[C@@H](C)COc1ccc(C(F)(F)F)cn1] | 461 | 0.93 | T |

-continued

| Example | Structure | ESI-MS [M + H]+ | HPLC (Rt) [min] | HPLC Method |
|---|---|---|---|---|
| 81 | 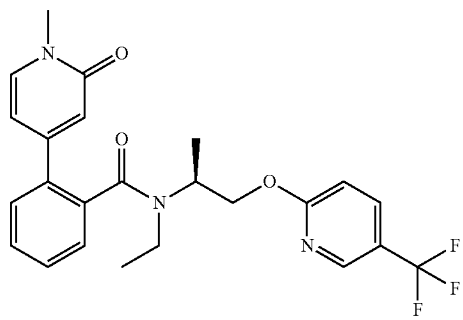 [SMILES: CCN(C(=O)c1ccccc1-c1ccn(C)c(=O)c1)[C@@H](C)COc1ccc(C(F)(F)F)cn1] | 460 | 0.82 | T |
| 84 | 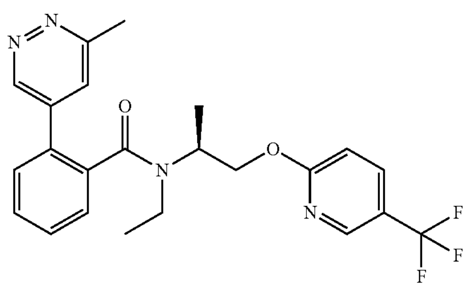 [SMILES: CCN(C(=O)c1ccccc1-c1cnnc(C)c1)[C@@H](C)COc1ccc(C(F)(F)F)cn1] | 445 | 0.79 | T |
| 85 | 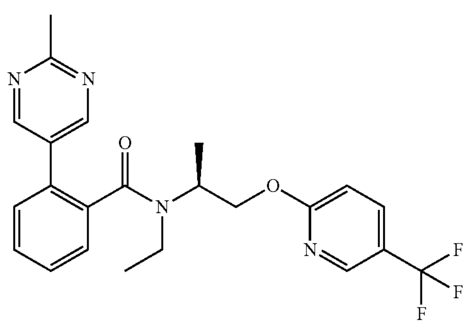 [SMILES: CCN(C(=O)c1ccccc1-c1cnc(C)nc1)[C@@H](C)COc1ccc(C(F)(F)F)cn1] | 445 | 0.89 | T |
| 96 | 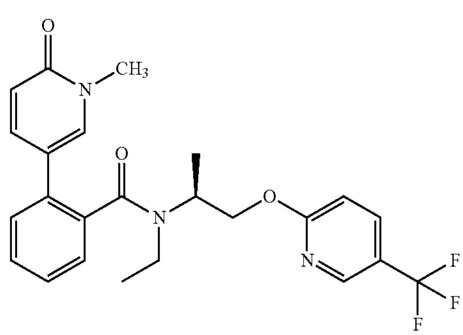 [SMILES: CCN(C(=O)c1ccccc1-c1ccc(=O)n(C)c1)[C@@H](C)COc1ccc(C(F)(F)F)cn1] | 460 | 0.84 | T |

Example 109

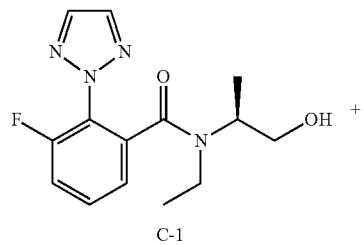

C-1

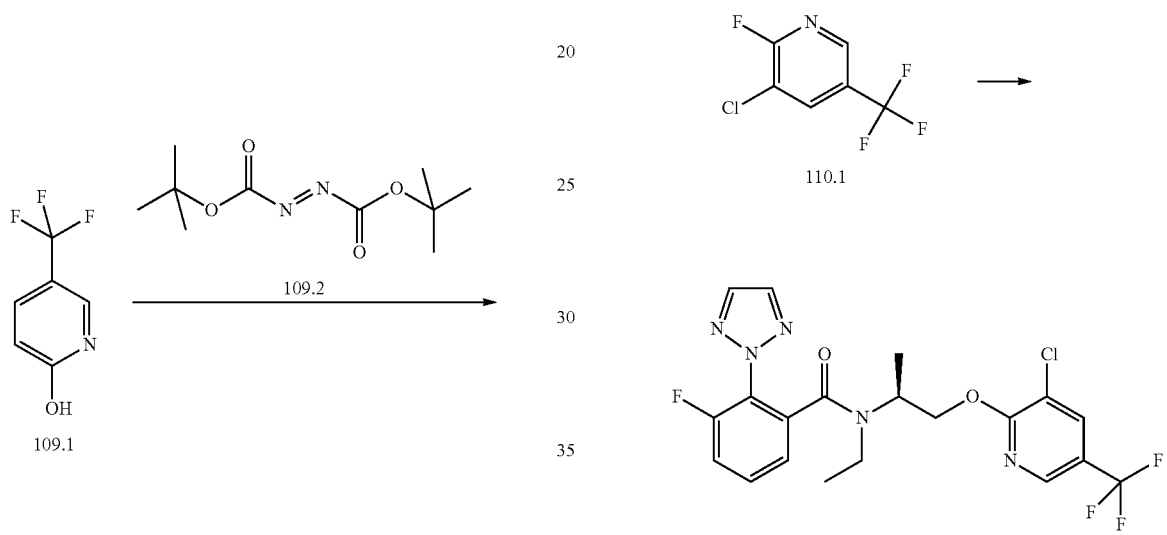

Ex 109

To a mixture of C-1 (100 mg, 0.31 mmol) in THF (3.0 mL) is added 109.1 (55 mg, 0.34 mmol) followed by PPh$_3$ (105 mg, 0.40 mmol) and 109.2 (80 mg, 0.34 mmol). The mixture is stirred at 60° C. for 6 hours, then cooled to RT and MeOH (1.0 mL) is added. The mixture is filtered and directly purified by HPLC-MS (using a solvent gradient H$_2$O/ACN with NH$_4$OH) to provide 31 mg of Example 109. ESI-MS: 438 [M+H]$^+$; HPLC (Rt): 0.77 min (method H).

Example 110

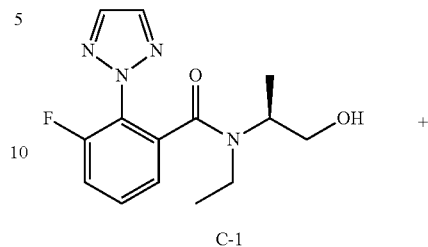

C-1

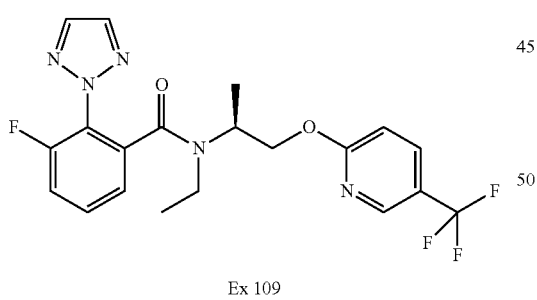

Example 110

To a mixture of C-1 (40 mg, 0.14 mmol) in dry DMF (2.0 mL) under a nitrogen atmosphere is added NaH (60% disp. in mineral oil, 6.6 mg, 0.16 mmol). After 30 min 110.1 (33 mg, 0.16 mmol) is added and stirring is continued overnight. Water is added and the mixture is extracted with EA. The combined organic phases are dried and concentrated. The crude product is purified by preparative HPLC-MS (using a solvent gradient H$_2$O/ACN with HCOOH) to provide 38 mg of Example 110. ESI-MS: 494 [M+Na]$^+$; HPLC (Rt): 3.94 min (Method N).

The following example is prepared in analogy to the above described procedure using the corresponding alcohol (see Alcohol Intermediates) as described before and the corresponding aryl halide, adjusting the purification conditions: the crude product is purified by flash column chromatography on silica gel (Example 131 and 133), or adjusting reaction times: 4 h for Example 133, overnight for Example 113:

| Example | Structure | ESI-MS [M + H]+ | HPLC (Rt) [min] | HPLC method |
|---|---|---|---|---|
| 111 | 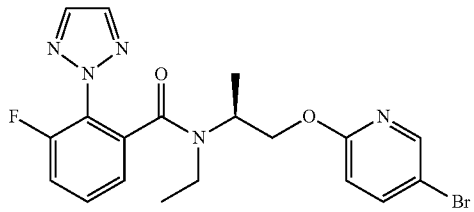 [SMILES: CCN(C(=O)c1cccc(F)c1-n1nccn1)[C@@H](C)COc1ccc(Br)cn1] | 470 [M + Na]+ | 3.78 | N |
| 112 | 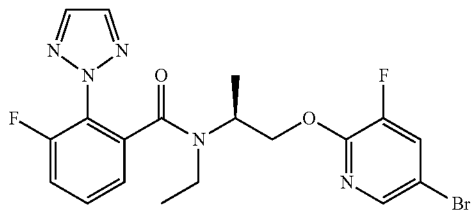 [SMILES: CCN(C(=O)c1cccc(F)c1-n1nccn1)[C@@H](C)COc1ncc(Br)cc1F] | 466 | 5.01 | O |
| 113 | 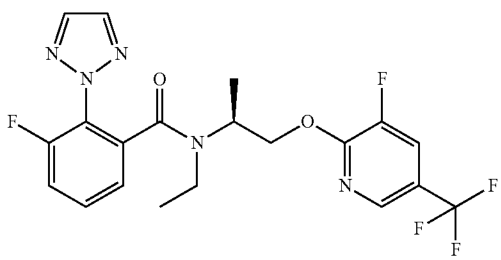 [SMILES: CCN(C(=O)c1cccc(F)c1-n1nccn1)[C@@H](C)COc1ncc(C(F)(F)F)cc1F] | 478 [M + Na]+ | 3.81 | N |
| 109 | 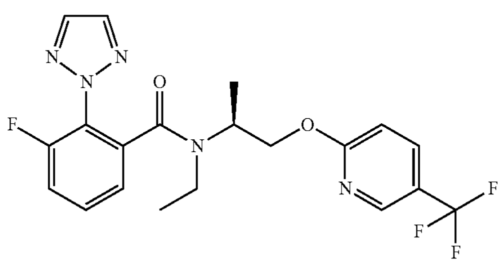 [SMILES: CCN(C(=O)c1cccc(F)c1-n1nccn1)[C@@H](C)COc1ccc(C(F)(F)F)cn1] | 438 | 0.77 | H |
| 131 | 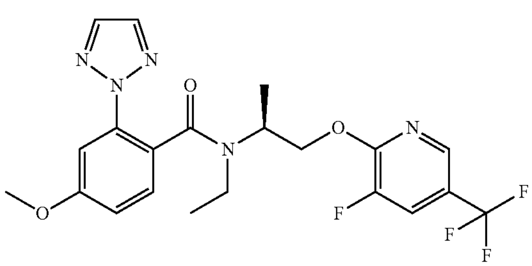 [SMILES: CCN(C(=O)c1ccc(OC)cc1-n1nccn1)[C@@H](C)COc1ncc(C(F)(F)F)cc1F] | 468 | 5.30 | O |
| 133 | 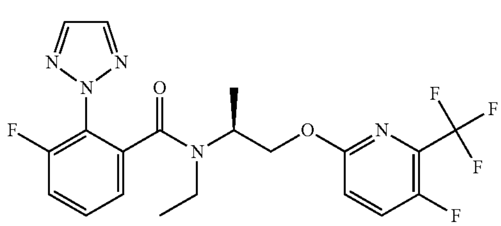 [SMILES: CCN(C(=O)c1cccc(F)c1-n1nccn1)[C@@H](C)COc1ccc(F)c(C(F)(F)F)n1] | 456 | 3.81 | N |

Example 118

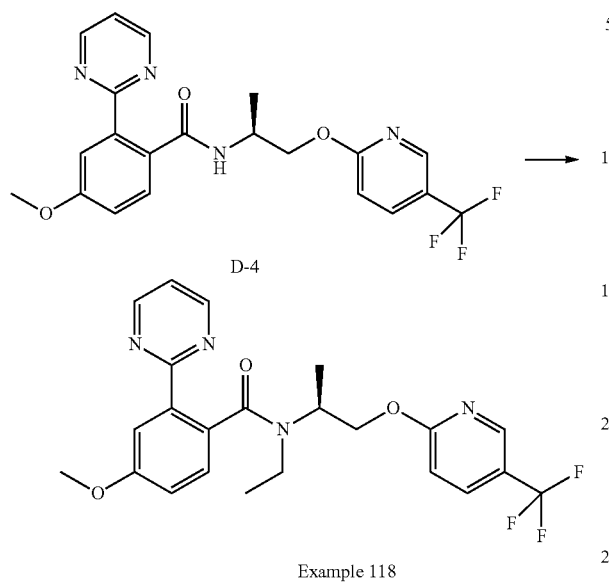

To a mixture of D-4 (80 mg, 0.15 mmol) and ethyl iodide (24 μL, 0.30 mmol) in dry DMF (2 mL) at RT and under nitrogen is added NaH (60% disp. in mineral oil, 12 mg, 0.30 mmol). The mixture is stirred for 3 h, then water is added and the product is extracted with EA. The organic layer is separated, dried and concentrated. The crude product is purified by flash column chromatography on silica gel (using a solvent gradient cyclohexane/EA from 8/2 to 0/10) to afford 47 mg of Example 118. ESI-MS: 483 [M+Na]$^+$; HPLC (Rt): 3.70 min (Method N).

The following examples are prepared in analogy to the above described procedure using the corresponding amide (see Amide Intermediates) as described before, adjusting using Et$_2$O or EA for the extraction:

| Example | Structure | ESI-MS [M + H]$^+$ | HPLC (Rt) [min] | HPLC method |
|---|---|---|---|---|
| 97 | 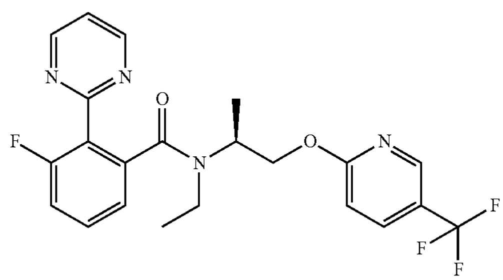 | 449 | 4.72 | O |
| 101 | 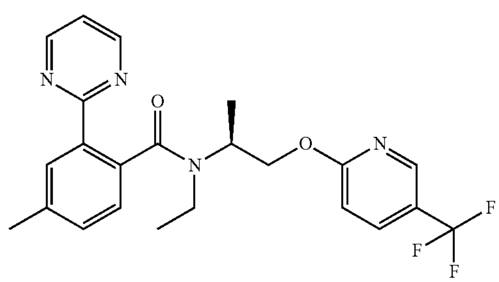 [SMILES: CCN(C(=O)c1ccc(C)cc1-c1ncccn1)[C@@H](C)COc1ccc(C(F)(F)F)cn1] | 467 [M + Na]$^+$ | 3.91 | N |
| 102 | 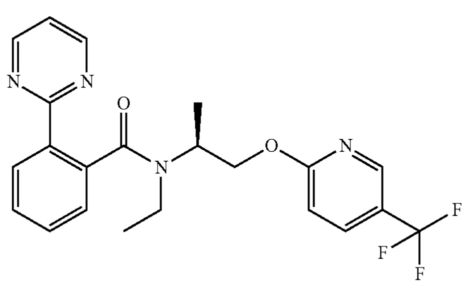 [SMILES: CCN(C(=O)c1ccccc1-c1ncccn1)[C@@H](C)COc1ccc(C(F)(F)F)cn1] | 453 [M + Na]$^+$ | 3.76 | N |

-continued

| Example | Structure | ESI-MS [M + H]⁺ | HPLC (Rt) [min] | HPLC method |
|---|---|---|---|---|
| 105 | 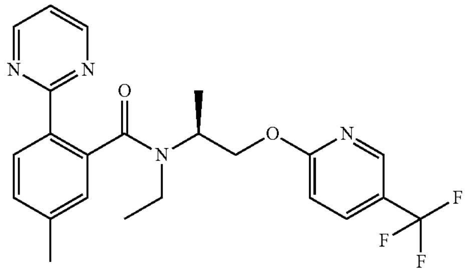 | 467 [M + Na]⁺ | 3.91 | N |
| 107 | 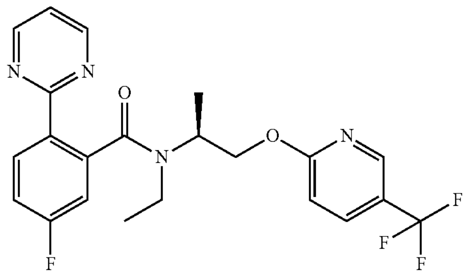 [SMILES: CCN(C(=O)c1cc(F)ccc1-c1ncccn1)[C@@H](C)COc1ccc(C(F)(F)F)cn1] | 449 | 1.13 | F |
| 108 | 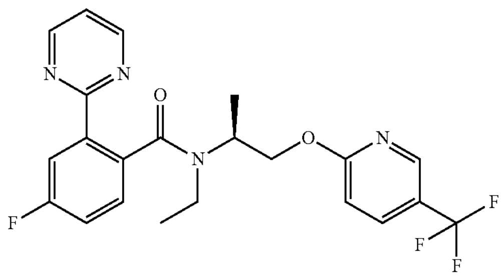 [SMILES: CCN(C(=O)c1ccc(F)cc1-c1ncccn1)[C@@H](C)COc1ccc(C(F)(F)F)cn1] | 449 | 4.04 | N |

Example 128

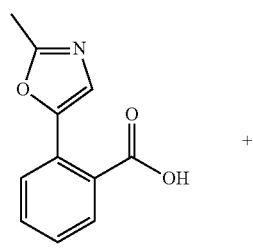

A-58

+

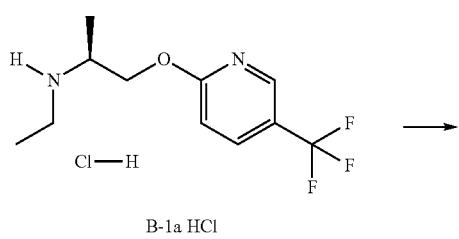

B-1a HCl

-continued

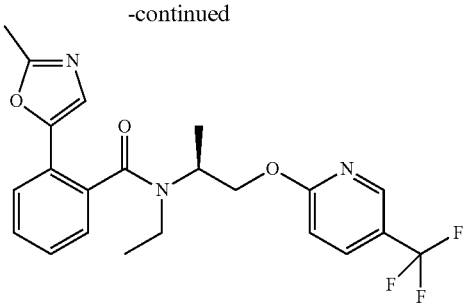

Example 128

To a mixture of A-58 (63 mg, 0.31 mmol) in dry DMF (5 mL) is added B-1a.HCl (80 mg, 0.28 mmol), HATU (141 mg, 0.37 mmol) and DIPEA (243 µL, 1.40 mmol) and the mixture is stirred at RT overnight. The crude product is directly purified by preparative LCMS (using a solvent gradient H₂O/ACN with HCOOH) to afford 50 mg of Example 128. ESI-MS: 456 [M+Na]⁺; HPLC (Rt): 3.76 min (Method N).

The following example is prepared in analogy to the above described procedure using the corresponding acid (see Acid Intermediates) and amine (see Amine Intermediates) as described before:

| Example | Structure | ESI-MS [M + H]⁺ | HPLC (Rt) [min] | HPLC method |
|---|---|---|---|---|
| 123 | 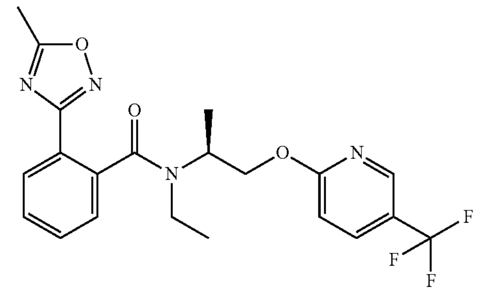 [SMILES: CCN(C(=O)c1ccccc1-c1noc(C)n1)[C@@H](C)COc1ccc(C(F)(F)F)cn1] | 457 [M + Na]⁺ | 3.84 | N |

Example 116

To a mixture of D-3 (110 mg, 0.22 mmol), CuI (3.4 mg, 0.02 mmol), Pd(PPh$_3$)$_4$ (215 mg, 0.02 mmol) in dry DME (2 mL) under nitrogen is added 116.1 (111 μL, 0.35 mmol). The reaction is heated to 120° C. by microwave irradiation for 40 min. After cooling to RT, the mixture is poured into water and extracted with Et$_2$O, the organic layer is dried and concentrated. The residue is purified by flash column chromatography on silica gel (using a solvent gradient cyclohexane/EA 10/0 to 4/6) to provide 16 mg of Example 116. ESI-MS: 449 [M+H]⁺; HPLC (Rt): 1.37 min (Method N).

The invention claimed is:
1. A compound selected from the group consisting of

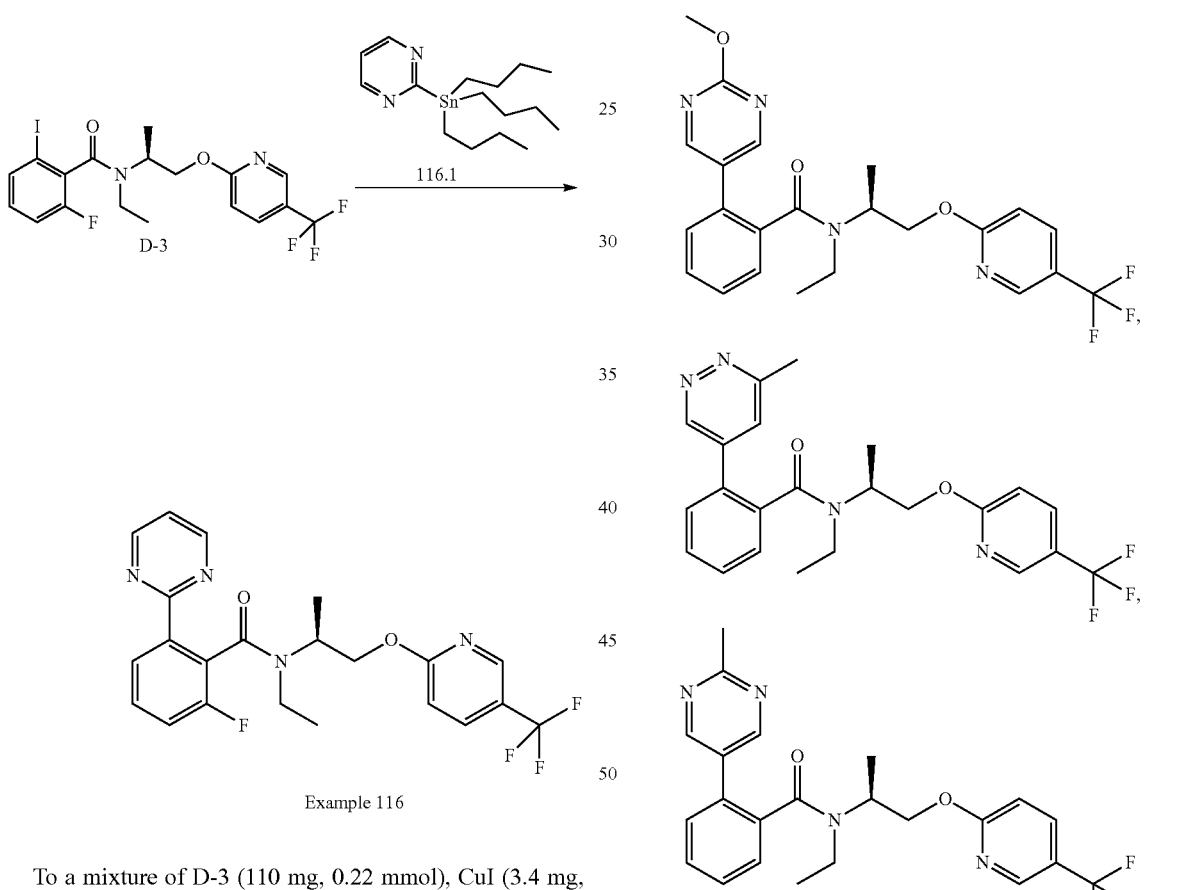

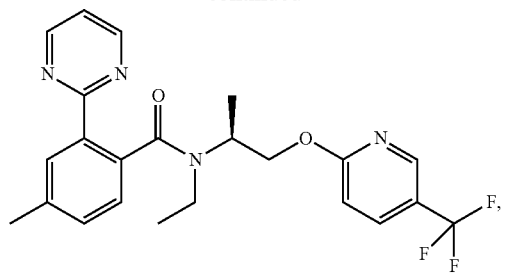
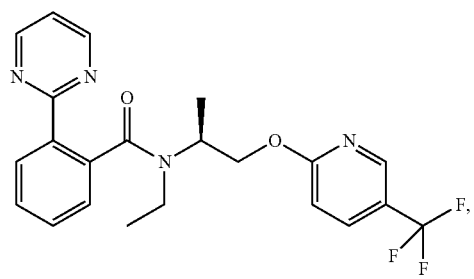
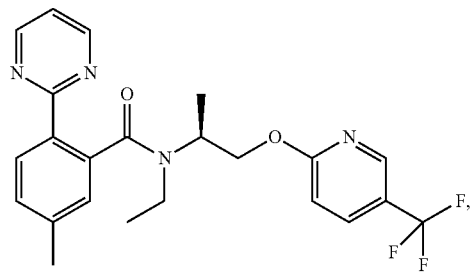
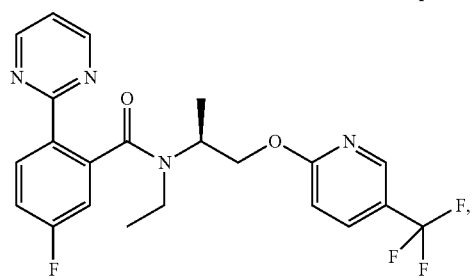
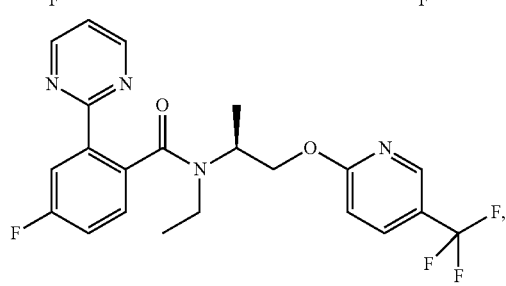
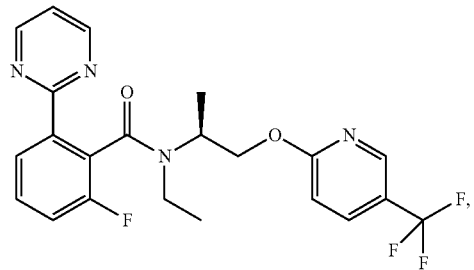
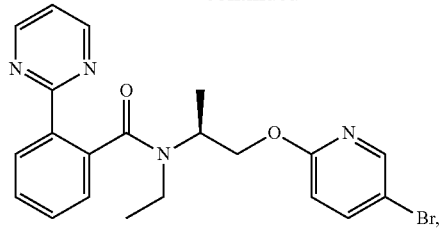
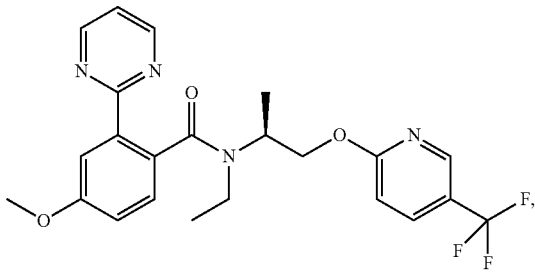
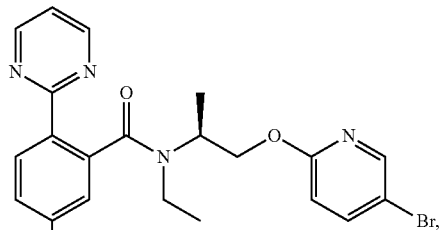
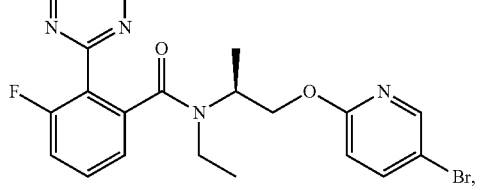
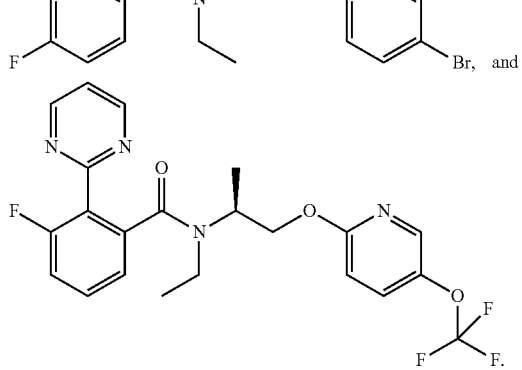
2. A pharmaceutical composition comprising a compound according to claim 1 or a pharmaceutically acceptable salt thereof in admixture with a pharmaceutically acceptable adjuvant, diluent and/or carrier.
3. A pharmaceutically acceptable salt of the compound according to claim 1.

4. A pharmaceutically acceptable salt form of the compound according to claim 1 selected from the group consisting of
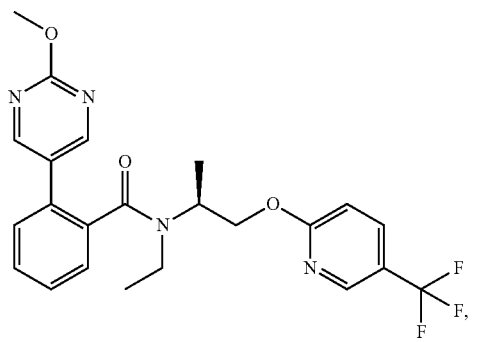 [SMILES: CCN(C(=O)c1ccccc1-c1cnc(OC)nc1)[C@@H](C)COc1ccc(C(F)(F)F)cn1]
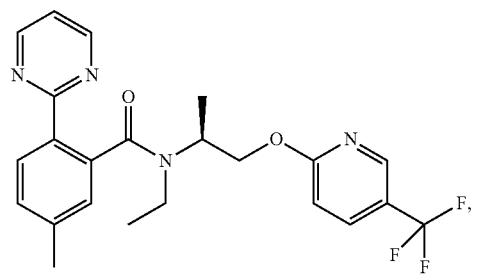
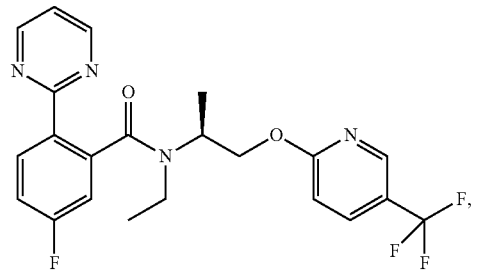
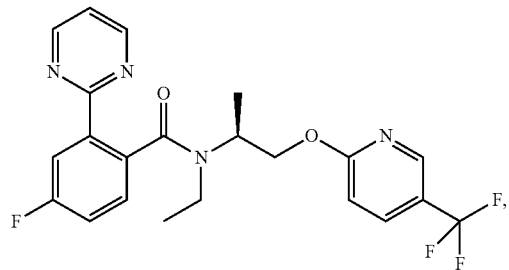
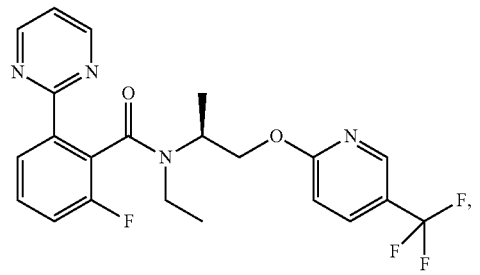
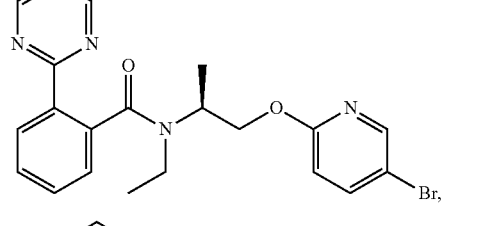
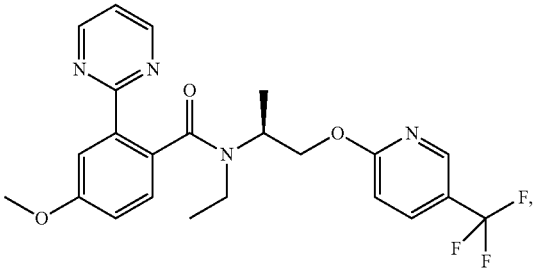

133
-continued
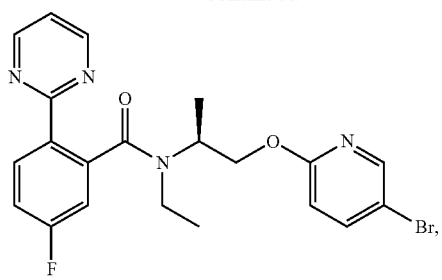
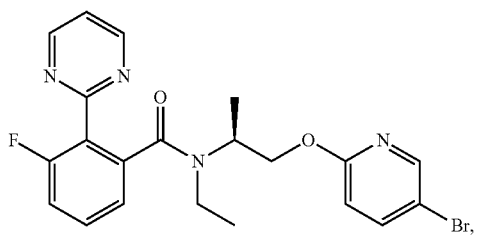
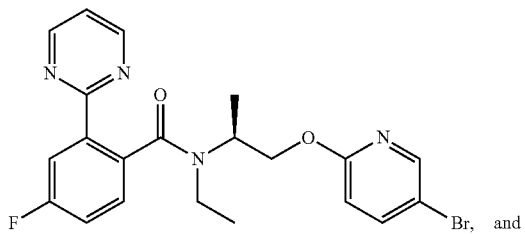
134
-continued
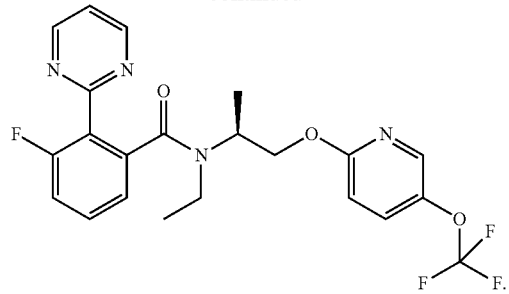
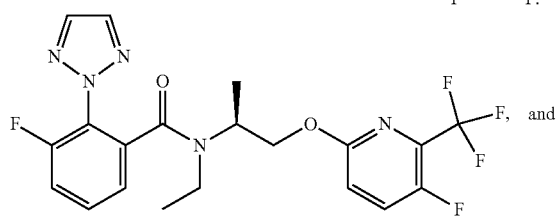
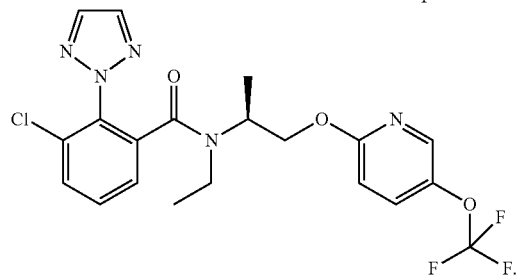
* * * * *